(12) United States Patent
Chatterjee et al.

(10) Patent No.: US 7,517,967 B2
(45) Date of Patent: *Apr. 14, 2009

(54) MONOCLONAL ANTIBODY 1A7 AND USE FOR THE TREATMENT OF MELANOMA AND SMALL CELL CARCINOMA

(75) Inventors: Malaya Chatterjee, Fort Wright, KY (US); Kenneth A. Foon, Fremont, CA (US); Sunil K. Chatterjee, Fort Wright, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 123 days.

This patent is subject to a terminal disclaimer.

(21) Appl. No.: 11/089,266

(22) Filed: Mar. 23, 2005

(65) Prior Publication Data

US 2005/0287148 A1    Dec. 29, 2005

Related U.S. Application Data

(63) Continuation of application No. 10/153,401, filed on May 21, 2002, now abandoned, which is a continuation of application No. 09/293,533, filed on Apr. 15, 1999, now Pat. No. 6,509,016, which is a continuation of application No. 08/752,844, filed on Nov. 21, 1996, now Pat. No. 5,935,821, which is a continuation-in-part of application No. 08/591,196, filed on Jan. 16, 1996, now Pat. No. 5,977,316, and a continuation-in-part of application No. 08/372,676, filed on Jan. 17, 1995, now Pat. No. 5,612,030.

(51) Int. Cl.
C07K 16/00 (2006.01)
A61K 39/395 (2006.01)

(52) U.S. Cl. .............. 530/388.8; 530/387.1; 530/387.7; 530/388.1; 424/130.1; 424/138.1; 424/141.1; 424/155.1

(58) Field of Classification Search ........................ None
See application file for complete search history.

(56) References Cited

U.S. PATENT DOCUMENTS

| 4,675,287 A | 6/1987 | Reisfeld et al. |
| 4,693,966 A | 9/1987 | Houghton et al. |
| 4,722,840 A | 2/1988 | Valenzuela et al. |
| 4,737,456 A * | 4/1988 | Weng et al. ................. 435/7.92 |
| 4,849,509 A | 7/1989 | Thurin et al. |
| 4,904,596 A | 2/1990 | Hakomori |
| 4,918,164 A | 4/1990 | Hellstrom et al. |
| 4,965,498 A | 10/1990 | Yokota |
| 5,009,995 A | 4/1991 | Albino et al. |
| 5,053,224 A | 10/1991 | Koprowski et al. |
| 5,057,540 A | 10/1991 | Kensil et al. |
| 5,091,177 A | 2/1992 | Hellstrom et al. |
| 5,102,663 A | 4/1992 | Livingston et al. |
| 5,134,075 A | 7/1992 | Hellstrom et al. |
| 5,141,742 A | 8/1992 | Brown et al. |
| 5,208,146 A | 5/1993 | Irie |
| 5,240,833 A | 8/1993 | Nudelman et al. |
| 5,242,824 A | 9/1993 | Hellstrom et al. |
| 5,270,202 A | 12/1993 | Raychaudhuri |
| 5,305,559 A | 4/1994 | Ogawa |
| 5,308,614 A | 5/1994 | Hakomori |
| 5,529,922 A | 6/1996 | Chapman et al. |
| 5,571,900 A | 11/1996 | Wiegand et al. |
| 5,612,030 A | 3/1997 | Chatterjee et al. |
| 5,653,977 A | 8/1997 | Saleh |
| 5,935,821 A | 8/1999 | Chatterjee et al. |
| 5,977,316 A | 11/1999 | Chatterjee et al. |
| 6,509,016 B1 | 1/2003 | Chatterjee et al. |
| 2003/0114398 A1 | 6/2003 | Chatterjee et al. |

FOREIGN PATENT DOCUMENTS

| EP | 0 280 209 A2 | 8/1988 |
| EP | 0 368 131 A2 | 5/1990 |
| EP | 0 661 061 A2 | 7/1995 |

(Continued)

OTHER PUBLICATIONS

Essell (J. NIH Res. 1995 7:46).*

(Continued)

*Primary Examiner*—Sheela J Huff
(74) *Attorney, Agent, or Firm*—Stites & Harbison PLLC; Stephen J. Weyer; Richard S. Meyers, Jr.

(57) ABSTRACT

The present invention relates to monoclonal antibody 1A7. This is an anti-idiotype produced by immunizing with an antibody specific for ganglioside GD2, and identifying a hybridoma secreting antibody with immunogenic potential in a multi-step screening process. Also disclosed are polynucleotide and polypeptide derivatives based on 1A7, including single chain variable region molecules and fusion proteins, and various pharmaceutical compositions. When administered to an individual, the 1A7 antibody overcomes immune tolerance and induces an immune response against GD2, which comprises a combination of anti-GD2 antibody and GD2-specific T cells. The invention further provides methods for treating a disease associated with altered GD2 expression, particularly melanoma, neuroblastoma, glioma, soft tissue sarcoma, and small cell carcinoma. Patients who are in remission as a result of traditional modes of cancer therapy may be treat with a composition of this invention in hopes of reducing the risk of recurrence.

5 Claims, 24 Drawing Sheets

FOREIGN PATENT DOCUMENTS

| | | |
|---|---|---|
| WO | WO-86/00909 A1 | 2/1986 |
| WO | WO-92/19266 A1 | 11/1992 |
| WO | WO-93/17105 A1 | 9/1993 |
| WO | WO-94/16731 A1 | 8/1994 |
| WO | WO-94/22479 A1 | 10/1994 |
| WO | WO-95/04548 A1 | 2/1995 |
| WO | WO-95/34638 A1 | 12/1995 |
| WO | WO-96/22373 A2 | 7/1996 |

OTHER PUBLICATIONS

Spitler (Cancer Biotherapy, 1995, 10:1-3).*
Boon (Adv. Can. Res. 1992 58:177-210).*
Manaka et al Dokkyo Journal of Nedical Sciences vol. 12 p. 31 (1985).*
Angeles, T.S. et al. (1993). "Isoabzymes: Structurally and Mechanistically Similar Catalytic Antibodies From the Same Immunization," *Biochemistry* 32: 12128-12135.
Bhattacharya-Chatterjee, M. et al. (1993) "Syngeneic Monoclonal Anti-Idiotype Antibodies Against a Monoclonal Antibody to Human Melanoma Associated Antigen," *J. Immunol.* 150: 142A (Abstract No. 805).
Bird, R.E. et al. (1988) "Single-Chain Antigen-Binding Proteins," *Science* 242:423-426.
Blier, P.R. et al. (1987). "A Limited Number of B Cell Lineages Generates the Heterogeneity of a Secondary Immune Response," *J. Immunol.* 139: 3996-4006.
Chakraborty, M. et al. (1995). "Induction of Human Breast Cancer-Specific Antibody Responses in Cynomolgus Monkeys by a Murine Monoclonal Anti-Idiotype Antibody," *Cancer Res.* 55(7):1525-1530.
Charbonnier, J.B. et al. (1997). "Structural Convergence in the Active Sites of a Family of Catalytic Antibodies," *Science* 275: 1140-1142.
Cheung, N-K.V. et al. (1993). "Disialoganglioside $G_{D2}$ Anti-Idiotypic Monoclonal Antibodies," *Int. J. Cancer* 54: 499-505.
Foon, K.A. et al. (1995). "Immune Response to the Carcinoembryonic Antigen in Patients Treated with an Anti-Idiotype Antibody Vaccine," *J. Clin. Invest.* 96:334-342.
Foon, K.A. et al. (1994). "Anti-Idiotype Antibodies: Novel Therapeutic Approach to Cancer Therapy," *Immunology Series* 61: 281-292.
Guo, J. et al. (1995). "Mechanistically Different Catalytic Antibodies Obtained From Immunization with a Single Transition-State Analog," *Proc. Natl. Acad. Sci. USA* 92: 1694-1698.
Gura, T. (1997). "Systems for Identifying New Drugs Are Often Faulty," *Science* 278: 1041-1042.
Harlow, E. et al. (1988). *Antibodies: A Laboratory Manual*. Cold Spring Harbor Press: Cold Spring Harbor, NY. (Table of Contents).
Hastings, A. et al. (1992). "Production and Characterization of a Murine/Human Chimeric Anti-Idiotype Antibody that Mimics Ganglioside," *Cancer Res.* 52: 1681-1686.
Hawkins, R.E. et al. (1993). "A Genetic Approach to Idiotypic Vaccination," *J. Immunother.* 14: 273-278.
Hawkins, R.E. et al. (1994). "Plasmid Vaccination Against B-Cell Lymphoma," *Cancer Gene Ther.* 1(3):208 (Conference Abstract).
Heidenheim, M. et al. (1995). "CDw60, Which Identifies the Acetylated Form of $G_{D3}$ Gangliosides, is Strongly Expressed in Human Basal Cell Carcinoma," *Brit. J. Dermatol.* 133: 392-397.
Leahy, D.J. et al. (1988). "Sequences of 12 Monoclonal Anti-Dinitrophenyl Spin-Label Antibodies for NMR Studies," *Proc. Natl. Acad. Sci. USA* 85: 3661-3665.
Livingston, P.O. (1995). "Approaches to Augmenting the Immunogenicity of Melanoma Gangliosides: From Whole Melanoma Cells to Ganglioside-KLH Conjugate Vaccines," *Immunol. Rev.* 145: 147-166.
Mittelman, A. et al. (1992). "Human High Molecular Weight Melanoma-Associated Antigen (HMW-MAA) Mimicry by Mouse Anti-Idiotypic Monoclonal Antibody MK2-23: Induction of Humoral Anti-HMW-MAA Immunity and Prolongation of Survival in Patients with Stage IV Melanoma," *Proc. Natl. Acad. Sci. U.S.A.* 89(2):466-470.
Mittelman, A. et al. (1994). "Kinetics of the Immune Response and Regression of Metastatic Lesions Following Development of Humoral Anti-High Molecular Weight-Melanoma Associated Antigen Immunity in Three Patients with Advanced Malignant Melanoma Immunized with Mouse Antiidiotypic Monoclonal Antibody MK2-23," *Cancer Res.* 54(2):415-421.
Miyashita, H. et al.(1994). "A Common Ancestry for Multiple Catalytic Antibodies Generated Against a Single Transition-State Analog," *Proc. Natl. Acad. Sci. USA* 91: 6045-6049.
Moss, B. (1991). "Vaccinia Virus: A Tool for Research and Vaccine Development," *Science* 252:1662-1667.
Mujoo, K. et al. (1989). "Functional Properties and Effect on Growth Suppression of Human Neuroblastoma Tumors by Isotype Switch Variants of Monoclonal Antiganglioside $G_{D2}$ Antibody 14.18," *Cancer Res.* 49: 2857-2861.
Nahmias, C. et al. (1988). "The Immune Response Toward J-Adrenergic Ligands and Their Receptors. VIII. Extensive Diversity of $V_H$ and $V_L$ Genes Encoding Anti-Alprenolol Antibodies," *J. Immunol.* 140: 1304-1311.
Posnett, D.N. et al. (1988). "A Novel Method for Producing Anti-Peptide Antibodies," *J. Biol. Chem.* 263(4):1719-1725.
Qin, H.X. et al. (1996). "Construction of Recombinant Vaccinia Virus Expressing GM-CSF and Its Use as Tumor Vaccine," *Gene Therapy* 3: 59-66.
Saleh, M.N. et al. (1993). "Generation of a Human Anti-Idiotypic Antibody That Mimics the GD2 Antigen," *J. Immunol.* 151(6): 3390-3398.
Seaver, S.S. (1994). "Monoclonal Antibodies in Industry: More Difficult than Originally Thought," *Gen. Eng. News* 14(14):10-11, 21.
Sen, G. et al. (1995). "Murine Monoclonal Antibody-Idiotype Antibody Breaks Tolerance and Induces Specific Antibody Response to Human Disialoganglioside GD2 in Cynomolgus Monkeys," *Abstract_presented at the 9th International Congress of Immunology*, San Francisco, California, A5250, p. 885.
Sen, G. et al. (1997). "Induction of IgG Antibodies by an Anti-Idiotype Antibody Mimicking Disialoganglioside GD2," Galley Proof of article accepted for publication in *J. Immunother.*, 9 pages. p. 75.
Sen, G. et al. (1997). "Murine Monoclonal Anti-Idiotype (Id) Antibody Induces Specific Humoral Responses to the GD2 Ganglioside in Melanoma Patients," *Abstract submitted for AAAAI/AAI/CIS_Joint Meeting*.
Spooner, R.A. et al. (1995). "DNA Vaccination for Cancer Treatment," *Gene Therapy* 2:173-180.
Stenzel-Poore, M.P. et al. (1989). "Clonal Diversity, Somatic Mutation, and Immune Memory to Phosphocholine-Keyhole Limpet Hemocyanin," *J. Immunol.* 143: 4123-4133.
Tsuchida, T. et al. (1987). "Gangliosides of Human Melanoma," *J. Natl. Cancer Inst.* 78: 45-54.
Wang, B. et al. (1995). "Immunization by Direct DNA Inoculation Induces Rejection of Tumor Cell Challenge," *Human Gene Therapy* 6:407-418.
Bhattacharya-Chatterjee, M. et al. (1987). "Idiotype Vaccines Against Human T Cell Acute Lymphoblastic Leukemia. I. Generation and Characterization of Biologically Active Monoclonal Anti-Idiotopes," *J. Immunol.* 139(4): 1354-1360.
Bhattacharya-Chatterjee, M. et al. (1988). "Idiotype Vaccines Against Human T Cell Leukemia. II. Generation and Characterization of a Monoclonal Idiotype Cascade (Ab1, Ab2, and Ab3)," *J. Immunol.* 141(4): 1398-1403.
Bhattacharya-Chatterjee, M. et al. (1990). "Murine Monoclonal Anti-Idiotype Antibody as a Potential Network Antigen for Human Carcinoembryonic Antigen," *J. Immunol.* 145(8): 2758-2765.
Bhattacharya-Chatterjee, M. et al. (1994). "Idiotypic Antibody Immunotherapy of Cancer," *Cancer Immunol. Immunother.* 38: 75-82.
Chapman, P.B. and Houghton, A.N. (1991). "Introduction of IgG Antibodies Against $G_{D3}$ Ganglioside in Rabbits by an Anti-Idiotypic Monoclonal Antibody," *J. Clin. Invest.* 88: 186-192.
Chattopadhyay, P. et al. (1992). "Murine Monoclonal Anti-Idiotype Antibody Breaks Unresponsiveness and Induces a Specific Antibody Response to Human Melanoma-Associated Proteoglycan Antigen in Cynomolgus Monkeys," *Proc. Natl. Acad. Sci. USA* 89: 2684-2688.

Cheresh, D.A. et al. (1984). "Localization of the Gangliosides $G_{D2}$ and $G_{D3}$ in Adhesion Plaques and on the Surface of Human Melanoma Cells," *Proc Natl. Sci. USA* 81: 5767-5771.

Cheresh, D.A. et al. (1986). "Disialoganglioside $G_{D2}$ and $G_{D3}$ are Involved in the Attachment of Human Melanoma and Neuroblastoma Cells to Extracellular Matrix Proteins," *J. Cell. Biol.* 102: 688-696.

Cheresh, D.A. et al. (1986). "Disialoganglioside $G_{D2}$ Distributes Preferentially into Substrate-Associated Microprocesses on Human Melanoma Cells During Their Attachment to Fibronectin," *J. Cell. Biol.* 102: 1887-1897.

Cheresh, D.A. et al. (1986). "Biosynthesis and Expression of the Disialoganglioside $G_{D2}$, a Relevant Target Antigen on Small Cell Lung Carcinoma for Monoclonal Antibody-Mediated Cytolysis," *Cancer Res.* 46: 5112-5118.

Cheung, N-K.V. et al. (1987). "Ganglioside $G_{D2}$ Specific Monoclonal Antibody 3F8: A Phase I Study in Patients with Neuroblastoma and Malignant Melanoma," *J. Clin. Oncol.* 5(9): 1430-1440.

Cheung, N-K.V. et al. (1994). "Antibody Response to Murine Anti-$G_{D2}$ Monoclonal Antibodies: Correlation with Patient Survival," *Cancer Res* 54: 2228-2233.

Chien, N.C. et al. (Mar. 1988). "Point Mutations Cause The Somatic Diversification of IgM and IgG2a Antiphosphorylcholine Antibodies," *J. Exp. Med.* 167: 954-973.

Cochran, M.A. et al. (1985). "In Vitro Mutagenesis of the Promoter Region for a Vaccinia Virus Gene: Evidence for Tandem Early and Late Regulatory Signals," *J. Virol.* 54(1): 30-37.

Hamilton, W.B. et al. (1993). "Ganglioside Expression on Human Malignant Melanoma Assessed by Quantitative Immune Thin-Layer Chromatography," *Int. J. Cancer* 53: 566-573.

Handgretinger, R. et al. (1992). "A Phase I Study of Neuroblastoma with the Anti-Ganglioside GD2 Antibody 14G2a," *Cancer Immunol. Immunother.* 35: 199-204.

Helling, F. et al. (1994). "Ganglioside Conjugate Vaccines," *Mol. Chem. Neuropath.* 21: 299-309.

Hruby, D.E. et al. (1983) "Fine Structure Analysis and Nucleotide Sequence of the Vaccinia Virus Thymidine Kinase Gene," *Proc. Natl. Acad. Sci. USA* 80: 3411-3415.

Irie, R.F. and Morton, D.L. (1986). "Regression of Cutaneous Metastatic Melanoma by Intralesional Injection with Human Monoclonal Antibody to Ganglioside GD2," *Proc. Natl. Acad. Sci. USA* 83: 8694-8698.

Kanda, S. et al. (1994). "Both $V_H$ and $V_L$ Regions Contribute to the Antigenicity of Anti-Idiotypic Antibody that Mimics Melanoma Associated Ganglioside $GM_3$," *Cell Biophys.* 24/25: 65-74.

Kaufman, H. et al. (1991). "A Recombinant Vaccinia Virus Expressing Human Carcinoembryonic Antigen (CEA)," *Int. J. Cancer* 48: 900-906.

Livingston, P.O. et al. (1993). "GD3/Proteosome Vaccines Induce Consistent IgM Antibodies Against the Ganglioside GD3," *Vaccine* 11(12): 1199-1204.

Mujoo, K. et al. (1987). "Disialoganglioside $G_{D2}$ on Human Neuroblastoma Cells: Target Antigen for Monoclonal Antibody-Mediated Cytolysis and Suppression of Tumor Growth," *Cancer Res.* 47: 1098-1104.

Reininger, L. et al. (1990). "Cryoglobulinemia Induced by a Murine IgG3 Rheumatoid Factor: Skin Vasculitis and Glomerulonephritis Arise from Distinct Pathogenic Mechanisms," *Proc. Natl. Acad. Sci. USA* 87(24): 10038-10042.

Saleh, M.N. et al. (1992). "Phase I Trial of the Murine Monoclonal Anti-$G_{D2}$ Antibody 14G2a in Metastatic Melanoma," *Cancer Res.* 52: 4342-4347.

Tam, J.P. (1989). "High-Density Multiple Antigen-Peptide System for Preparation of Antipeptide Antibodies," *Meth. Enz.* 168:7-15.

Tang, D. et al. (1992). "Genetic Immunization is a Simple Method for Eliciting an Immune Response," *Nature* 356: 152-154.

Yamamato, S. et al. (1990). "Anti-Idiotype Monoclonal Antibody Carrying the Internal Image of Ganglioside GM3," *J. Natl. Cancer Inst.* 82(22): 1757-1760.

\* cited by examiner

Figure 1

```
  M   K   L   P   V   R   L   L   V   L   M   F   W   I   P   A
 ATG AAG TTG CCT GTT AGG CTG TTG GTG CTG ATG TTC TGG ATT CCT GCT
  S   S   D
 TCC AGC GAT   (-1 to -19, leader)

D   V   L   M   T   Q   T   P   L   S   L   P   V   S   L   G
 GAT GTT TTG ATG ACC CAA ACT CCA CTC TCC CTG CCT GTC AGT CTT GGA
  D   Q   A   S   I   S   C
 GAT CAA GCC TCC ATC TCT TGC   (1-23, Frame work 1)

R   S   S   Q   S   I   V   H   S   N   G   N   T   Y   L   E
 AGA TCT AGT CAG AGC ATT GTA CAT AGT AAT GGA AAC ACC TAT TTA GAA
 (24-39, CDR 1)

W   Y   L   Q   K   P   G   Q   S   P   N   L   L   I   Y
 TGG TAC CTA CAG AAA CCA GGC CAG TCT CCA AAC CTC CTG ATC TAC
 (40-54, Frame work 2)

F   V   S   N   R   F   S
 TTT GTT TCC AAC CGA TTT TCT   (55-61, CDR 2)

G   V   P   D   R   F   S   G   S   G   S   G   T   D   F   T
 GGG GTC CCA GAC AGG TTC AGT GGC AGT GGA TCA GGG ACA GAT TTC ACA
  L   K   I   S   R   V   E   A   E   D   L   G   V   Y   Y   C
 CTC AAG ATC AGC AGA GTG GAG GCT GAG GAT CTG GGA GTT TAT TAC TGC
 (62-93, Frame work 3)

F   Q   G   S   H   V   P   W   T
 TTT CAA GGT TCA CAT GTT CCG TGG ACG
 (94-102, CDR 3)

F   G   G   G   T   K   L   E   I   K
 TTC GGT GGA GGC ACC AAG CTG GAA ATC AAA
 (103-112, Frame work 4)

R   A   D   A   A   P   T   V   S   I   F   P   P
 CGG GCT GAT GCT GCA CCA ACT GTA TCC ATC TTC CCA CCA

S   S   K   L   G
 TCC AGT AAG CTT GGG   (Constant region)
```

Figure 2

```
  M   A   V   L   G   L   L   F   C   L   V   T   F   P   S   C
ATG GCT GTC TTG GGG CTG CTC TTC TGC CTG GTG ACA TTC CCA AGC TGT
  V   L   S
GTC CTG TCC   (-1 to -19, Leader)

Q   V   Q   V   K   E   S   G   P   F   L   V   P   P   S   Q
CAG GTG CAG GTG AAG GAG TCA GGA CCT TTC CTG GTG CCC CCC TCA CAG
  S   L   S   I   T   C   T   V   S   G   F   S   L   T
AGC CTG TCC ATC ACA TGC ACT GTC TCA GGG TTC TCA TTA ACC
  (1-30, Frame work 1)

T   Y   G   V   S
ACC TAT GGT GTA AGC   (31-35, CDR 1)

W   I   R   Q   P   P   G   K   G   L   E   W   L   G
TGG ATT CGC CAG CCT CCA GGA AAG GGT CTG GAG TGG CTG GGA
  (36-49, Frame work 2)

A   I   W   G   D   G   T   T   N   Y   H   S   A   L   I   S
GCA ATT TGG GGT GAC GGG ACC ACA AAT TAT CAT TCA GCT CTC ATA TCC
  (50-65, CDR 2)

R   L   S   I   S   K   D   N   S   K   S   Q   V   F   L   K
AGA CTG AGC ATC AGC AAG GAT AAC TCC AAG AGC CAA GTT TTC TTA AAA
  L   N   S   L   Q   T   D   D   T   A   T   Y   Y   C   A   K
CTG AAC AGT CTG CAA ACT GAT GAC ACG GCC ACG TAC TAC TGT GCC AAA
  (66-97, Frame work 3)

L   G   N   Y   D   A   L   D   W
CTG GGT AAC TAC GAT GCT CTG GAC TAC
  (98-106, CDR 3)

W   G   Q   G   T   S   V   T   V   S   S
TGG GGT CAA GGA ACC TCA GTC ACC GTC TCC TCA
  ( 107-117, Frame work 4)

A   K   T   T   P   P   P   V   Y   P   L   V   P   G   S   L
GCC AAA ACG ACA CCC CCA CCC GTC TAT CCA TTG GTC CCT GGA AGC TTG GG
  (Constant region)
```

Figure 3(A)

```
1A7:     1  DVLMTQTPLSLPVSLGDQASISCRSSQSIVHSNGNTYLEWYLQKPGQSPNLLIYFVSNRF  60
 1       1  ............................................K...K.....       60
 2       1  ............................................K...K.....       60
 3       1  ..V.........................................K...K.....       60
 4       1  ............................................K...K.....       60
 5       1  ............................................K...K.....       60
 6       1  ............................................K...K.....       60
 7       1  ............................................K...K.....       60
 8       1  .........................................X..K...K.....       60
 9       5  ...........................S...F............K...K.....       64
10       1  ............................................K...K.....       60
11       1  ............................................K...K.....       60
12      20  ............................................K...K.....       79
13       1  ............................................K...K....L       60
14       1  ............................................K...K.....       60
15       5  ...........................S...F............K...K.....       64

1A7:    61  SGVPDRFSGSGSGTDFTLKISRVEAEDLGVYYCFQGSHVPWTFGGGTKLEIK  112
 1      61  ...................,................................  112
 2      61  ....................................................  112
 3      61  ....................................................  112
 4      61  ....................................................  111
 5      61  ....X...............................................  112
 6      61  .........................................Y..........  112
 7      61  ........C...........................................  111
 8      61  ....................................................  111
 9      65  .........................................T..........  116
10      61  ...............R.........................Y..........  112
11      61  .........................................R..........  112
12      80  .........................................Y...S......  131
13      61  .........................................Y..........  112
14      61  .......T...........................W.....Y..........  112
15      65  ...........................Q.............T..........  116
```

Figure 3(B)

```
1A7:    1  QVQVKESGPFLVPPSQSLSITCTVSGFSLTTYGVSWIRQPPGKGLEWLGAIWGDGTTNYH   60
  1     1  .........G..A.............S.....V.............V.....S....    52
  2     1  ...LQ....G..A.............S..IT.V.............V:....N.:...  60
  3    20  ...L.....G..A.............G...N.V.............T...N.S.D.N   79
  4     1  ...L..T..G..A.............S...H.V............VV..S..S...N   60
  5     1  ...L.....G..A.............S...H.V.............V..AG.S...N   60
  6     1  ...L.....G..A.............S...H.V.............V..AG.S...N   60
  7     1  ...L.....G..A.............P..S..D.V...........V...G.S...N   60
  8    23  ...LQ....G..A.............G...N.V.............M.....N.D.N   82
  9     1  ...L.....G..A.............G...N.V.............M.....N.D.N   60
 10   133  ...LQ....G..A.............G...N.V.............M.....N.D.N  192
 11    20  ...L.....G..A.............G...N.V.............M.....N.D.N   79
 12     1  ...L.....G..A............SR.S.H.V.............M...G.N.D.N   60
 13    21  .HL.....V..A..............N...H.V.............V..AG.N...N   80
 14    23  ...LQ....G..A.............G...N.V.............M.....N.D.N   82
 15     1  ...LQ....G..A.............G...N.V.............M.....N.D.N   60

1A7:   61  SALISRLSISKDNSKSQVFLKLNSLQTDDTATYYCAKL-------GNYDALDWWGQGTSVTVSS  117
  1    53  ..........................P-----YDYExxxxx.Y.....TL..  109
  2    61  ...............................x----xxxxxxx.K.Y..........  120
  3    80  .T.K...T.T.........M........R....SVSIYYYGRSDK.FT..Y..........  144
  4    61  ...K..............H........H....Rx-----xx.D.Y.H.Y  119
  5    61  ...M..............H........H....Rx----xxxxxx.Y.H.Y  120
  6    61  ...M..............H........H....Rx----xxxx.Y.H.Y  118
  7    61  ...M..............H...X....H....xx-----xxx.X.Y.M.Y  119
  8    83  ...K..............M..H.....R....RE--------=RDYR..Y.....T.....  138
  9    61  ...K..............M..H.....R....RE--------=RDYR..Y.....TL....  116
 10   193  ...K..............M..H.....R....RE--------=RDYR..Y.....T.....  248
 11    80  ...K..............M..H.....R....RE--------=RDYR..Y.....TL....  135
 12    61  ...M..............M.........M...RD-------GYYDx.M.Y..........  117
 13    81  ...M..............H...I....I....x-----xxxxx.Y.M.Y..........  139
 14    83  ...K..............M..H.....R....RE--------=RDYR..Y.....T.....  138
 15    61  ...K..............M..H.....R....RE--------=RDYR..Y.....T.....  116
```

Figure 3(C)

```
                         ****************       *****
VL consensus:  1  DVLMTQTPLSLPVSLGDQASISCRSSQSIVHSNGNTYLEWYLQKKGQSPKLLIYFVSNRF  60
1A7:           1  ..........................................P....N..........  60

*                           *********
VL consensus: 61  SGVPDRFSGSGSGTDFTLKISRVEAEDLGVYYCFQGSHVPWTFGGGTKLEIK        112
1A7:          61  ....................................................        112

****              **********
VH consensus:  1  QVQLKESGPGLVAPSQSLSITCTVSGFSLTSYGVHWVRQPPGKGLEWLGVIWGDGSTNYN  60
1A7:           1  ...V.....F..P..............T...S.I............A.....T...H  60

****                              ***********
VH consensus: 61  SALKSRLSISKDNSKSQVFLKMNSLQTDDTARYYCARExxxxYYAMDYWGQGTSVTVSS  119
1A7:          61  ...I............L.........T....KL--GN.D.L.W..........      117
```

Figure 12
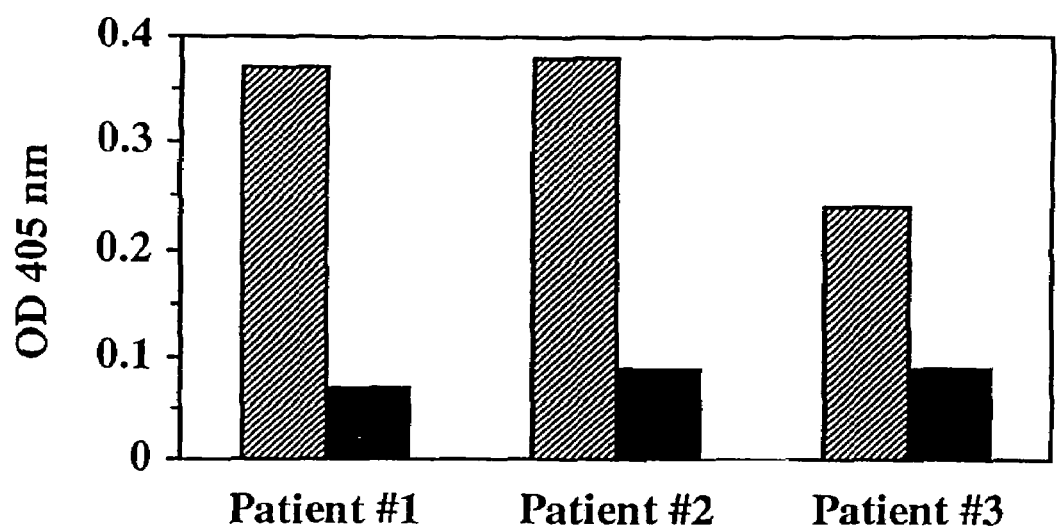
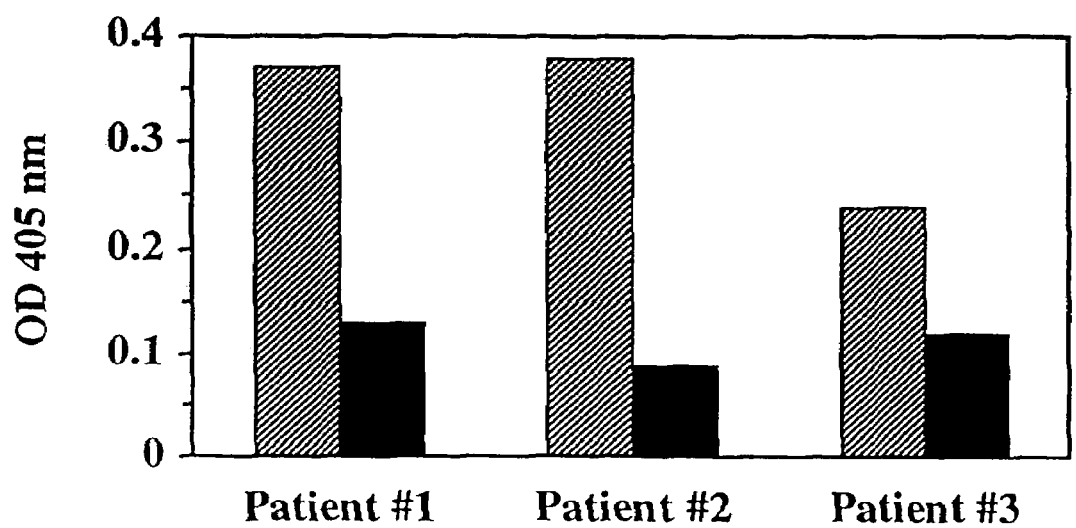

Figure 13
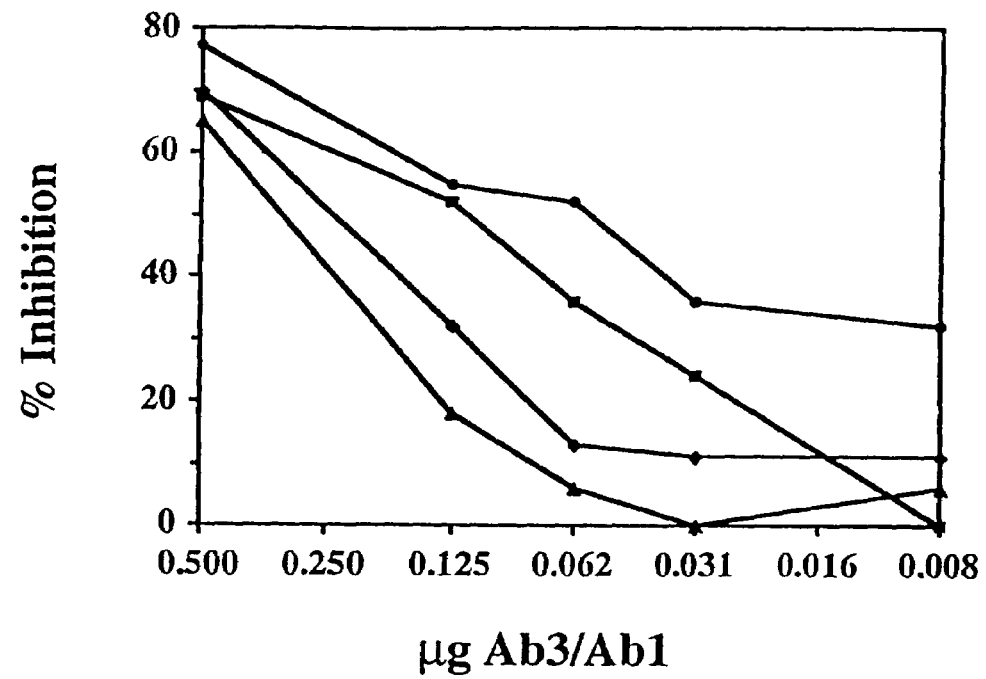
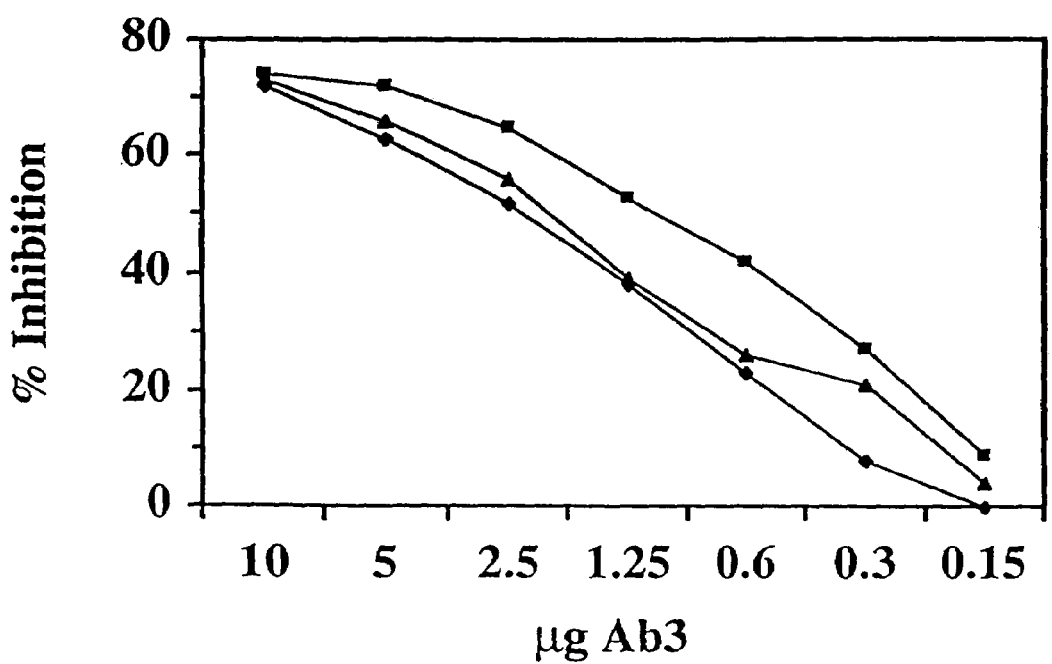

Figure 15

GCCGATATCACCATGGCTGTCTTGGGGCTGCTCTTCTGCCTGGTGACATTCCCAAGC
TGTGTCCTGTCCCAGGTGCAGGTGAAGGAGTCAGGACCTTTCCTGGTGCCCCCTCA
CAGAGCCTGTCCATCACATGCACTGTCTCAGGGTTCTCATTAACCACCTATGGTGTA
AGCTGGATTCGCCAGCCTCCAGGAAAGGGTCTGGAGTGGCTGGGAGCAATTTGGGG
TGACGGGACCACAAATTATCATTCAGCTCTCATATCCAGACTGAGCATCAGCAAGGA
TAACTCCAAGAGCCAAGTTTTCTTAAAACTGAACAGTCTGCAAACTGATGACACGGC
CACGTACTACTGTGCCAAACTGGGTAACTACGATGCTCTGGACTACTGGGGTCAAGG
AACCTCAGTCACCGTCTCCTCA*GGGGGAGGTGGCTCGGGCGGTGGCGGCTCGGGTGG
CGGCGGATCC*GATGTTTTGATGACCCAAACTCCACTCTCCCTGCCTGTCAGTCTTGGA
GATCAAGCCTCCATCTCTTGCAGATCTAGTCAGAGCATTGTACATAGTAATGGAAAC
ACCTATTTAGAATGGTACCTACAGAAACCAGGCCAGTCTCCAAACCTCCTGATCTAC
TTTGTTTCCAACCGATTTTCTGGGGTCCCAGACAGGTTCAGTGGCAGTGGATCAGGG
ACAGATTTCACACTCAAGATCAGCAGAGTGGAGGCTGAGGATCTGGGAGTTTATTAC
TGCTTTCAAGGTTCACATGTTCCGTGGACGTTCGGTGGAGGCACCAAGCTGGAAATC
AAATAATCTAGAGATG

| 1 | mavlgllfcl | vtfpscvlsq | vqvkesgpfl | vppsqslsit | ctvsgfsltt |
| 51 | ygvswirqpp | gkglewlgai | wgdgttnyhs | alisrlsisk | dnsksqvflk |
| 101 | lnslqtddta | tyycaklgny | daldywgqgt | svtvssgggg | sggggsgggg |
| 151 | sdvlmtqtpl | slpvslgdqa | siscrssqsi | vhsngntyle | wylqkpgqsp |
| 201 | nlliyfvsnr | fsgvpdrfsg | sgsgtdftlk | isrveaedlg | vyycfqgshv |
| 251 | pwtfgggtkl | eik | | | |

Figure 17(A)

>gb|L22327|MUSIGKAVAA Mouse rearranged immunoglobulin kappa-chain mRNA V-J

```
  1 GATGTTTTGATGACCCAAACTCCACTCTCCCTGCCTGTCAGTCTTGGAGATCAAGCCTCC  60
 61 ATCTCTTGCAGATCTAGTCAGAGCATTGTACATAGTAATGGAAACACCTATTTAGAATGG 120
121 TACCTGCAGAAACCAGGCCAGTCTCCAAAGCTCCTGATCTACAAAGTTTCCAACCGATTT 180
181 TCTGGGGTCCCAGACAGGTTCAGTGGCAGTGGATCAGGGACAGATTTCACACTCAAGATC 240
241 AGCAGAGTGGAGGCTGAGGATCTGGGAGTTTATTACTGCTTTCAAGGTTCACATGTTCCG 300
301 TGGACGTTCGGTGGAGGCACCAAGCTGGAAATCAAA 336
```

>gb|L18941|MUSIG4388 Mouse rearranged immunoglobulin light chain Ab438 mRNA V-J

```
  1 GATGTTTTGATGACCCAAACTCCACTCTCCCTGCCTGTCAGTCTTGGAGATCAAGCCTCC  60
 61 ATCTCTTGCAGATCTAGTCAGAGCATTGTACATAGTAATGGAAACACCTATTTAGAATGG 120
121 TACCTGCAGAAACCAGGCCAGTCTCCAAAGCTCCTGATCTACAAAGTTTCCAACCGATTT 180
181 TCTGGGGTCCCAGACAGGTTCAGTGGCAGTGGATCAGGGACAGATTTCACACTCAAGATC 240
241 AGCAGAGTGGAGGCTGAGGATCTGGGAGTTTATTACTGCTTTCAAGGTTCACATGTTCCG 300
301 TGGACGTTCGGTGGAGGCACCAAGCTGGAAATCAAA 336
```

>gb|M34588|MUSIGKA8R Mouse Ig kappa-chain mRNA V-J region, partial cds.

```
  1 GATGTTTTGATGACCCAAACTCCACTCTCCCTNCCTGTCAGTCTTGGAGATCAAGCCTCC  60
 61 ATCTCTTGCAGATCTAGTCAGAGCATTGTACATAGTAATGGAAACACCTATTTAGAATGG 120
121 TACCTGCAGAAACCAGGCCAGTCTCCAAAGCTCCTNATCTACAAAGTTTCCAACCGATTT 180
181 TCTGGGGTCCCAGACAGGTTCAGTGGCAGTGGATCAGGGACAGATTTCACACTCAAGATC 240
241 AGCAGAGTGGAGGCTGAGGATCTGGGAGTTTATTACTGCTTTCAAGGTTCACATGTTCCG 300
301 TGGACGTTCGGTGGAGGCACCAAGCTGGAAATCAAA 336
```

>gb|M32857|MUSIGKCSP Mouse Ig rearranged kappa-chain mRNA V-region, partial

```
  1 GATGTTTTGATGACCCAAACTCCACTCTCCCTGCCTGTCAGTCTTGGAGATCAAGCCTCC  60
 61 ATCTCTTGCAGATCTAGTCAGAGCATTGTACATAGTAATGGAAACACCTATTTAGAATGG 120
121 TACCTGCAGAAACCAGGCCAGTCTCCAAAGCTCCTGATCTACAAAGTTTCCAACCGATTT 180
181 TCTGGGGTCCCAGACAGGTTCAGTGGCAGTGGATCAGGGACAGATTTCACACTCAAGATC 240
241 AGCAGAGTGGAGGCTGAGGATCTGGGAGTTTATTACTGCTTTCAAGGTTCACATGTTCCG 300
301 TGGACGTTCGGTGGAGGCACCAAGCTGGAAATC 333
```

>gb|M83723|MUSIGKD2A Mouse monoclonal antiidiotypic antibody Ig kappa light

```
  1 GATGTTTTGATGACCCAAACTCCACTCTCCCTGCCTGTCAGTCTTGGAGATCAAGCCTCC  60
 61 ATCTCTTGCAGATCTAGTCAGAGCATTGTACATAGTAATGGAAACACCTATTTAGAATGG 120
121 TACCTGCAGAAACCAGGCCAGTCTCCAAAGCTCCTGATCTACAAAGTTTCCAACCGATTT 180
181 TCTGGGGTCCCAGACAGGTTCAGTGGCAGTGGATCAGGGACAGATTTCACACTCAAGATC 240
241 AGCAGAGTGGAGGCTGAGGATCTGGGAGTTTATTACTGCTTTCAAGGTTCACATGTTCCT 300
301 CGGACGTTCGGTGGAGGCACCAAGCTGGAAATCAAA 336
```

>emb|Z22035|MDIGKVAH M.domesticus IgK variable region.

```
  1 GATGTTGTGATGACCCAAACTCCACTCTCCCTGCCTGTCAGTCTTGGAGATCAAGCCTCC  60
 61 ATCTCTTGCAGATCTAGTCAGAGCATTGTACATAGTAATGGAAACACCTATTTAGAATGG 120
121 TACCTGCAGAAGCCAGGCCAGTCTCCAAAGCTCCTGATCTACAAAGTTTCCAACCGATTT 180
181 TCTGGGGTCCCAGACAGGTTCAGTGGCAGTGGATCAGGGACAGATTTCACACTCAAGATC 240
241 AGCAGAGTGGAGGCTGAGGATCTGGGAGTTTATTACTGCTTTCAAGGTTCACATGTTCCG 300
301 TGGACGTTCGGTGGAGGCACCAAGCTGGAAATCAAA 336
```

Figure 17(B)

>gb|M34589|MUSIGKABS Mouse Ig kappa-chain mRNA V-J region, partial cds.

```
  1 GATGTTTTGATGACNCAAACTCCACTCTCCCTGCCTGTCAGTCTTGGAGATCAAGCCTCC  60
 61 ATCTCTTGCAGATCTAGTCAGAGCATTGTACATAGTAATGGAAACACCTATTTAGAATGG 120
121 TACCTGCAGAAACCAGGCCAGTCTCCAAAGCTCCTNATCTACAAAGTTTCCAACCGATTT 180
181 TCTGGGGTCCCAGANAGGTTCAGTGGCAGTGGATCAGGGACAGATTTCACACTCAAGATC 240
241 AGCAGAGTGGAGGCTGAGGATCTGGGAGTTTATTACTGCTTTCAAGGTTCACATGTTCCG 300
301 TGGACGTTCGGTGGAGGCACCAAGCTGGAAATCAAA 336
```

>gb|M32858|MUSIGKCSQ Mouse Ig rearranged kappa-chain mRNA V-region, partial

```
  1 GATGTTTTGATGACCCAAACTCCACTCTCCCTGCCTGTCAGTCTTGGAGATCAAGCCTCC  60
 61 ATCTCTTGCAGATCTAGTCAGAGCATTGTACATAGTAATGGAAACACCTATTTAGAATGG 120
121 TACCTGCAGAAACCAGGCCNGTCTCCAAAGCTCCTGATCTACAAAGTTTCCAACCGATTT 180
181 TCTGGGGTCCCAGACAGGTTCAGTGGCAGTGGATCAGGGACAGATTTCACACTCAAGATC 240
241 AGCAGAGTGGAGGCTGAGGATCTGGGAGTTTATTACTGCTTTCAAGGTTCACATGTTCCG 300
301 TGGACGTTCGGTGGAGGCACCAAGCTGGAAATC 333
```

>emb|X87231|MMKAPLI M.musculus mRNA for antibody light chain

```
 89 GATGTTTTAATGACCCAAACTCCACTCTCCCTGCCTGTCAGTCTTGGAGATCAAGCCTCC 148
149 ATCTCTTGCAGATCTAGTCAGAGCATTGTACATAGTAATGGAAACACCTATTTAGAATGG 208
209 TACCTGCAGAAACCAGGCCAGTCTCCAAAGCTCCTGATCTACAAAGTTTCCAACCGATTT 268
269 TCTGGGGTCCCAGACAGGTTCAGTGGCAGTGGATCAGGGACAGATTTCACACTCAAGATC 328
329 AGCAGAGTGGAGGCTGAGGATCTGGGAGTTTATTACTGCTTTCAAGGTTCACATGTTCCG 388
389 TGGACGTTCGGTGGAGGCACCAAGCTGGAAATCAAA 424
```

>gb|U29428|MMU29428 Mus musculus anti-PC rearranged Ig kappa chain V-J region

```
 13 GATGTTTTGATGACCCAAACTCCACTCTCCCTGCCTGTCAGTCTTGGAGATCAAGCCTCC  72
 73 ATCTCTTGCAGATCTAGTCAGAGCATTGTACATAGTAGTGGAAACACCTTTTTAGAATGG 132
133 TACCTGCAGAAACCAGGCCAGTCTCCAAAGCTCCTGATCTACAAAGTTTCCAACCGATTT 192
193 TCTGGGGTCCCAGACAGGTTCAGTGGCAGTGGATCAGGGACAGATTTCACACTCAAGATC 252
253 AGCAGGGTGGAGGCTGAGGATCTGGGAGTTTATTACTGCTTTCAAGGTACACATGTTCCG 312
313 TGGACGTTCGGTGGAGGCACCAAGCTGGAAATCAAA 348
```

Figure 18(A)

>gb|U01185|MMU01185 Mus musculus BALB/c anti-glycophorin A type M

```
  1 CAGGTGCAGCTGCAGGAGTCAGGACCTGGCCTGGTGGCGCCCTCACAGAGCCTGTCCATC 60
 61 ACATGCACTGTCTCAGGGTTCTCATTAACCAGCTATGGTATAACCTGGGTTCGCCAGCCT 120
121 CCAGGAAAGGGTCTGGAGTGGCTGGGAGTAATATGGGGTGACGGAAACACAAATTATCAT 180
181 TCAGCTCTCATATCCAGACTGAGCATCAGCAAGGATAACTCCAAGAGCCAAGTTTTCTTA 240
241 AAACTGAACAGTCTGCAAACTGATGACACAGCCACGTACTACTGTGCCAAA 291
292 ---------------------- 315
316 GCTAAGGACTACTGGGGTCAAGGAACCTCAGTCACCGTCTCCTCA 360
```

>gb|M26985|MUSIGH1PR Mus musculus productively rearranged IgH chain allele 1,

```
  1 CAGGTGCAGCTGAAGGAGACAGGACCTGGCCTGGTGGCGCCCTCACAGAGCCTGTCCATC 60
 61 ACATGCACCGTCTCAGGGTTCTCATTAACCAGCTATGGTGTACACTGGGTTCGCCAGCCT 120
121 CCAGGAAAGGGTCTGGAGTGGCTGGTAGTGATATGGAGTGATGGAAGCACAAACTATAAT 180
181 TCAGCTCTCAAATCCAGACTGAGCATCAGCAAGGACAACTCCAAGAGCCAAGTTTTCTTA 240
241 AAAATGAACAGTCTCCAAACTGATGACACAGCCATGTACTACTGTGCCAGAC 292
293 -------- 300
301 GGTGACTACTATGCTATGGACTACTGGGGTCAAGGAACCTCAGTCACCGTCTCCTCA 357
```

>dbj|D17387|PVYIB Potato virus Y immunoglobulin gene for monoclonal antibody

```
 58 CAGGTGCAGCTGAAGGAGTCAGGACCTGGCCTGGTGGCGCCCTCACAGAGCCTGTCCATC 117
118 ACATGCACTGTCTCAGGGTTCTCATTAACCAGCTATGGTGTAAGCTGGGTTCGCCAGCCT 177
178 CCAGGAAAGGGTCTGGAGTGGCTGGGAGTAATATGGGGTGACGGGAGCACAAATTATCAT 237
238 TCAGCTCTCATATCCAGACTGAGCATCAGCAAGGATAACTCCAAGAGCCAAGTTTTCTTA 297
298 AAACTGAACAGTCTGCAAACTGATGACACAGCCACGTACTACTGTGCCAAGCATCTTGAC 357
358 TAC 360
361 TGGGGCCAAGGCACCACTCTCACAGTCTCCTCA 393
```

>gb|M36228|MUSIGHAEI Mouse Ig heavy-chain mRNA V region, partial cds from

```
  1 CAGGTGCAGCTGAAGGAGTCAGGACCTGGCCTGGTGGCGCCCTCACAGAGCCTGTCCATC 60
 61 ACTTGCACTGTCTCTGGGTTTTCATTAACCAGCTATGGTGTACACTGGGTTCGCCAGCCT 120
121 CCAGGAAAGGGTCTGGAGTGGCTGGGAGTAATATGGGCTGGTGGAAGCACAAATTATAAT 180
181 TCGGCTCTCATGTCCAGACTGAGCATCAGCAAAGACAACTCCAAGAGCCAAGTTTTCTTA 240
241 AAAATGAACAGTCTGCAAACTGATGACACAGCCATGTACTACTGTGCCAGAGGGCATTAC 300
301 TACG 304
305 - 305
306 CTACTATGCTATGGACTACTGGGGTCAAGGAACCTCAGTCACCGTCTCC 354
```

>gb|L48671|MUSAB Mus musculus (cell line C3H/F2-22) chromosome 12 anti-DNA

```
  1 CAGGTGCAGCTCAAGGAGTCAGGACCTGTCCTCGTGGCGCCCTCACAGAGCCTGTCCATC 60
 61 ACTTGCACTGTCTCTGGGTTTTCATTAACCAGCTATGGTGTACACTGGGTTCGCCAGCCT 120
121 CCAGGCAAGGGTCTGGAGTGGCTGGGAGTAATATGGGCTGGTGGAAGCACAAATTATAAT 180
181 TCAGCTCTCATGTCCAGACTGAGCATCAGCAAAGACAACTCCAAGAGCCAAGTTTTCTTA 240
241 AAAATGAACAGTCTGCAAACTGATGACACAGCCATGTACTACTGTGCCAAAC 292
293 ------------ 304
305 ACAATGCTATGGACTACTGGGGTCAAGGAACCTCAGTCACNGTCTCCTCA 354
```

Figure 18(B)

>emb|X75099|MMASHS1H M.musculus (A.SW) mRNA for ASWS1 antibody heavy chain

```
  1 CAGGTNCAGCTGAAGGAGTCAGGACCTGGCCTGGTGGCACCCTCACAGAGCCTGTCCATC  60
 61 ACATGCACTGTCTCTGGGTTCTCATTATCCAGATATAGTGTACACTGGGTTCGCCAGCCT 120
121 CCAGGAAAGGGTCTTGAGTGGCTGGGAATGATATGGGGTGGTGGAAACACAGACTATAAT 180
181 TCAGCTCTCAAATCCAGACTGAGCATCAGCAAGGACAACTCCAAGAGCCAAGTTTTCTTA 240
241 AAAATGAACAGTCTGCAAACTGATGACACAGCCATGTACTACTGTGCCAGAGATGGTTAC 300
301 TACGACTATGCTATGGACTACTGGGGTCAAGGAACCTCAGTCACCGTCTCC 351
```

>gb|M36217|MUSIGHADX Mouse Ig heavy-chain mRNA V region, partial cds.

```
  1 CAGGTGCAGCTGAAGGAGTCAGGACCTGGCCTGGTGGCGCCCTCACAGAGCCTGTCCATC  60
 61 ACTTGCACTGTCTCTGGGTTTTCATTAACCAGCTATGGTGTACACTGGGTTCGCCAGCCT 120
121 CCAGGAAAGGGTCTGGAGTGGCTGGGAGTAATATGGGCTGGTGGAAGCACAAATTATAAT 180
181 TCGGCTCTCATGTCCAGACTGAGCATCAGCAAAGACAACTCCAAGAGCCAAGTTTTCTTA 240
241 AAAATGAACAGTCTGCAAACTGATGACACAGCCATGTACTACTGTGCCAGA 291
292 -------------------- 312
313 TACTATGCTATGGACTACTGGGGTCAAGGAACCTCAGTCACCGTCTCC 360
```

>gb|J04609|MUSIGHAF Mus musculus IgH chain (anti-fluorescein antibody 18-2-3)

```
 67 CACGTGCACCTGAAGGAGTCAGGACCTGTCCTGGTGGCGCCCTCACAGAGCCTGTCCATC 126
127 ACTTGCACTGTCTCTGGGTTTTCATTAACCAAGTATGGTGTACACTGGGTTCGCCAGCCT 186
187 CCAGGAAAGGGTCTGGAGTGGCTGGGAGTAATATGGGCTGGTGGAAACACAAATTATAAT 246
247 TCAGCTCTCATGTCCAGACTGAGCATCAGCAAAGACAATTCCAAGAGCCAAGTTTTCTTA 306
307 AAAATGAACAGTCTGCAAATTGATGACACAGCCATATACTACTGTGCCAAAC 358
359 ---------------- 375
376 TACTATGCTATGGACTATTGGGGTCAAGGAACCTCAGTCACCGTCTCCTCA 426
```

>gb|M34626|MUSIGHACK Mouse Ig rearranged heavy chain (HC19-F8) mRNA VH-DH-JH4

```
  1 CAGGTGCAGCTGAAGGAGTCAGGACCTGGCCTGGTGGCGCCCTCACAGAGCCTGTCCATC  60
 61 ACTTGCACTGTCTCTGGGTTTCCATTAACCAGCTATGGTGTAGACTGGGTTCGCCAGCCT 120
121 CCAGGAAAGGGTCTGGAGTGGCTGGGAGTAATATGGGGTGGTGGAAGCACNAATTATAAT 180
181 TCAGCTCTCATGTCCAGACTGAGCATCAGCAAAGACAACTCCAAGAGCCAAGTTTTCTTA 240
241 AAAATGAACAGTCTGCNAACTGATGACACAGCCATGTACTACTGTGCC 288
289 ------------ 299
300 ACGGGGHNTTTACTATGCTATGGACTACTGGGGTCAAGGAACCTCAGTCACCGTCTC 356
```

>gb|L31403|MUSIGHCVX Mouse immunoglobulin heavy chain variable region (Igh-V)

```
 58 CAGGTGCACCTGAAGGAGTCAGGACCTGGCCTGGTGGCGCCCTCACAGAGCCTGTCCATC 117
118 ACTTGCACTGTCTCTGGATTTTCATTAACCACCTATGGTGTACACTGGTTTCGCCAGCCT 177
178 CCAGGAAAGGGTCTGGAGTGGCTGGGACTAATATGGGCTGGTGGAAACACAGATTATAAT 237
238 TCGGCTCTCATGTCCAGACTGAGCATCAACAAAGACAACTCCAAGAGCCAAGTTTTCTTA 297
298 AAAATGAACAGTCTGCAAGCTGATGACACAGCCATGTACTACTGTGCCAGATT 350
351 ---------------- 367
368 ACGACTATGCTGTGGACTACTGGGGTCAAGGAACCTCAGTCACCGTCTCCTCA 420
```

MONOCLONAL ANTIBODY 1A7 AND USE FOR THE TREATMENT OF MELANOMA AND SMALL CELL CARCINOMA

CROSS REFERENCE TO RELATED APPLICATIONS

This application is a continuation of U.S. Ser. No. 10/153,401, filed May 21, 2002, which is a continuation of U.S. Ser. No. 09/293,533, filed on Apr. 15, 1999, issued as U.S. Pat. No. 6,509,016, which is a continuation of U.S. Ser. No. 08/752,844, file on Nov. 21, 1996, issued as U.S. Pat. No. 5,935,821, which is a continuation-in-part of U.S. Ser. No. 08/372,676, filed Jan. 17, 1995, issued as U.S. Pat. No. 5,612,030; and U.S. Ser. No. 08/591,196, filed Jan. 16, 1996; issued as U.S. Pat. No. 5,977,316; both of which are hereby incorporated herein in their entirety.

STATEMENT OF RIGHTS TO INVENTIONS MADE UNDER FEDERALLY SPONSORED RESEARCH

This invention was made in part during work supported by a grant from the United States Public Health Service (CA72018). The government has certain rights in the invention

BACKGROUND

In spite of numerous advances in medical research, cancer remains the second leading cause of death in the United States. Traditional modes of clinical care, such as surgical resection, radiotherapy and chemotherapy, have a significant failure rate, especially for solid tumors. Failure occurs either because the initial tumor is unresponsive, or because of recurrence due to regrowth at the original site or metastasis. Cancer remains a central focus for medical research and development.

Under the hypothesis that neoplastic cells are normally regulated by immune surveillance, an attractive approach is to re-focus the immune system in affected individuals back towards the tumor. Many types of cancers should be susceptible to the immune system, because they express unusual antigens that reflect the oncogenic transformation of the cell. Antibodies or T cells directed against a target antigen specifically expressed on tumor cells may be able to recruit immune effector functions, and thereby eliminate the tumor or mitigate the pathological consequences.

There are several potential pitfalls in this approach. The first is that the target tumor antigen may be shed from the cell, and thereby block the approach of tumor-specific immune components. The second is that the expression of the target antigen may be heterologous. In this case, a specific immune response would be ineffective in a substantial subclass of affected individuals, or the risk of escape variants would be high The third difficulty is that tumor-specific antigens are generally-antigenically related to autoantigens, or comprise autoantigens in an atypical mode of expression. This means that tumor-associated antigens are often poorly immunogenic; perhaps due to an active and ongoing immunosuppression against them. Furthermore, cancer patients tend to be immunosuppressed, and only respond to certain T-dependent antigens.

A number of features suggest that gangliosides may be preferable to other types of target antigens for antibody-mediated killing of certain tumor types. Gangliosides like GD2 have simple, well-defined structures, and the level of expression is not affected by antibody binding. In vitro studies have shown that monoclonal antibodies against gangliosides like GD2 and GD3 potentiate lymphocyte response which could potentially be directed towards tumor cells. In addition, certain gangliosides have been implicated in the adhesion of tumor cells to solid substrates, and antibodies inhibit this attachment. An immune response against them, even if not successful in eliminating the tumor cells, could reduce the extent of pathology.

In particular, glycosphingolipid GD2 is expressed at high density by tumors of human neuroectodermal origin; including malignant melanoma, neuroblastoma, glioma, soft tissue sarcoma and small cell carcinoma of the lung. The GD2 antigen is absent in most normal tissues, except for low levels in brain and peripheral nerve.

Melanoma is one of the human diseases for which there is an acute need of new therapeutic modalities. It is a particularly aggressive form of skin cancer, and occurs in increased frequency in individuals with regular unguarded sun exposure. In the early phases, melanoma is characterized by proliferation at the dermal-epidermal junction, which soon invades adjacent tissue and metastasizes widely. Worldwide, 70,000 patients are diagnosed and 25,000 deaths are reported each year. The American Cancer Society projects that by the year 2000, 1 out of every 75 Americans will be diagnosed with melanoma in their lifetime.

Fortunately, melanoma is one of the cancers for which gangliosides hold significant promise as a target antigen Livingston (1995) Immunol. Rev. 145:147-166). Increased expression of GD2 has been observed in a majority of malignant melanoma cells. Several murine monoclonal anti-GD2 antibodies were reported to suppress the growth of tumors of neuroectodermal origin in athymic (nu/nu) mice or cause remission in patients with metastatic melanoma. A human-mouse chimeric anti-GD2 antibody remissions in patients with metastatic neuroblastoma. The mechanism is thought to involve antibody dependent cellular cytotoxicity (ADCC) or complement-mediated cytotoxicity (CMC). Clinical responses have been obtained by treating with monoclonal antibodies against GM2, GD2 and GD3. Active immunization with a ganglioside vaccine comprising GM2 produced anti-GM2 antibodies in 50/58 patients, who survived longer on average than antibody negative patients.

Neuroblastoma is a highly malignant tumor occurring during infancy and early childhood. Except for Wilm's tumor, it is the most common retroperitoneal tumor in children. This tumor metastasizes early, with widespread involvement of lymph nodes, liver, bone, lung, and marrow. While the primary tumor is resolvable by resection, the recurrence rate is high.

Small cell lung cancer is the most malignant and fastest growing form of lung cancer. It accounts for 20-25% of new cases of lung cancer, and 60,000 cases will be diagnosed in the US in 1996. The primary tumor is generally responsive to chemotherapy, but is shortly followed by wide-spread metastasis. The median survival time at diagnosis is ~1 year, with a 5 year survival rate of only 5-10%.

If there was a simple and reliable therapeutic strategy for providing immune reactivity against GD2, then the clinical prospects for these types of cancers might improve.

Unfortunately, there are several reasons why GD2 is less than ideal as a component of an active vaccine. For one thing, GD2 is of limited supply, and is difficult to purify. Of course, because GD2 is a ganglioside, it cannot be generated by simple recombinant techniques. Secondly, gangliosides in general and GD2 in particular, are poorly immunogenic. In order to render them more immunogenic in humans, it has been necessary to conjugate them to protein carriers like KLH (U.S. Pat. No. 5,308,614; WO 94/16731).

Similarly, the passive administration of anti-GD2 antibodies is less than ideal as an approach to long-term care. The amount of antibody that must be provided passively is substantial. It may lead to the formation of anti-immunoglobulin or anti-idiotype, which in turn may lead to diminished responsiveness with each succeeding dose. And perhaps most importantly, it fails to provide the host with components of the immune response which may be critical in tumor eradication; particularly tumor-directed cytotoxic T cells.

How else, then, could an active immune response against GD2 be obtained? The network hypothesis of Lindemann and Jerne suggests a way of overcoming both the natural immune tolerance against GD2, and the shortage of supply of GD2. It relies on the fact that antibodies comprise variable region epitopes that themselves may be immunogenic, leading to the generation of second-level antibodies called anti-idiotypes. According to the hypothesis, immunization with a given tumor-associated antigen will generate production of antibodies against this tumor-associated antigen (Ab1), which is purified and used in a second round of immunization to generate the anti-idiotype (Ab2). Some of these Ab2 molecules (called Ab2β) fit into the paratopes of Ab1, and can be used as surrogate tumor-associated antigens. Thus, immunization with Ab20β can lead to the generation of anti-anti-idiotype antibodies (Ab3) that recognize the corresponding original tumor-associated antigen identified by Ab1. The idea is that the Ab2 presents a feature that is structurally related to the tumor antigen in a different context that makes it more immunogenic.

Accordingly, efforts have been made elsewhere using anti-idiotypes to elicit a response against various tumor-associated antigens. One group of investigators raised an anti-idiotype related to the melanoma associated ganglioside $GM_3$ (Kanda et al., Yamamoto et al., Hastings et al.). Saleh et al. and Cheung et al. have raised anti-idiotypes against GD2. Other anti-idiotypes have entered early clinical trials: for example, Mittelman et al. are using an anti-idiotype related to a high molecular weight melanoma associated antigen (MAA). Chattopadhyay et al. have developed anti-idiotypes against a melanoma-associated proteoglycan. Chapman et al are treating melanoma patients with an anti-idiotype related to ganglioside GD3. Most of these trials are still at about the phase I level with results still pending.

It is important to emphasize that every potential anti-idiotype for use in tumor therapy must be evaluated on a case-by-case basis. First, only a fraction of antibodies raised against an Ab1 are limited in their reactivity against the paratope of the Ab1 (i.e., non-reactive against features shared with other potential antibodies in the host individual). Second, anti-idiotypes are not necessarily immunogenic. Third, only a fraction of immunogenic anti-idiotypes elicit a response against the original tumor antigen and not against other antigens with less tissue specificity. These properties are related to the structure of the anti-idiotype, including the amino acid sequence of its variable regions. Different anti-idiotypes raised against the same Ab1 will be different in this respect, and must be evaluated separately. Furthermore, the anti-tumor response elicited will depend on the immunological status of the individual being immunized.

SUMMARY OF THE INVENTION

This disclosure outlines a particular monoclonal anti-idiotype antibody, designated 1A7. This antibody has been established as being capable of eliciting an anti-GD2 response. It has all the desirable properties that provide for escaping immune tolerance to GD2, and is appropriate for treating GD2-associated disease.

Also described are a number of other compounds derived from 1A7. These include in particular polynucleotides and polypeptides based on the 1A7 heavy and light chain variable regions, distinguish 1A7 from other immunoglobulin molecules. A wide range of such products are contemplated. Preferred derivative compounds include a humanized version of intact 1A7, polypeptide fragments from the complementarity determining regions of the 1A7 heavy chain, and a vaccinia virus vector comprising an encoding region for a 1A7 variable region. Especially preferred compounds include a 1A7 antibody fusion molecule comprising a polypeptide region with GM-CSF or IL-2 attached to the heavy chain constant region, a single-chain $V_H$-$V_L$ or $V_L$-$V_H$ variable region, and polynucleotides encoding such polypeptides.

The compounds and compositions of this invention may be used inter alia for eliciting a humoral or cellular immune response in an individual. They may be used for detecting or treating a GD-2 associated disease; including therapy of advanced disease, and prophylactic care, particularly for decreasing the risk of recurrence in an adjuvant setting.

Accordingly, this invention embodies monoclonal antibody 1A7, and a hybridoma cell line that produces it Also included are antibodies having identifying characteristics of 1A7.

Another embodiment of this invention is a polynucleotide comprising a sequence encoding a polypeptide with immunological activity of monoclonal antibody 1A7, wherein the polypeptide comprises at least 5 consecutive amino acids from a variable region of monoclonal antibody 1A7. The variable region may be from either the 1A7 light chain or heavy chain. The 5 consecutive amino acids preferably play a role in 1A7 immunologic reactivity, and may be from a complementarity determining region. Another embodiment is an isolated polynucleotide of at least 20 consecutive nucleotides capable of forming a stable duplex with the 1A7 light or heavy chain encoding sequence, but not with encoded sequences for other previously described immunoglobulin molecules. Any of these polynucleotides may be in the form of cloning vectors, expression vectors, or transfected into host cells.

Also embodied is a polypeptide having immunological activity of monoclonal antibody 1A7, wherein the polypeptide comprises at least 5 consecutive amino acids from a variable region of monoclonal antibody 1A7. The variable region may be from a light chain or heavy chain. The 5 consecutive amino acids preferably play a role in 1A7 immunologic reactivity, and may be from a complementarity dewing region. Intact 1A7, functionally active fragments of 1A7, fusion proteins, humanized antibodies, multiple antigen proteins, and other polypeptide derivatives of 1A7 are included. Of special interest are single-chain variable regions and fusion proteins comprising a cytokine.

Another embodiment is a pharmaceutical composition or vaccine, comprising monoclonal antibody 1A7, a polynucleotide of this invention, or a polypeptide of this invention, and a pharmaceutically acceptable excipient.

A further embodiment of this invention is a method of eliciting an immune response in an individual comprising administering to the individual an effective amount of monoclonal antibody 1A7, or a polynucleotide or polypeptide of this invention. The immune response may comprise either humoral or cellular immunity, preferably both.

Yet another embodiment is a method of treating a GD2-associated disease in an individual, comprising administering monoclonal antibody 1A7, or a polynucleotide or polypeptide of this invention. The disease may be melanoma, neuroblastoma, glioma, soft tissue sarcoma, and small cell carcinoma. The individual may have a clinically detectable tumor, or the tumor may have been previously treated and rendered undetectable. The method may be for palliating the disease, or for reducing the risk of recurrence.

A further embodiment of this invention is a kit for detection or quantitation of an anti-GD2 antibody or a 1A7 polynucleotide in a sample, comprising monoclonal antibody 1A7 or a polynucleotide or polypeptide of this invention in suitable packaging. Also embodied are methods for detecting such antibodies or polynucleotides by employing a reagent or kit embodied in this invention.

BRIEF DESCRIPTION OF THE FIGURES

FIG. 1 is a depiction of the cDNA sequence (SEQ ID NO:1) and the amino acid sequence (SEQ ID NO:2) of the light chain variable region of 1A7 and adjoining residues.

FIG. 2 is a depiction of the cDNA sequence (SEQ ID NO:3) and the amino acid sequence (SEQ ID NO:4) of the heavy chain variable region of 1A7 and adjoining residues.

FIG. 3 is a listing in which the amino acid sequences of the 1A7 variable region are compared with 15 light and heavy chain immunoglobulin sequences from the prior art Panel A (amino acids 1 through 112 of SEQ. ID NO:2) shows the light chain comparison; Panel B (SEQ. ID NOS:5-14) shows the heavy chain comparison. Panel C shows variable region consensus sequences for the light and heavy chains (SEQ. ID NOS:15-16), and compares them with those of 1A7. The variable region of 1A7 shows splicing differences about the VDJ junction of the heavy chain, and an additional 16 point differences.

FIG. 12 is two bar graphs depicting the character of Ab3 antibody purified from the sera of human patients treated with antibody 1A7. Upper panel shows that the Ab3 response comprises specific antibody to ganglioside GD2 (hatched bars) but not GD3 (solid bars). Lower panel shows that the anti-GD2 response is predominantly IgG (hatched bars) rather than IgM (solid bars).

FIG. 13 is two graphs further cha ng purified Ab3 from three human patients. The induced Ab3 inhibits the binding of anti-GD2 to purified ganglioside GD2 (upper panel) or a GD2 expressing cancer cell line (lower panel) in a dose-dependent fashion.

FIG. 15 is a listing of the nucleotide sequence (SEQ. ID NO:65) and amino acid translation (SEQ. ID NO:66) for a single-chain variable region molecule (scFv), developed from the variable region sequences of intact monoclonal antibody 1A7.

FIG. 17 depicts the 10 polynucleotide sequences that were most closely matched to the 1A7 light chain variable region encoding sequence in a database search. These sequences have the designations SEQ. ID NOS:17-26.

FIG. 18 depicts the 10 polynucleotide sequences that were most closely matched to the 1A7 heavy chain variable region encoding sequence in a database search. These sequences have the designations SEQ. ID NOS:27-44.

DETAILED DESCRIPTION

Figure 4:
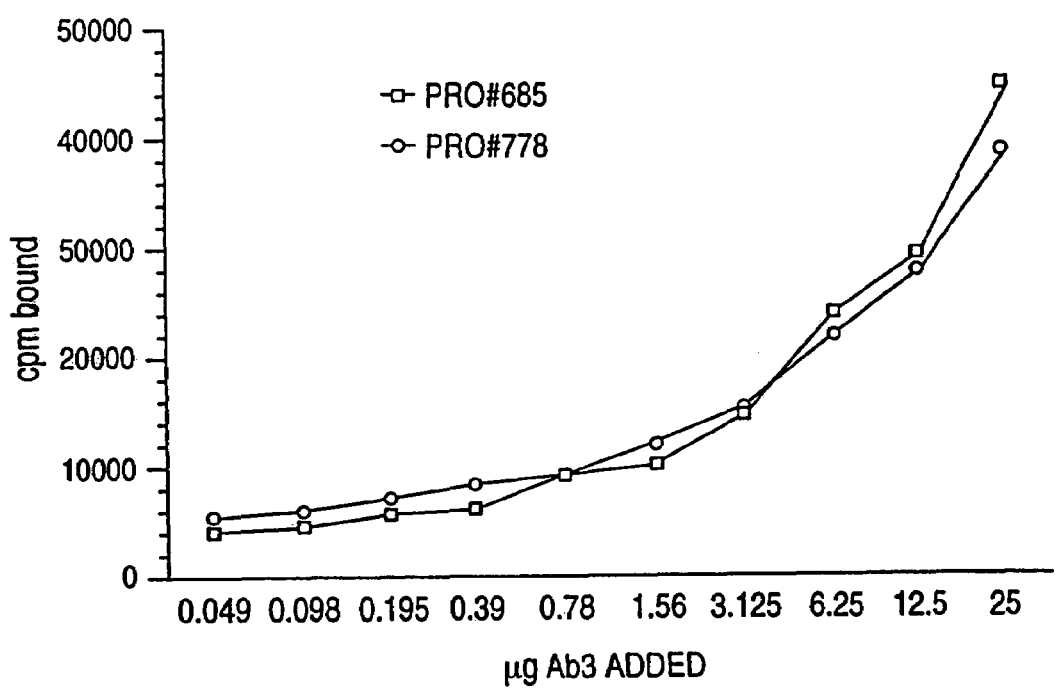
FIG. 4 is a graph depicting the binding of monkey. Ab3 to Ab2 (1A7) by sandwich radioimmunoassay. Open squares denote Ab3 from monkey PRO#685; open circles denote Ab3 from monkey PRO#778.

This invention relates to the discovery of an anti-idiotype antibody that is capable of recruiting a tumor-specific response against GD2. The antibody is designated 1A7. The immune response elicited by 1A7 typically comprises both humoral and cellular components, and is therefore expected to be useful in palliating the clinical conditions related to GD2-associated tumors. The invention comprises the 1A7 antibody molecule, along with polynucleotide and polypeptide derivatives thereof, and methods for using these compounds in diagnosis and treatment.

Cancer patients are typically tolerized to various tumor associated antigens (TAA), including GD2. 1A7 successfully circumvents immune tolerance, and elicits an immune response against GD2. According to the network theory Ab1 represents anti-tumor monoclonal antibody; Ab2 represents anti-idiotypic monoclonal antibody; and Ab3 represents anti-anti-idiotypic monoclonal antibody. 1A7 is an Ab2 that stimulates Ab3 with the same specificity as Ab1, and can therefore recruit effector functions against tumors bearing the tumor antigen. An Ab3 response reactive against the original TAA is referred to herein as Ab1'.

While not wishing to be bound by theory, one explanation is that the 1A7 combining site may present a region that at least partly resembles an epitope in GD2 in the context of one or more other epitopes which render it more immunogenic. The epitope of GD2 which may resemble that of 1A7 is identified by the Ab1 (14G2a) used to generate 1A7. As a result, 1A7 escapes the normal immune tolerance against GD2, and is able to elicit an anti-GD2 response.

FIGS. 1 and 2 show the nucleotide encoding region of the 1A7 light and heavy chain variable regions, respectively, along with the corresponding amino acid translation. These sequences were compared with those of other known immunoglobulin molecules (Example 2). Both the polynucleotide and polypeptide variable region sequences for 1A7 are unique.

Amongst the 50 database sequences matched most closely to that of the 1A7 light chain variable region, none was identical 1A7 differed from the five closest sequences by 2 substitution differences at residues 50 and 55, which are contained in the second CDR. The two differences at these positions were non-conservative substitutions, and persisted in comparisons with other light chain sequences.

Amongst the 50 database sequences matched most closely to that of the 1A7 heavy chain variable region, none was identical FIG. 3, Panels A and B). The following summarizes the main points deduced from the comparison.

The closest match was with a heavy chain fragment. There were 2 deletions and 12 substitution differences.

The closest match with a full length heavy chain variable region had the following features: There were 3 deletions and 17 substitution differences 1A7 differed in length from all sequences but one, due to insertions or deletions of 1 to 8 residues about the VDJ junction. For the sequence of equal length, there were 26 substitution differences.

All other comparisons showed a total of at least 22 insertions, deletions and substitution differences. Differences appeared throughout the variable region.

FIG. 3 Panel C provides a comparison of the 1A7 amino acid light and heavy chain sequences with consensus sequences derived from the database sequences. Other than splicing differences about the heavy chain VDJ junction, there appear to be about 16 differences between 1A7' and the consensus sequences that have likely arisen from somatic mutation during antibody maturation.

Particularly of interest in developing 1A7 derivatives with 1A7 immunologic activity are regions of the polynucleotide or polypeptide sequence comprising part of the VDJ junction. Also of interest are regions spanning at least one, preferably 2, and more preferably 3 or more of the point differences between the 1A7 amino acid sequences and the consensus sequences.

The full sequences of the 1A7 light and heavy chain constant regions have not been determined, but are expected to be identical or nearly identical to those of other mouse immunoglobulin molecules.

For the mouse kappa light chain constant region, four genetic allotypes encoding two protein allotypes have been published by Solin et al. (1993) Immunogenetics 37:401-407, which is hereby incorporated herein by reference. FIG. 1 of Solin et al. depicts mouse and rat immunoglobulin kappa chain gene sequences, comparing the sequences within the kappa chain constant region for different strains and highlighting allotypic differences. Included are kappa chain constant region sequences for BALB/c, PL, SJL, and *M spretus*. Other naturally occurring allotypes are possible.

Figure 5:
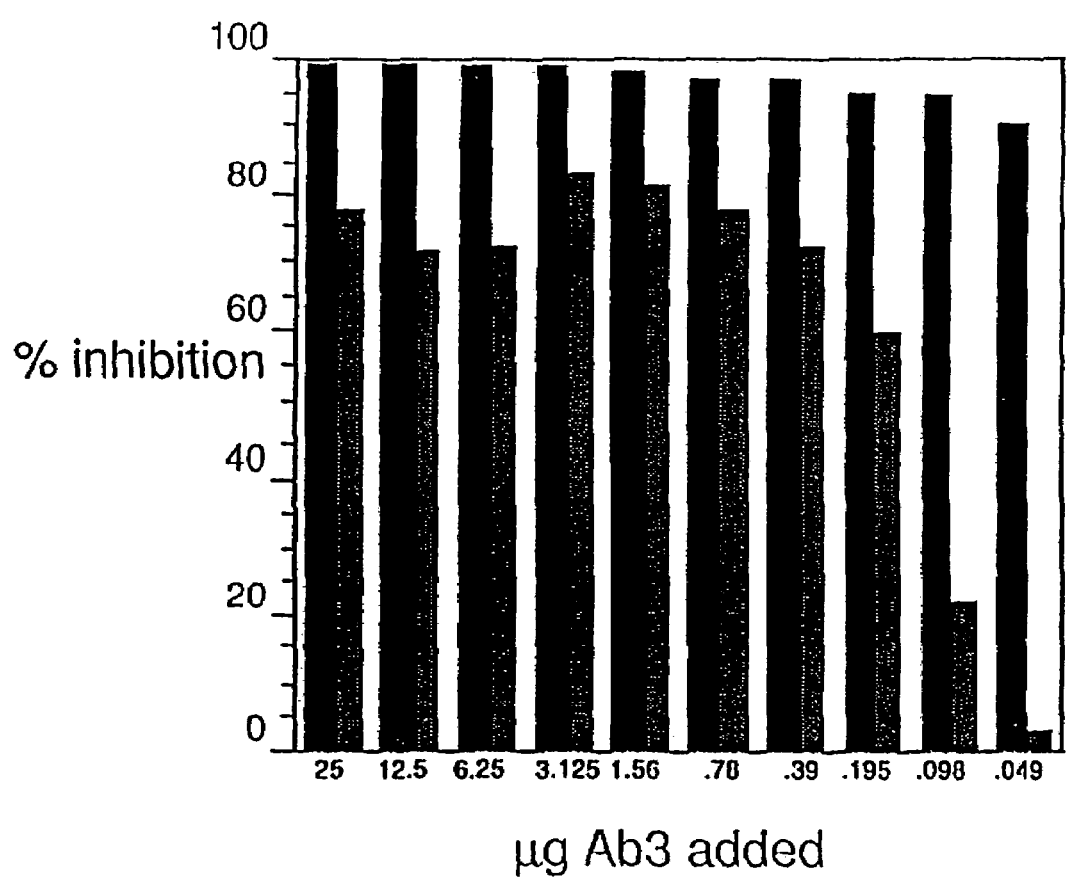
FIG. 5 is a bar graph depicting inhibition of Ab1-Ab2 binding by monkey Ab3 or vice-versa). For each pair of bars, the left hand bar denotes Ab2-Ab3 with labeled Ab1; the right hand bar denotes Ab1-Ab3 with labeled Ab2.

The mouse $\gamma_1$ heavy chain constant region DNA sequence from newborn mice has been published by Honjo et al. (1979) Cell 18:559-568, which is hereby incorporated herein by reference. FIG. 5 of Honjo et al. shows the germ-line DNA sequence, along with the encoded protein sequence. Shown in the line above is another protein sequence obtained from the mouse myeloma MOPC 21. Other naturally occurring allotypes are possible.

The 1A7 antibody and derivatives thereof are useful, for example, for eliciting an anti-GD2 immune response, for treating a GD2-associated disease, and as reagents for detecting the presence of anti GD2.

Certain compounds, compositions and methods described in this application relate generally to 1A7 and derivatives thereof which are routinely generated by classical techniques of immunochemistry. This includes 1A7 which has been coupled to another compound by chemical conjugation, or by mixing with an excipient or an adjuvant It includes such immunoglobulin fragments as Fab, $F(ab')_2$, Fab', and isolated heavy and light chains. First generation therapies are those based on such compounds and compositions.

Other compounds, compositions and method described in this application relate to polynucleotide and polypeptide derivatives of 1A7 that fall outside the preceding classification. The compositions are typically generated by genetic engineering, although they may alternatively be obtained by other methods and combinations of methods. This classification includes (but is not limited to) isolated polynucleotide fragments, recombinant polynucleotides, engineered peptide fragments and fusion peptides, and polynucleotides or polypeptides prepared by chemical synthesis based on the sequence data. Preferred compounds include polypeptide fragments of the 1A7 CDRs, antibody fusion proteins comprising cytokine effector components, single-chain variable region proteins and the polynucleotides encoding them, therapeutic plasmids comprising 1A7 polynucleotides, and vectors such as vaccinia vectors.

Unless explicitly stated otherwise or required by their nate, methods of making or using certain compounds embodied in this invention may be applied to other compounds of this invention, as appropriate.

Pharmaceutical compositions and treatment modalities of this invention may be brought to bear whenever it is desirable to elicit a response against GD2, especially in humans. Human patients with GD2-associated tumors, including melanoma, neuroblastoma, glioma, soft tissue sarcoma, and small cell carcinoma (including small cell lung cancer) are especially appropriate subjects. The subjects may have an advanced form of disease, in which case the objective may include mitigation or reversal of disease progression, and amelioration of side effects. The subjects may have had a history of the condition, for which they have already been treated, in which case the objective will typically include a decrease or delay in the risk of recurrence of clinical pathology.

Additionally, the antibodies and derivatives of this invention may also be used as probes, primers, and polypeptides for use as diagnostic reagents. These applications are described in more detail in the sections that follow.

Definitions

"1A7" is a particular anti-idiotype antibody raised against the anti-GD2 monoclonal antibody with the designation 14G2a. The generation and characterization of 1A7 is described in Example 1.

"Immunological activity" of 1A7 refers to any of the following activities: ability to specifically bind monoclonal antibody 14G2a; ability to inhibit the binding of 1A7 to 14G2a or 14G2a to GD2 in a specific manner, and an ability to elicit an immune response against GD2. A specific immune response may comprise antibody, B cells, T cells, and any combination thereof, and effector functions resulting therefrom. Included are the antibody-mediated functions ADCC and complement-mediated cytolysis (CMC). The T cell response includes T helper cell function, cytotoxic T cell function, inflammation/inducer T cell function, and T cell mediated suppression. A compound able to elicit a specific immune response according to any of these criteria is referred to as "immunogenic".

1A7 "activity" or "function" refers to any of the immunological activities of 1A7, or to any other biological activity ascribed to 1A7 in this disclosure, including the role of 1A7 in the amelioration or palliation of GD2-associated disease.

The "variable region" of 1A7 refers to the variable region of the 1A7 light chain or the variable region of the 1A7 heavy chain, either alone or in combination, and includes amino acids encoded by the V, D, and J encoding regions of the respective gene, as appropriate.

GM-CSF, IL 2, and other biologically active molecules referred to herein are meant to include fragments and derivatives based on the respective parent molecule that have the same biologic or physiologic function.

A "polynucleotide" is a polymeric form of nucleotides of any length, which contain deoxyribonucleotides, ribonucleotides, and analogs in any combination analogs. Polynucleotides may have any three-dimensional structure, and may perform any function, known or unknown. The term "polynucleotide" includes double-, single-stranded, and triple-helical molecules. Unless otherwise specified or required, any embodiment of the invention described herein that is a polynucleotide encompasses both the double-stranded form and each of two complementary single-stranded forms known or predicted to make up the double stranded form.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching to proteins, metal ions, labeling components, other polynucleotides, or a solid support.

The term "recombinant" polynucleotide as used herein intends a polynucleotide of genomic, cDNA, semisynthetic, or synthetic origin which either does not occur in nature or is linked to another polynucleotide in an arrangement not found in nature.

The terms "polypeptide", "peptide" and "protein" are used interchangeably herein to refer to polymers of amino acids of any length. The polymer may be linear or branched, it may comprise modified amino acids or amino acid analogs, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Unless stated or implied otherwise, the term 1A7 polypeptide includes any polypeptide monomer or polymer with 1A7 activity, including the intact 1A7 antibody, and smaller and larger functionally equivalent polypeptides, as described herein.

A "fusion polypeptide" is a polypeptide comprising regions in a different position in the sequence than occurs in nature. The regions may normally exist in separate proteins and are brought together in the fusion polypeptide; or they may normally exist in the same protein but are pieced in a new arrangement in the fusion polypeptide.

A "functionally equivalent fragment" of a 1A7 polypeptide or polynucleotide varies from the native sequence by any combination of additions deletions, or substitutions while preserving at least one functional property of the fragment relevant to the context in which it is being used. A functionally equivalent fragment of a 1A7 polynucleotide either encodes a polypeptide that is functionally equivalent to 1A7 when used in an expression system, or has similar hybridization specificity as a 1A7 polynucleotide when used in a hybridization assay. A functionally equivalent fragment of a 1A7 polypeptide typically has one or more of the following properties: ability to bind monoclonal antibody 14G2 ab ability to inhibit the binding of 1A7 to 14G2a or 14G2a to GD2 in a specific manner, and an ability to elicit an immune response with a similar antigen specificity as that elicited by 1A7.

A "cell line" or "cell culture" denotes higher eukaryotic cells gown or maintained in vitro. It is understood that the descendants of a cell may not be completely identical (either morphologically, genotypically, or phenotypically) to the parent cell.

A "vector" refers to a recombinant DNA or RNA plasmid or virus that comprises a heterologous polynucleotide to be delivered into a target cell, either in vitro or in vivo. The heterologous polynucleotide may comprise a sequence of interest for purposes of therapy, and may optionally be in the form of an expression cassette. As used herein, a vector need not be capable of replication in the ultimate target cell or subject. The term includes cloning vectors for the replication of a polynucleotide, and expression vectors for translation of a polynucleotide encoding sequence. Also included are viral vectors, which comprise a polynucleotide encapsidated or enveloped in a viral particle.

A "host cell" denotes a eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

"Heterologous" means derived from a genotypically distinct entity from the rest of the entity to which it is being compared For example, a polynucleotide may be placed by genetic engineering techniques into a plasmid or vector derived from a different source, and is a heterologous polynucleotide. A promoter removed from its native coding sequence and operatively linked to a coding sequence with which it is not naturally found linked is a heterologous promoter.

A "signal sequence" or "leader sequence" is a short amino acid sequence that directs a newly synthesized secretory or membrane protein through a cellular membrane, usually the endoplasmic reticulum. Signal sequences are typically in the N-terminal portion of a polypeptide and are typically removed between biosynthesis and secretion of the polypeptide from the cell.

An "isolated" polynucleotide or polypeptide is one that is substantially free of the materials with which it is associated in nature. By substantially free is meant at least 50%, preferably at least 70%, more preferably at least 80%, and even more preferably at least 90% free of the materials with which it is associated in nature.

A "stable duplex" of polynucleotides, or a "stable complex" formed between any two or more components in a biochemical reaction, refers to a duplex or complex that is sufficiently long-lasting to persist between the formation of the duplex or complex and subsequent detection, including any optional washing steps or other manipulation that may take place in the interim.

A "biological sample" encompasses a variety of sample types, including blood and other liquid samples of biological origin, solid tissue samples such as a biopsy specimen or tissue cultures, or cells derived therefrom and the progeny thereof. The definition also includes samples that have been manipulated in any way after their procurement, such as by treatment with reagents, solubilization, or enrichment for certain components, such as proteins or polynucleotides. The term encompasses various kinds of clinical samples obtained from any species, and also includes cells in culture, cell supernatants, and cell lysates.

A "vaccine" is a pharmaceutical composition for human or animal use, which is administered with the intention of conferring the recipient with a degree of specific immunological reactivity against a particular target, or group of targets. The immunological reactivity may be antibodies or cells (particularly B cells, plasma cells, T helper cells, and cytotoxic T lymphocytes, and their precursors) that are immunologically reactive against the target, or any combination thereof. For purposes of this invention, the target is primarily tumor associated antigen GD2, but also includes any tumor associated antigen bound by 14G2a. The immunological reactivity may be desired for experimental purposes, for treatment of a particular condition, for the elimination of a particular substance, or for prophylaxis. An active vaccine is a vaccine intended to elicit an immune response in the recipient that persists in the absence of the vaccine components.

"Adjuvant" as used herein has two meanings, depending on the context in which it is used. In the context of a pharmaceutical preparation, an adjuvant is a chemical or biological agent given in combination with an antibody, polynucleotide or polypeptide to enhance its immunogenicity. In the context of cancer diagnosis or management, it refers to a class of subjects with no clinically detectable tumor mass, but who are suspected of being at risk of recurrence because of a history of cancer.

When referring to a type of cancer that normally manifests as a solid tumor, a "clinically detectable" tumor is one that is detectable on the basis of tumor mass; i.e., by such procedures as CAT scan, X-ray, or palpation. Positive biochemical, histological or immunological findings on their own are insufficient to meet this definition.

As used herein, "treatment" refers to clinical intervention in an attempt to alter the natural course of the individual or cell being treated, and may be performed either for prophylaxis or during the course of clinical pathology. Desirable effects include preventing occurrence or recurrence of disease, alleviation of symptoms, diminishment of any direct or indirect pathological consequences of the disease, preventing metastasis, lowering the rate of disease progression, amelioration or palliation of the disease state, and remission or improved prognosis.

The "pathology" associated with a disease condition is anything that compromises the well-being, normal physiology, or quality of life of the affected individual. This may involve (but is not limited to) destructive invasion of affected tissues into previously unaffected areas, growth at the expense of normal tissue function, irregular or suppressed biological activity, aggravation or suppression of an inflammatory or immunological response, increased susceptibility to other pathogenic organisms or agents, and undesirable clinical symptoms such as pain, fever, nausea, fatigue, mood alterations, and such other features as may be determined by an attending physician.

An "effective amount" is an amount sufficient to effect a beneficial or desired clinical result. An effective amount can be administered in one or more doses. For purposes of this invention, an effective amount of a 1A7 polynucleotide or polypeptide is an amount that induces an immune response, particularly an anti-GD2 response. In terms of treatment, an effective amount is amount that is sufficient to palliate, ameliorate, stabilize, reverse or slow the progression of the GD2-associated disease, or otherwise reduce the pathological consequences of the disease.

An "individual" is a vertebrate, preferably a mammal, more preferably a human. Mammals include, but are not limited to, farm animals, sport animals, and pets.

General Techniques

The practice of the present invention will employ, unless otherwise indicated, conventional techniques of molecular biology (including-recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); "Current Protocols in Immunology" (J. E. Coligan et al., eds., 1991).

All patents, patent applications, articles and publications mentioned herein, both supra and infra, are hereby incorporated herein by reference.

These techniques are applicable to the production of the polynucleotides and polypeptides of the invention, and, as such, may be considered in making and practicing the invention. Particularly useful techniques for particular embodiments will be discussed in the sections that follow.

How Monoclonal Antibody 1A7 was Generated and Selected

1A7 was obtained by immunizing naive mice with 14G2a anti-GD2 antibody to obtain an anti-idiotype response. 14G2a binds to a unique epitope of GD2. Syngeneic BALB/c mice-were immunized four times with 14G2a (Ab1) and their spleen cells were fused with the non-secretory mouse myeloma P3-653 cells.

To obtain an anti-idiotype with all the features desired, an extensive screening process was employed, comprising the following four important steps: (1) Positive selection for antibody binding to 14G2a; (2) Negative selection against antibody recognizing isotypic or allotypic determinants; (3) Positive selection for an ability to inhibit the binding of 14G2a to GD2; and (4) Positive selection for an ability to induce a humoral immune response against the original tumor-associated antigen (GD2) in both mice and rabbits.

Several anti-idiotype (Ab2) hybridomas were obtained that were specific for the idiotype components of the 14G2a immunogen, and did not react with its isotypic or allotypic determinants. To determine whether the anti-14G2a were directed against the paratope of 14G2a, the binding of radiolabeled 14G2a to the GD2-positive cell line M21/P6 was studied in the presence of varying amounts of Ab2 hybridoma culture supernatants. With as little as 5 µl of culture supernatant, three of the Ab2 tested inhibited the binding by at least 70%. 1A7 showed the highest level of inhibition. Accordingly, 1A7 was grown and purified from ascites fluid for further studies, while the others were kept in reserve.

The purified Ab2 was prepared as a vaccine and injected into naive mice and rabbits. After 4 injections, serum samples were titered for the presence of Ab3 that bound not only to the immunizing Ab2, but also to GD2. The Ab2 passing all of these screening stages was designated 1A7. Further details of the method used to obtain 1A7 are provided in Example 1.

Ab3 produced in animals immunized with 1A7 has been further characterized. The immune sera from both mice and rabbits competed with 14G2a for binding to the GD2-associated cell line M21/P6 and inhibited the binding of radioiodinated 14G2a to 1A7. This indicated that anti-anti-Id (Ab3) in mice and rabbits may share idiotopes with 14G2a and they probably bind to the same epitope as Ab1. Administration of 1A7 to non-human primates (cynomolgus monkeys) also generated a specific immune response, comprising activity against GD2 (Example 3).

The nucleic acid sequence encoding the light and heavy chain variable regions of 1A7 have also been deduced, along with the translated protein sequences (Example 2).

The invention also encompasses 1A7 conjugated to a label capable of producing a detectable signal These conjugated antibodies are useful, for example, in detection systems such as quantitation of anti-GD2 or tumor imaging. Such labels are known in the art and include, but are not limited to, radioisotopes, enzymes, fluorescent compounds, chemiluminescent compounds, and bioluminescent compounds. The labels may be covalently linked to 1A7, or conjugated to the 1A7 through a secondary reagent, such as a second antibody, protein A, or a biotin-avidin complex.

Preparation of 1A7 Antibody

The 1A7 antibody of this invention can be prepared in several ways.

It is most conveniently obtained from the hybridoma deposited with the ATCC under Accession No. HB-11786, or the progeny thereof. For example, the cells can be cultured in a suitable medium, and spent medium can be used as an antibody source. Optionally, matrix-coated channels or beads and cell co-cultures may be included to enhance growth of antibody-producing cells. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal is optionally primed for ascites production by prior administration of a suitable composition; for example, Pristane.

Alternatively, 1A7 can be chemically synthesized using sequence data and other information provided in this disclosure, in conjunction with standard methods of protein synthesis. A suitable method is the solid-phase Merrifield technique. Automated peptide synthesizers are commercially available, such as those manufactured by Applied Biosystems, Inc. (Foster City, Calif.).

1A7 may also be obtained by employing routine recombinant methods such as described in Sambrook et al. (1989). For instance, using the sequences and information provided herein, a polynucleotide encoding either the 1A7 heavy or light chain can be cloned into a suitable expression vector (which contains control sequences for transcription, such as a promoter). The expression vector is in turn introduced into a host cell. The host cell is grown under suitable conditions such that the polynucleotide is transcribed and translated into a protein. Heavy and light chains of 1A7 may be produced separately, and then combined by disulfide bond rearrangement. Alternatively, vectors with separate polynucleotides encoding each chain of 1A7, or a vector with a single polynucleotide encoding both chains as separate transcripts, may be transfected into a single host cell which may then produce and assemble the entire molecule. Preferably, the host cell is a higher eukaryotic cell that can provide the normal carbohydrate complement of the molecule. The 1A7 thus produced in the host cell can be purified using standard techniques in the art. A polynucleotide encoding 1A7 for use in the production of 1A7 by any of these methods can in turn be obtained from the hybridoma producing 1A7, or be produced synthetically or recombinantly from the DNA sequence provided herein.

Methods of antibody isolation are well known in the art See, for example, Harlow and Lane (1988) *Antibodies: A Laboratory Manual*, Cold Spring Harbor Laboratory, New York. The 1A7 antibody is a mouse immunoglobulin of the IgG1 subclass, and may be isolated by any technique suitable for immunoglobulins of this isotype. Purification methods may include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-immunoglobulin. 1A7 may also be purified on affinity columns comprising the 14G2a paratope; for example, in the form of a purified Ab1 or Ab3. Preferably, 1A7 is purified from BALB/c ascites using Protein-A-CL-SEPHAROSE™ 4B chromatography followed by chromatography on a DEAE-SEPHAROSE™ 4B ion exchange column.

If 1A7 is to be administered to an individual, it is preferably at least 80% pure, more preferably it is at least 90% pure, even more preferably it is at least 95% pure and free of pyrogens and other contaminants. In this context, the percent purity is calculated as a weight percent of the total protein content of the preparation, and does not include constituents which are deliberately added to the composition after the 1A7 is purified.

Uses of 1A7 Antibody

The 1A7 antibody may be used for a number of purposes. These include eliciting an antibody response to 1A7 or GD2, eliciting a T cell response to 1A7 or GD2, and treating various types of cancer. These uses are elaborated more fully in a later section.

1A7 may also be used to purify anti-1A7 (Ab3), anti-GD2 (Ab1'), or 14G2a (Ab1). The method comprises contacting a biological sample containing the antibody with a 1A7 polypeptide, producing a complex, and recovering the Ab3 or Ab1 from the complex. Typically, the 1A7 polypeptide is coupled to an affinity matrix for affinity column purification. Such methods are routine in the art and need not be described in detail herein.

The invention also encompasses methods of detecting anti-1A7 or anti-GD2 in a biological sample. Anti-OD2 is detectable whenever (like 14G2a) it cross-reacts with 1A7. Anti-GD2 with this activity may spontaneously arise during the course of a GD2-associated disease. Anti-GD2 with this activity is especially likely in individuals who have received a course of therapy with 1A7, or a derivative thereof. These methods are applicable in a clinical setting, for example, for monitoring antibody levels in an individual, as well as an industrial setting, in which commercial production of anti-1A7 or anti-GD2 is desired.

The assay methods entail coning any anti-1A7 or anti-D2 target antibody in the sample with a 1A7 antibody or polypeptide under conditions sitable to allow the formation of a stable complex between the target and the A7, and detecting any stable complex formed. The sample is suitably prepared before conducting the assay, optionally by enriching for antibody activity. When using intact 1A7, it is generally preferable to deplete the sample of any anti-mouse immunoglobulin activity that may be present. Anti-mouse immunoglobulin antibody can be removed from a sample, for example, by precipitation with normal mouse IgG or adsorption with a mouse Ig adsorbant. Binding of anti-mouse immunoglobulin antibody, particularly that specific for the Fc region, can be minimized by judicious choice of the reagents of the assay. F(ab')$_2$ or Fab fragments of 1A7 and other reagents with fewer mouse determinants are appropriate.

After the sample is suitably prepared, it is mixed with a excess functional equivalent of 1A7 under conditions that permit formation of a complex between 1A7 and any target antibody that may be present. The amount of complex is then determined, and compared with complexes formed with standard samples containing known amounts of target antibody in the range expected. Complex formation may be observed by immunoprecipitation or nephelometry, but it is generally more sensitive to employ a reagent labeled with such labels as radioisotopes like $^{125}I$, enzymes like peroxidase and β-galactosidase, or fluorochromes like fluorescein.

Antibody assays may be conducted entirely in fluid phase. For example, anti-GD2 may be mixed with labeled 1A7. Alternatively, the anti-GD2 in the sample may be used to compete with a labeled anti-GD2 for binding sites on 1A7. Generally, bound and unbound label is separated to quantitate the percent bound. Suitable separation methods include gel filtration chromatography, and precipitation with antibody against immunoglobulin of the species from which the sample is obtained, optionally in the presence of polyethylene glycol. Alternatively, the proportion of bound and unbound label may be determined in situ, for example, using fluorescene/quench labeling pairs or enzyme/inhibitor labeling pairs. See, e.g., U.S. Pat. No. 3,996,345 (Ullman et al.).

It is generally more convenient to conduct a capture assay using a reagent linked to a solid phase, such as a polyethylene test tube, microtiter plate well, or magnetic bead. In a competition-type capture assay, unlabeled target antibody in the sample competes with a labeled analog reagent for binding to 1A7. The 1A7 may be attached directly to the solid support, or captured later, for example, using an anti-immunoglobulin. In this assay, the amount of label associated with the solid phase is inversely related to the amount of anti-GD2 in the sample.

In the sandwich-type capture assay, target antibody is captured by 1A7 attached directly or through a secondary reagent to a solid phase. After washing, the anti-GD2 is detected using anti-immunoglobulin of the appropriate species, or a second 1A7 antibody, to which a label is directly or indirectly attached. Alternatively, the anti-immunoglobulin may be attached to the solid phase and labeled 1A7 is used to complete the sandwich. If the anti-immunoglobulin used is isotype-specific, then the class of the antibody may also be determined. In this type of assay, the amount of label associated with the solid phase correlates positively with the amount of anti-GD2 in the sample. Other methods of measuring specific antibody are known in the art, and may be adapted to measure anti-1A7 or anti-GD2 by using 1A7 as the specific reagent 1A7 may also be used to measure the level of cellular anti-1A7 or anti-GD2 activity. In one example, 1A7 is used to identify anti-GD2 expressing cells in a cell suspension, perhaps B or T lymphocytes expressing a receptor that binds 1A7. 1A7 may be labeled and mixed into the cell suspension. Alternatively, unlabeled 1A7 may be mixed with the cells, and followed with a labeled secondary reagent such as labeled anti-mouse immunoglobulin or protein A. Suitable labels for this purpose include radiolabels and fluorescent labels. The use of fluorescent labels also allows anti-GD2 cells to be separated from non-specific cells in a fluorescence-activated cell sorter. In a second example, anti-GD2 expressing cells are detected in a tissue section. Typically, the tissue is fixed and embedded in a suitable medium, overlaid with 1A7, and then developed with a secondary anti-immunoglobulin coupled with a fluorescent or enzyme marker.

Polynucleotide Derivatives of 1A7

The invention provides various polynucleotides encoding the anti-idiotype antibody 1A7 or fragments of 1A7, based on the polynucleotide sequences provided herein. Various embodiments are described in this section, comprising a number of different combinations of the 1A7 heavy or light chain variable region sequences. In general, a 1A7 polynucleotide of this invention encodes at least one feature that is unique to the 1A7 molecule (in comparison with other immunoglobulins). Preferably, this feature is related in some way to an immunological reactivity of 1A7.

The invention encompasses a polynucleotide encoding a portion of the 1A7 light chain variable region, comprising at least about 70-consecutive nucleotides, preferably at least about 80 consecutive nucleotides, more preferably at least about 100 consecutive nucleotides, even more preferably at least about 150 nucleotides of SEQ ID NO:1. The invention also encompasses a polynucleotide encoding a portion of the 1A7 light chain variable region, comprising at least about 25 consecutive nucleotides, preferably at least about 30 consecutive nucleotides, even more preferably at least about 35 consecutive nucleotides of the CDR1 encoding sequence thereof. The invention also encompasses a polynucleotide encoding a portion of the 1A7 light chain variable region, comprising at least about 20 consecutive nucleotides, preferably at least about 25 consecutive nucleotides, even more preferably at least about 35 consecutive nucleotides of the CDR2 or CDR3 encoding sequence thereof.

The invention also encompasses a polynucleotide encoding a portion of the 1A7 heavy chain variable region, comprising at least about 70 consecutive nucleotides, preferably at least about 80 consecutive nucleotides, more preferably at least about 100 consecutive nucleotides, even more preferably at least about 150 nucleotides of SEQ ID NO:3. The invention also encompasses a polynucleotide encoding a portion of the 1A7 light chain variable region, comprising 15 consecutive nucleotides of the CDR1 encoding sequence thereof. The invention also encompasses a polynucleotide encoding a portion of the 1A7 light chain variable region, comprising at least about 20 consecutive nucleotides, preferably at least about 25 consecutive nucleotides, even more preferably at least about 35 consecutive nucleotides of the CDR2 or CDR3 encoding sequence thereof.

The invention includes isolated 1A7 polynucleotides encoding a polypeptide having immunological activity of 1A7, wherein the polypeptide encodes at least 5 amino acids of a variable light chain of 1A7 as depicted in SEQ. ID. NO:2.

In another embodiment, the invention includes isolated 1A7 polynucleotides encoding a polypeptide having immunological activity of 1A7, wherein the polynucleotide encodes at least 5 amino acids of a variable heavy chain of 1A7 as depicted in SEQ. ID. NO:4. The polynucleotide sequence may be similar to those depicted in SEQ ID NO:1 (FIG. 1) or SEQ ID NO:3 (FIG. 2) with changes designed to optimize codon usage, stability, or to facilitate cloning, or for some other purpose. It is within the skill of one in the art, given the amino acid sequence in SEQ ID NO:2 or SEQ ID NO:4, to design such polynucleotides. Preferred are polynucleotides encoding at least five amino acids of a 1A7 complementarity determining region (CDR).

The invention also encompasses polynucleotides encoding for functionally equivalent variants and derivatives of 1A7 and functionally equivalent figments thereof which may enhance, decrease or not significantly affect properties of the polypeptides encoded thereby. These functionally equivalent variants, derivatives, and fragments display the ability to induce an immune response, preferably an anti-GD2 immune response. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide.

The 1A7 polynucleotides of the invention may comprise additional sequences, such as additional encoding sequences within the same transcription unit, controlling elements such as promoters, ribosome binding sites, and polyadenylation sites, additional transcription units under control of the same or a different promoter, sequences that permit cloning, expression, and transformation of a host cell, and any such construct as may be desirable to provide embodiments of this invention.

The invention includes a polynucleotide of at least about 15 consecutive nucleotides, preferably at least about 20 nucleotides, more preferably at least about 25 consecutive nucleotides, more preferably at least about 35 consecutive nucleotides, more preferably at least about 50 consecutive nucleotides, even more preferably at least about 75 nucleotides, still more preferably at least about 100 nucleotides, still more preferably at least about 200 nucleotides, and even more preferably at least about 300 nucleotides that forms a stable hybrid with a polynucleotide encoding the light chain or heavy chain variable region of 1A7, but not with other immunoglobulin encoding regions known at the time of filing of this application. Any set of conditions may be used for this test, as long as at least one set of conditions exist wherein the test polynucleotide demonstrates the required specificity. Preferably, the 1A7 encoding sequences to which the test polynucleotide binds are those shown in SEQ. ID NOS:1 and 3. Since the known immunoglobulin sequences fill into a hierarchy of similarity with that of 1A7, the test may be performed by comparing the hybridization of the test polynucleotide with the 1A7 sequence with the hybridization with the most closely related sequences. Preferred is a panel of about 10 of the most closely related sequences to SEQ. ID NO:1 or 3, as appropriate. Sequences to which the test polynucleotide should not form a duplex are the light chain variable region encoding sequences listed in SEQ. ID NOS: 17-26 and the heavy chain variable region encoding sequences listed in SEQ. ID NOS:27-44.

Hybridization reactions can be performed under conditions of different "stringency". Conditions that increase stringency of a hybridization reaction are published. See, for example, Sambrook and Maniatis. Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and heir equivalent using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water.

"$T_m$" is the temperature in degrees Centigrade at which 50% of a polynucleotide duplex made of complementary strands hydrogen bonded in antiparallel direction by Watson-Crick base pairing dissociates into single strands under conditions of the experiment. $T_m$ may be predicted according to a standard formula, such as:

$$T_m = 81.5 + 16.6 \log[Na^+] + 0.41\ (\%\ G/C) - 0.61\ (\%F) - 600/L$$

where [$Na^+$] is the cation concentration (usually sodium ion) in mol/L; (% G/C) is the number of G and C residues as a percentage of total residues in the duplex; (% F) is the percent formamide in solution (wt/vol); and L is the number of nucleotides in each strand of the duplex.

Useful 1A7 polynucleotides encoding fragments of 1A7 may be identified by generating polynucleotide fragments (based on SEQ ID NO:1 or SEQ ID NO:3, for example) and testing the polypeptides encoded thereby for a function of interest. Alternatively, the polypeptide fragment encoded by a particular polynucleotide may be prepared and tested for a function of interest. Alternatively, given a 1A7 polypeptide with desirable properties, a polynucleotide could be designed that encodes it.

Included in all these embodiments are polynucleotides with encoding regions for 1A7 polymers, fusion proteins, humanized immunoglobulins, single-chain variable regions, and other particular polypeptides of interest. These polypeptides are described in a later section.

The invention also provides polynucleotides covalently linked with a detectable label. Such polynucleotides are useful, for example, as probes for detection of related nucleotide sequences.

Preparation of 1A 7 Polynucleotides:

The polynucleotides of this invention can be obtained using chemical synthesis, recombinant cloning methods, PCR, or any combination thereof.

Methods of chemical polynucleotide synthesis are well known in the art and need not be described in detail herein. One of skill in the art can use the sequence data provided herein to obtain a desired polynucleotide by employing a DNA synthesizer or ordering from a commercial service.

Alternatively, 1A7 polynucleotide sequences can be obtained from a 1A7 antibody producing cell line, 1A7 cloning vector, or 1A7 expression vector. RNA or DNA encoding the desired sequence may be isolated, amplified, and processed by standard recombinant techniques. Such techniques include digestion with restriction nucleases, and amplification by polymerase chain reaction (PCR), or a suitable combination thereof. PCR technology is described in U.S. Pat. Nos. 4,683,195, 4,800,159, 4,754,065 and 4,683,202, as well as PCR. *The Polymerase Chain Reaction*, Mullis et al. eds, Birkauswer Press, Boston (1994). A polynucleotide comprising a desired sequence can be inserted into a suitable vector, and the vector in turn can be introduced into a suitable host cell for replication and amplification. Polynucleotides may be inserted into host cells by any means known in the art. Cells are transformed by introducing an exogenous polynucleotide by direct uptake, endocytosis, transfection, f-mating or electroporation. Once introduced, the exogenous polynucleotide can be maintained within the cell as a non-integrated vector (such as a plasmid) or integrated into the host cell genome. Amplified DNA can be isolated from the host cell by standard methods: see, e.g., Sambrook et al. (1989). RNA may also be obtained from transformed host cell, it may be obtained by using an DNA-dependent RNA polymerase.

If used as a vaccine, plasmids containing 1A7 polynucleotides are preferably prepared by the method of Horn et al. ((1995) Human Gene Therapy 6:565-573), which produces a pharmaceutical grade plasmid DNA suitable for administration.

Cloning and Expression vectors Comprising a 1A7 Polynucleotide

The present invention further includes a variety of vectors comprising a 1A7 polynucleotide. These vectors can be used for expression of recombinant polypeptides as well as a source of 1A7 polynucleotides. Cloning vectors can be used to obtain replicate copies of the 1A7 polynucleotides they contain, or as a means of storing the polynucleotides in a depository for future recovery. Expression vectors (and host cells containing these expression vectors) can be used to obtain polypeptides produced from the polynucleotides they contain. They may also be used where it is desirable to express 1A7 polypeptides in an individual and thus have intact cells capable of synthesizing the polypeptide, sum as in gene therapy. Suitable cloning and expression vectors include any known in the art, e.g., those for use in bacterial, mammalian, yeast and insect expression systems. Specific vectors and suitable host cells are known in the art and need not be described in detail herein. For example, see Gacesa and Ramji *Vectors*, John Wiley & Sons (1994).

Cloning and expression vectors typically contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will grow under selective conditions. Typical selection genes either: (a) confer resistance to antibiotics or other toxins substances, e.g., ampicillin, neomycyin, methotrexate; (b) complement auxotrophic deficiencies; or (c) supply critical nutrients not available from complex media. The choice of the proper marker gene will depend on the host cell, and appropriate genes for different hosts are known in the art. Cloning and expression vectors also typically contain a replication system recognized by the host.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, or may carry genes for a marker that can be used in selecting clones containing the vector. Suitable examples include plasmids and bacterial viruses, e.g., pUC18, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen.

Expression vectors generally are replicable polynucleotide constructs that contain a polynucleotide encoding a 1A7 polypeptide of interest The polynucleotide encoding the 1A7 polypeptide is operatively linked to suitable transcriptional controlling elements, such as promoters, enhancers and terminators. For expression (i.e., translation), one or more translational controlling elements are also usually red such as ribosome binding sites, translation initiation sites, and stop codons. These controlling elements (transcriptional and translational) may be derived from the 1A7 gene, or they may be heterologous (i.e., derived from other genes or other organisms). A polynucleotide sequence encoding a signal peptide can also be included to allow a 1A7 polypeptide to cross or lodge in cell membranes or be secreted from the cell. A number of expression vectors suitable for expression in eukaryotic cells including yeast, avian, and mammalian cells are known in the art One example of an expression vector is pcDNA3 (Invitrogen, San Diego, Calif., in which transcription is driven by the cytomegalovirus (CMV) early promoter/enhancer. This vector also contains recognition sites for multiple restriction enzymes for insertion of the 1A7 polynucleotide of interest. Another example of an expression vector (system) is the baculovirus/insect system.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (where the vector is an infectious agent, such as vaccinia virus, which is discussed below). The choice of means of introducing vectors or 1A7 polynucleotides will often depend features of the on the host cell.

Once introduced into a suitable host cell, for example, *E coli* or COS-7, expression of a 1A7 polypeptide can be determined using any of the assays described herein. For example, presence of 1A7 polypeptide can be detected by RIA or ELISA of the culture supernatant (if the 1A7 polypeptide is secreted) or cell lysates.

A particularly useful expression vector for 1A7 polynucleotides is a vaccinia virus comprised of a 1A7 polynucleotide sequence, which can also be used in vaccine preparations (Moss (1991) Science 252:1662-1667). To introduce polynucleotide sequences encoding 1A7 polypeptide, including 1A7 polypeptide fragments, into vaccinia, the polynucleotide sequence of interest is first inserted into a plasmid containing a vaccinia virus promoter with flanking sequences homologous to vaccinia DNA inessential for replication. Plasmid-containing cells are then infected with vaccinia, which leads to a low level of homologous recombination between plasmid and virus, with resultant transfer of the vaccinia promoter and 1A7 polypeptide-encoding polynucleotide sequence into the vaccinia virus genome. Typically, the 1A7 polynucleotide is inserted into the viral tk (thymidine kinase) gene. Insertion into the tk site attenuates the virus more than 10,000 fold compared to wild type (Flexner et al. (1980) Vaccine 88 (Cold Spring Harbor Laboratory), 179-184). Recombinant virus is identified by the $tk^-$ phenotype. Preferably, expression of the 1A7 polynucleotide is under the control of the vaccinia early/late promoter (7.5 K), whereby the resultant 1A7 polypeptides can be expressed in infected cells throughout the life cycle of the virus. However, other promoters known in the art can be used, such as pH6, or synthetic promoters. Expression of the 1A7 polypeptide occurs in cells infected with the recombinant vaccinia or individuals which are immunized with the live recombinant vaccinia virus. Any one of several strains of vaccinia can be used, including but not limited to WR, ALVAC, and NYVAC.

A vaccinia vector of this invention can contain one or more polynucleotides encoding a 1A7 polypeptide. It can also contain polynucleotide sequences encoding other polypeptides that enhance, facilitate, or modulate the desired result, such as lymphokines, including, but not limited to, IL-2, IL-4 and GM-CSF. A preferred lymphokine is GM-CSF. Preferred GM-CSF constructs are those which have been deleted for the AU-rich elements from the 3' untranslated regions and sequences in the 5' untranslated region that are capable of forming a hairpin loop. Also embodied in this invention are vaccinia vectors encoding for recombinant 1A7 variants containing 1A7 polypeptides, such as scFvs, chimeras, and polymers, as described below.

Host Cells Transformed with LA 7 Polynucleotides

Other embodiments of this invention are host cells transformed with 1A7 polynucleotides and vectors comprising 1A7 polynucleotide sequences, as described above. Both prokaryotic and eukaryotic host cells may be used. Prokaryotic hosts include bacterial cells, for example *E. coli* and mycobacteria. Among eukaryotic hosts are yeast, insect, avian, plant and mammalian cells. Host systems are known in the art and need not be described in detail herein. One example of a mammalian host cell is NS0, obtainable from the European Collection of Cell Cultures (England). Transfection of NS0 cells with a plasmid, for example, which is driven by a CMV promoter, followed by amplification of this plasmid in using glutamine synthetase provides a useful system for protein production. (Cockett et al. (1990) Bio/Technology 8:662-667).

The host cells of this invention can be used, inter alia, as repositories of 1A7 polynucleotides, or as vehicles for production of 1A7 polynucleotides and polypeptides. They may also be used as vehicles for in vivo expression of 1A7 polypeptides.

Uses for 1A 7 Polynucleotides

The polynucleotides of this invention have several uses. 1A7 polynucleotides are useful, for example, in expression systems for the production of 1A7 or 1A7 fragments. They are also useful as hybridization probes to assay for the presence of 1A7 polynucleotide or related sequences in a sample using methods well known to those in the art Further, 1A7 polynucleotides are also useful as primers to effect amplification of desired polynucleotides. The polynucleotides of this invention are also useful in pharmaceutical compositions including vaccines and for gene therapy.

1A7 polynucleotides can also be used as hybridization probes for detection of 1A7 encoding sequences. Suitable samples include cells transformed ex vivo for use in gene therapy. In one illustration, DNA or RNA is extracted from a sample, and optionally run on a gel and/or digested with restriction nucleases. The processed sample polynucleotide is typically transferred to a medium suitable for washing. The sample polynucleotide is then contacted with the 1A7 polynucleotide probe under conditions that permit a stable duplex to form if the sample contains a matching 1A7 sequence. Any stable duplexes formed are detected by any suitable means. For example, the 1A7 polynucleotide probe may be supplied in labeled form, and label remaining with the sample after washing will directly reflect the amount of stable duplex formed. In a second illustration, hybridization is performed in situ. A suitably prepared tissue sample is overlaid with a labeled 1A7 probe to indicate the location of 1A7 encoding sequences comprised therein.

A short 1A7 polynucleotide may also be used as a primer for a PCR reaction, particularly to amplify a longer sequence comprising a region hybridizing with the primer. This may be conducted preparatively, in order to produce polynucleotide for further genetic manipulation. It may also be conducted analytically, to determine whether a 1A7 encoding polynucleotide is present, for example, in a sample of diagnostic interest.

The 1A7 polynucleotides of this invention can be used in expression systems to produce 1A7 polypeptides, intact 1A7, or recombinant forms of 1A7, such as are described below.

Another use of 1A7 polynucleotides is in vaccines and gene therapy. The general principle is to administer the polynucleotide so that it either promoters or attenuates the expression of the polypeptide encoded therein. Thus, the present invention includes methods of inducing an immune response and methods of treatment comprising administration of an effective amount 1A7 polynucleotides to an individual. In these methods, a 1A7 polynucleotide encoding a 1A7 polypeptide is administered to an individual, either directly or via cells transfected with the 1A7 polynucleotide. Preferably, the 1A7 polynucleotide is in the form of a circular plasmid, preferably in a supercoiled configuration. Preferably, the 1A7 polynucleotide is replicated inside a cell. Thus, the 1A7 polynucleotide is operatively linked to a suitable promoter, such as a heterologous promoter that is intrinsically active in cells of the target tissue type. Preferably, once in cell nuclei, plasmids persist as circular non-replicating episomal molecules. In vitro mutation may be carried out with plasmid constructs to provide, for example, molecules that are more immunogenic or that comprise a T cell epitope with a desirable HLA motif.

To determine whether plasmids containing 1A7 polynucleotides are capable of expression in eukaryotic cells, eukaryotic cells such as COS-7, CHO, or HeLa cells can be transfected with the plasmids. Expression of 1A7 polypeptide is then determined by immunoassay; for example, by Western blot. Smaller 1A7 polypeptides can be detected, for example, by constructing the plasmid so that the resultant 1A7 polypeptide is fused with a tag, such as a target epitope or enzyme label. Further characterization of the expressed 1A7 polypeptide can be achieved by purifying the peptide and then conducting one of the functional assays described herein.

In one mode of gene therapy, the polynucleotides of this invention are used for genetically altering cells ex vivo. In this strategy, cells removed from a donor or obtained from a cell line are transfected or transduced with vectors encoding a 7 polypeptide, and then administered to a recipient Suitable cells for transfection include peripheral blood mononuclear cells.

In another mode of gene therapy, the polynucleotides of this invention are used for genetically altering cells in vivo. The purpose may include (but is not limited to) eliciting an antibody response to 1A7 or GD2, eliciting a T cell response to 1A7 or GD2, and treating various types of cancer. These uses are elaborated more fully in a later section.

Polypeptide Derivatives of 1A7

The present invention encompasses polypeptide fragments of 1A7 containing at least a portion of a variable region of 1A7. Preferred fragments are those with immunological activity of 1A7.

Also preferred are fragments which comprise amino acid sequences substantially different from other immunoglobulins, and fragments comprising a CDR. In one embodiment, the invention includes a polypeptide fragment of the 1A7 light chain variable region, comprising at least 5 consecutive amino acids, more preferably 15 consecutive amino acids, still more preferably 30 consecutive amino acids of SEQ ID NO:2, wherein the fragmet contains one or the other (preferably both) of the lysine residues at positions 50 and 55 of the mature light chain variable region sequence. In other embodiments, the invention includes a polypeptide fragment of the 1A7 heavy chain variable region, comprising the 5 amino acids from the CDR1 or comprising at least 8, preferably 10, more preferably 12, and still more preferably 16 of the amino acids from the CDR2; or comprising at least 4, preferably 6, more preferably 8, and still more preferably 9 of the amino acids from the CDR3. In yet other embodiments, the peptide comprises a combination of two or more sequences from positions 50-55 of the 1A7 light chain and the three CDRs of the heavy chain as outlined in this paragraph, optionally in combination with other 1A7 variable region sequences.

The size of the 1A7 polypeptide fragments may be only the minimum size required to provide a desired function. It may optionally comprise additional sequence, either native to 1A7, or from a heterologous source, as desired. 1A7 fragments may contain only 5 consecutive amino acids from a 1A7 variable region sequence. Polypeptides comprising 7 amino acids, more preferably about 10 amino acids, more preferably about 15 amino acids, more preferably about 25 amino acids, more preferably about 50 amino acids, more preferably about 75 amino acids from the 1A7 light or heavy chain variable region are also included. Even more preferred are polypeptides comprising the entire 1A7 light or heavy chain variable region.

The invention includes modified 1A7 polypeptides which are functionally equivalent to 1A7, or have altered but measurable 1A7 immunologic activity. Fragments with improved 1A7 immunologic activity are preferred. Examples of modified polypeptides include polypeptides with conservative substitutions of amino acid residues, and one or more deletions or additions of amino acids which do not significantly deleteriously change the functional activity.

One example of this is 1A7 polypeptides comprising one or more amino acid substitution in comparison with the prototype 1A7 sequence. Substitutions can range from changing or modifying one or more amino acids to complete redesign of a region, such as the variable region. Amino acid substitutions, if present, are preferably conservative substitutions that do not deleteriously affect folding or functional properties of the peptide. Groups of functionally related amino acids within which conservative substitutions may be made are glycine/ alanine; valine/isoleucine/leucine; asparagine/glutamine; aspartic acid/glutamic acid; serine/threonine/methionine; lysine/arginine; and phenylalanine/tryosine/tryptophan. Polypeptides of this invention may be in glycosylated or unglycosylated form, may be modified post-translationally (e.g., acetylation, and phosphorylation) or may be modified synthetically (e.g., the attachment of a labeling group).

The invention also encompasses fusion proteins comprising one or more 1A7 polypeptide. A 1A7 fusion polypeptide can be prepared, for example, by chemical synthesis, or by creating and translating a polynucleotide in which the peptide regions are encoded in the desired relationship. Alternatively, fusion proteins may be provided in expression systems constructed by co-transfection with plasmids comprising encoding regions for different functional regions of the protein.

Useful heterologous sequences for inclusion in a fusion polypeptide include sequences that provide for secretion from a host cell, enhance immunological reactivity, or facilitate the coupling of the polypeptide to an immunoassay support or a vaccine carrier. One example is a bacteria "super antigens", such as staphylococcal enterotoxin A (SEA) (Dohlsten et al. (1994) Proc. Nad. Acad. Sci. USA 91:8945-8949). In a preferred example, a 1A7 polypeptide is fused with a bioresponse modifier, particularly a cytokine, which may enhance immunogenicity. Examples of bioresponse modifiers include cytokines and lymphokines such as GM-CSF, interleukin-2 (IL 2), interleukin 4 (IL-4), and y-interferon. GM-CSF and IL-2 are especially preferred The preferred arrangement is for the cytokine effector unit to be fused to the C-terminal of the immunoglobulin heavy chain 1A7 polypeptide derivatives comprising both a 1A7 light chain and a 1A7 heavy chain may be formed as separate light and heavy chains and then assembled, or assembled in situ by an expression system for both chains. Such expression systems may be created by tranfecting with a plasmid comprising separate transcribable regions for the light and heavy chain, or by co-transfecting the same cell with plasmids for each chain. In a third method, a suitable plasmid with a heavy chain encoding region is transfected into a heavy chain loss mutant. For example, heavy chain loss mutants can be obtained by treating $2 \times 10^7$ 1A7 cells with fluorescein-labeled rabbit anti-mouse IgG (H chain specific, DAKO Corporation, Carpinteria, Calif.) according to the supplier's instruction. The stained and unstained cell populations are analyzed in a fluorescence-activated cell sorter. The unstained cells are collected in a sterilized tube and placed in 96-well plates with 1 cell/well by limiting dilution. The culture supernatants are then assayed by ELISA using goat anti-mouse IgG (heavy chain specific) and goat anti-mouse kappa The clones with kappa-positive and IgG-negative phenotype are subcloned at least 3 times to obtain stable $1A7^{(-H)}$ mutants. mRNA from putative heavy chain loss mutant $1A7^{(-H)}$ cones can be isolated and the sequence of the light chain variable region cDNA determined. Reverse PCR of the mRNA for the 1A7 $V_H$ is performed with 2 sets of 5'- and 3'-primers, used for cloning of $1A7^{(-H)}$ cDNA (Example 2). A heavy chain loss mutant should yield no detectable DNA band. Transfection of these cells may then proceed using a suitable heavy chain plasmid construct.

The invention also encompasses a hybrid antibody, in which one pair of heavy and light chains is obtained from a first antibody, which the other pair of heavy and light chains is obtained from a different second antibody. For purposes of this invention, one pair of light and heavy chains is from 1A7. In one example, each light-heavy chain pair binds different epitopes of GD2. Such hybrids may also be formed using chimeric heavy or light chains.

Another embodiment is a humanized version of 1A7. "Humanized" antibodies are antibodies in which at least part of the sequence has been altered from its initial form to render it more like human immunoglobulins. In one version, the heavy chain and light chain constant regions are replaced with human sequence. This is a fusion polypeptide comprising a 1A7 variable region and a heterologous immunoglobulin constant region. In another version, the CDR regions comprise 1A7 amino acid sequences, while the variable framework regions have also been converted human sequences. See, for example, EP 0329400. In a third version, variable regions are humanized by designing consensus sequences of human and mouse variable regions, and converting residues outside the CDRs that are different between the consensus sequences.

Another 1A7 derivative contemplated by this invention is an antibody in which the 1A7 heavy or light chain has been modified to provide additional properties. For instance, a change in amino acid sequence can result in greater immunogenicity of the resultant 1A7 polypeptide. The changes range from changing of one or more amino acids to the complete redesign of a region such as a constant region domain. Changes contemplated affect complement fixation, interaction with membrane receptors, and other effector functions. A recombinant 1A7 antibody may also be designed to aid the specific delivery of a substance (such as a lymphokine) to an effector cell. Also contemplated are proteins in which various immunoglobulin domains have been placed in an order other than occurs in nature.

The invention also encompasses single chain variable region fragments ("scFv") of 1A7. Single chain variable region fragments are made by linking light and/or heavy chain variable regions by using a short linking peptide (Bird et al (1988) Science 242: 423-426). Any peptide having sufficient flexibility and length can be used as a linker in a scFv. Usually the linker is selected to have little to no immunogenicity. An example of a linking peptide is (GGGGS)$_3$ (SEQ. ID NO:45), which bridges approximately 3.5 nm between the carboxy terminus of one variable region and the amino terminus of another variable region. Other linker sequences may also be used, and may provide additional functions, such as a means for attaching a drug or to a solid support.

All or any portion of the heavy or light chain can be used in any combination. Typically, the entire variable regions are included in the scFv. For instance, the light chain variable region can be linked to the heavy chain variable region. Alternatively, a portion of the light chain variable region can be linked to the heavy chain variable region, or portion thereof. Also contemplated are scFvs in which the heavy chain variable region is from 1A7, and the light chain variable region is from another immunoglobulin. It is also possible to construct a biphasic, scFv in which one component is a 1A7 polypeptide and another component is a different polypeptide, such as a T cell epitope.

The scFvs can be assembled in any order, for example, $V_H$-(linker)-$V_L$ or $V_L$-(linker)-$V_H$. There may be a difference in the level of expression of these two configurations in particular expression systems, in which case one of these forms may be preferred. Tandem scFvs can also be made, such as (X)(linker)-(X)-(linker)-(X), in which X are 1A7 polypeptides, or combinations of 1A7 polypeptides with other polypeptides. In another embodiment, single chain 1A7 antibody polypeptides have no linker polypeptide, or just a short, inflexible linker. Possible configurations are $V_L$-$V_H$ and $V_H$-$V_L$. The linkage is too short to permit interaction between $V_L$ and $V_H$ within the chain, and the chains form homodimers with a $V_L$/$V_H$ antigen binding site at each end. Such molecules are referred to in the art as "diabodies".

Single chain variable regions may be produced either recombinantly or synthetically. For synthetic production of scFv, an automated synthesize can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli, and the expressed protein may be isolated using standard protein purification techniques.

A particularly useful system for the production of 1A7 scFv's is plasmid vector pET-22b(+) (Novagen, Madison, Wis.) in E. coli. pET-22b(+) contains a nickel ion binding domain consisting of 6 sequential histidine residues, which allows the expressed protein to be purified on a suitable affinity resin. Another example of a vector that can be used is pcDNA3 (Invitrogen, San Diego, Calif.), described above.

Conditions of expression should be such that the scFv polypeptide can assume optimal tertiary structure. Depending on the plasmid used (especially the activity of the promoter) and the host cell, it may be necessary to modulate the rate of production. For instance, use of a weaker promoter, or expression at lower temperatures, may be necessary to optimize production of properly folded scFv in prokaryotic systems; or it may be preferably to express scFv in eukaryotic cells.

Preferred single chain variable regions comprise at least 10 consecutive amino acids of SEQ. ID NO:2 and at least 10 consecutive amino acids of SEQ. ID NO:4, especially wherein the amino acids of SEQ. ID NO:2 and the amino acids of SEQ. ID NO:4 are joined by a linker polypeptide of 5 to 20 amino acids, or comprising the light chain variable region and the heavy chain variable region of monoclonal antibody 1A7.

The invention also encompasses polymeric forms of 1A7 polypeptides, containing a plurality of 1A7 polypeptides. One embodiment is a linear polymer of 1A7 polypeptides, optionally conjugated to carrier. These linear polymers can comprise multiple copies of a single 1A7 polypeptide, or combinations of different 1A7 polypeptides, and can have tandem 1A7 polypeptides, or 1A7 polypeptides separated by other amino acid sequences. Another embodiment is 1A7 multiple antigen peptides (MAPs) MAPs have a small immunologically inert core having radially branching lysine dendrites, onto which a number of 1A7 polypeptides are covalently attached. See Posnett et al. (1988). Biol. Chem. 263:1719-1725; Tam (1989) Methods Enzymol. 168:7-15. The result is a large macromolecule having a high molar ratio of 1A7 polypeptides to core. MAPs are efficient immunogens and useful antigens for immunoassays. The core for creating an 1A7 MAP can be made by standard peptide synthesis techniques, or obtained commercially (Quality Controlled Biochemicals, Inc., Hopkinton, Mass.). A typical core matrix is made up of three levels of lysine and eight amino acids.

In another embodiment of the invention, the immunogenicity of the 1A7 polypeptides is enhanced by preparing them in expression systems in which they are assembled with particle-forming proteins such as, for example, those associated with hepatitis B virus. See, e.g., U.S. Pat. No. 4,722,840. Constructs wherein the 1A7 polypeptide is linked directly to particle-forming protein coding sequences produce hybrids which are immunogenic for an anti-GD2 response. The vectors also comprise immunogenic HBV epitopes; for example, the pre-S peptide and stimulate a response against HBV. Such expression systems may be provided in eukaryotic cells, including yeast or mammalian cells.

In another embodiment, 1A7 polypeptides are conjugated to a carrier molecule. This is desirable for a 1A7 peptide that comprises a suitable epitope for eliciting anti-GD2, but is too small to be immunogenic. Any conjugation method known in the art may be used. Any carrier can be used which is not harmful to the host. Suitable carriers are typically large, slowly metabolized macromolecules such as proteins; polysaccharides (such as latex functionaliaed SEPHAROSE™, agarose, cellulose, cellulose beads and the like); polymeric amino acids (such as polyglutamic acid, polylysine, and the like); amino acid copolymers; and inactive virus particles or attenuated bacteria, such as Salmonella. Especially useful carrier proteins are serum albumins, keyhole limpet hemocyanin (KLH), certain immunoglobulin molecules, thyroglobulin, ovalbumin, and tetanus toxoid. KLH is especially preferred.

1A7 polypeptides of the invention can be identified in a number of ways. For example, the variable regions of the light and heavy-chains can be screened by preparing a series of short polypeptides that together span the entire variable region amino acid sequence. Using a series of polypeptides of 20 or 50 amino acids in length, each 1A7 variable region may be surveyed for useful functional properties. It is also possible to carry out a computer analysis of a protein sequence to identify potentially interesting polypeptides, such as those that bear the shape of D2, or those involved in idiotype-anti-idiotype contact.

Those skilled in the art will readily appreciate that the various adaptations of 1A7 described in this section may be combined in various fashions to yield other 1A7 polypeptides with desirable properties. For instance, 1A7 polypeptides with modified residues may be comprised in a MAP. In another example, a 1A7 scFv is fused to a cytokine, such as IL-2. AU such combinations are contemplated in this invention.

Preparation of 1A 7 Polypeptides

The polypeptides of this invention can be made by any suitable procedure, including proteolysis of the 1A7 antibody, by recombinant methods or by chemical synthesis.

1A7 polypeptides, especially shorter polypeptides up to about 50 amino acids, are conveniently made by chemical synthesis, based on the sequence data and other information provided herein.

Certain 1A7 polypeptides which are fragments of the whole molecule may alternatively be prepared from enzymatic cleavage of intact 1A7. Examples of proteolytic enzymes include, but are not limited to, trypsin, chymotrypsin, pepsin, papain, V8 protease, subtilisin, plasmin, and thrombin. Intact 1A7 can be incubated with one or more proteinases simultaneously or sequentially. Alternatively, or in addition, 1A7 can be treated with disulfide reducing agents. Peptides may then be separated from each other by techniques known in the art, including but not limited to gel filtration chromatography, gel electrophoresis, and reverse-phase HPLC.

A 1A7 polypeptide can also be made by obtaining a polynucleotide encoding it according to the information provided elsewhere in this application, and introducing it into a suitable expression system. Typically, polynucleotides encoding a 1A7 polypeptide are ligated into an expression vector under control of a suitable promoter and used to genetically alter the intended host cell. Both eukaryotic and prokaryotic host systems can be used. The polypeptide is then isolated from lysed cells or from the culture medium and purified to the extent needed for its intended use. Examples of prokaryotic host cells appropriate for use with this invention include *E. coli*. Examples of eukaryotic host cells include avian, insect, plant, and animal cells such as COS7, HeLa, and CHO cells.

In certain applications, such as when a 1A7 polypeptide is expressed in a suitable storage medium such as a plant seed, the 1A7 polypeptide can be used without purification (Fiedler et al. (1995) Biotechnology 13:1090-1093). For most applications, it is generally preferable that the polypeptide is at least partially purified from other cellular constituents. Preferably, the polypeptide is at least about 50% pure as a weight percent of total protein. More preferably, the protein is at least about 50-75% pure. For clinical use, the polypeptide is preferably at least about 80% pure, according to the criteria given in another section.

Characterization of 1A 7 Polypeptides

The 1A7 polypeptides of this invention can be char d in several ways. For instance, a 1A7 polypeptide may be tested for its ability to bind specifically to 14G2a, for its ability to specifically inhibit the binding between 14G2a and intact 1A7, or for its ability to specifically inhibit the binding between 14G2a and GD2. Alternatively, a 1A7 polypeptide can be tested for its ability to elicit an immune response, preferably an anti-GD2 response. 1A7 polypeptides can also be tested for their ability to palliate or ameliorate GD2-associated disease, such as GD2-associated tumors. It is understood that only one of these properties need be present in order for a polypeptide to come within this invention, although preferably more than one of these properties is present.

The ability of a 1A7 polypeptide to bind 14G2a may be tested by immunoassay. Any form of direct binding assay is suitable. In one such assay, the 14G2a or alternatively the 1A7 polypeptide is labeled. Suitable labels include radioisotopes such as $^{125}$I, enzymes such as peroxidase, fluorescent labels such as fluorescein, and chemiluminescent labels. Typically, the other binding partner is insolubilized (for example, by coating onto a microtiter plate) to facilitate washing. After combining the labeled component with the insolubilized component, the solid phase is washed and the amount of bound label is determined. Another such assay is a sandwich assay, in which the putative 1A7 polypeptide is captured by a first anti-immunoglobulin on a solid phase and developed with a second anti-immunoglobulin. Either the insolubilized or labeled anti-immunoglobulin or both is 14G2a. In either of these examples, the extent of binding of 1A7 is directly related to the amount of label bound to the solid phase.

To conduct the inhibition assays, the putative 1A7 polypeptide is titered for its ability to decease the binding of 1A7 to 14G2a, or 14G2a to GD2. Either of the binding pairs in the reaction to be inhibited is labeled, while the other is typically insolubilized in order to facilitate washing. GD2, if it is used, may be provided as the purified ganglioside, or as a GD2-expressing cell line, like M21/P6. The 1A7 polypeptide is typically mixed with the labeled component, and then the name is combined with the solid phase. Polypeptides with the characteristics of 1A7 will proportionately decrease the amount of label attached to the solid phase, compared with control polypeptides. This test may be more sensitive than measuring direct binding, because lower affinity interaction between 1A7 and Ab1 may be too weak to form a stable bond, but adequate to interfere with the binding of another ligand-receptor pair when present at sufficient concentration.

A 1A7 polypeptide or a molecule comprising such a peptide that has an Fc-like effector component may be tested for their ability to mediate immune effector reactions, particularly complement-mediated cytolysis (CMC) and antibody-dependent cellular cytotoxicity (ADCC). Suitable assays are described elsewhere in this disclosure.

Another way of characterizing 1A7 polypeptides, particularly those intended for use in therapy, is to test their ability to generate an immune response. Suitable techniques for characterizing the immune response are given in a later section.

Uses of Polypeptides

Polypeptide fragments, fusion proteins, and other derivatives of 1A7 have many uses The uses generally parallel those of the intact 1A7 antibody as outlined earlier in this disclosure. Certain derivatives may have desirable effects for particular uses. For example, humanized or single-chain variable region molecules may be desirable for human administration, because they are less likely to stimulate an anti-mouse isotype response. Fusion proteins comprising a cytokine may be more immunogenic.

Preferred uses of these compounds include eliciting an antibody response to 1A7 or more preferably GD2, eliciting a T cell response to 1A7 or more preferably GD2, and treating various types of GD2-associated cancer. These uses are elaborated more fully in a later section.

Pharmaceutical Compositions and Vaccines Comprising 1A7 Antibody and Polynucleotide and Polypeptide Derivatives The present invention encompasses phaamceuacal compositions and vacines containing 1A7 antibody, or polynucleotide or polypeptide derivatives of 1A7 either alone or in combination. Such pharmaceutical compositions and vaccines are useful for eliciting an immune response and treating GD2-associated diseases, either alone or in conjunction with other forms of therapy, such as chemotherapy or radiotherapy.

Pharmaceutical compositions include vaccines for direct administration to an individual. Vaccines may comprise 1A7 antibodies, polynucleotides, or polypeptide derivatives, or a combination thereof.

Vaccines containing naked 1A7 polynucleotides can be used for genetic immunization (see generally Tang et al. (1992) Nature 356: 152-154). Once in the cell nuclei, plasmids comprising 1A7 encoding regions may persist as circular non-replicating episomes leading to dose-dependent and long-lived expression. (Spooner et al. (1995) Gene Therapy 2:173-180). Immunization using polynucleotides has been shown to generate cellular as well as humoral responses (Spooner et al.; Wang et al. (1995) Human Gene Therapy 6:407-418). Genetic immunization has many of the advantages of live or attenuated microorganisms as vehicles for eliciting an immune response, without the risk of infection.

Preferably, 1A7 polynucleotides are in the form of plasmid vectors containing appropriate control sequences for transcription and translation, such as promoters, enhancers, and signal sequences. One or more 1A7 polynucleotides can be used within a single cloning vector, or multiple vectors can be used. A preferred 1A7 encoding region for use in a polynucleotide vaccine encodes a 1A7 scFv. The polynucleotide vaccine may also comprise encoding regions for other substances which will enhance the immune response. A preferred example is GM-CSF.

Another preferred embodiment of an 1A7 polynucleotide suitable for use as a vaccine is a viral vector. Examples include adenovirus, adeno-associated retroviruses (AAV), and SV40. Especially preferred is a vaccinia vector, whereby the polypeptide encoded by the 1A7 polynucleotide is expressed along with the immunogenic viral particle. Recombinant vaccinia comprising polynucleotides encoding 1A7 polypeptides such as scFv may be used for direct vaccination at about $10^7$ to $10^8$ plaque forming units per dose. Vaccinia can be administed parenterally, by subcutaneous or intramuscular injection, for example, as well as through mucosal membranes, such as nasally, orally or by inhalation. Alternatively, vaccinia can be administered via vaccinia-infected cells. In this technique, suitable cells, such as tumor cells, are infected with vaccinia in culture. The infected cells are then reintroduced to the individual. Methods for infecting cells with vaccinia and reintroducing these infected cells, have been described (see, e.g., Moss (1991)).

Other 1A7 polynucleotide vaccines may be designed using other delivery vehicles known in the art. Another such delivery vehicle is cationic liposomes, to which DNA may be readily attached by virtue of its charge.

Vaccines can also be prepared from the 1A7 antibody, polypeptide derivatives thereof, or an combination thereof. A protein can optionally be treated chemically to enhance its immunogenicity, especially if 100 amino acids or less. This may include cross-linking, for example, with glutaraldehyde; or linking to a protein carrier, such as keyhole limpet hemocyanin (KLH) or tetanus toxoid.

The preparation of pharmaceutical compositions that contain 1A7 antibody, or polynucleotide or polypeptide derivative as an active ingredient is conducted in accordance with generally accepted procedures for the preparation of pharmaceutical preparations. See, for example, *Remington's Pharmaceutical Sciences* 18th Edition (1990), E. W. Martin ed., Mack Publishing Co., PA. Depending on the intended use and mode of administration, it may be desirable to process the active ingredient further in the preparation of pharmaceutical compositions. Appropriate processing may include sterilizing, mixing with appropriate non-toxic and non-interfering components, dividing into dose units, and enclosing in a delivery device.

Liquid pharmaceutically administrable compositions can, for example, be prepared by dissolving or dispersing a vector embodied herein in a liquid excipient, such as water, saline, aqueous dextrose, glycerol, or ethanol. The composition may optionally also contain other medicinal agents, pharmaceutical agents, adjuvants, carriers, and auxiliary substances such as wetting or emulsifying agents, and pH buffering agents.

Protein vaccines of this invention typically comprise an adjuvant, which may be the same as or in addition to the excipient or carrier. Examples of adjuvants include but are not limited to aluminum hydroxide, alum, QS-21 (U.S. Pat. No. 5,057,540), DHEA (U.S. Pat. Nos. 5,407,684 and 5,077,284) including its precursors and modified forms (e.g., DHEA-S, the sulfonated form of DHEA), β2 microglobulin (WO 91/16924), muramyl dipeptides, muramyl tripeptides (U.S. Pat. No. 5,171,568), monophosphoryl lipid A (U.S. Pat. No. 4,436,728; WO 92/16231) and its derivatives, such as various forms and generations of DETOX™ and BCG (U.S. Pat. No. 4,726,947). Other suitable adjuvants are aluminum salts, squalene mixtures (SAF-1), muramyl peptide, saponin derivatives, mycobacterium wall preparations, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) Nature 344:873-875. For veterinary use and for production of antibodies in animals, complete and incomplete Freund's adjuvant can be used. The choice of an adjuvant will depend, in part, on the stability of the vaccine in the presence of the adjuvant, the route of administration, and the regulatory acceptability of the adjuvant, particularly when intended for human use. For instance, alum is approved by the United States Food and Drug Administration (FDA) for use as an adjuvant in humans.

A preferred vaccine composition comprising 1A7 antibody or peptide derivative is prepared by mixing with aluminum hydroxide and incubated to about 48° C. for about 30 min. Even more preferred are vaccine compositions comprising 1A7 and QS-21 or RIBI™PC. QS-21 and RIBI™PC are equally preferred; and the selection between them is made on the basis of availability.

Pharmaceutical compositions of the present invention are administered by a mode appropriate for the form of composition. Possible routes include intracutaneous, subcutaneous, intramuscular, intraperitoneal, intradermal, oral, intranasal, intradermal, and intrapulmonary (i.e., by aerosol). Protein vaccines of this invention for human use are typically administered by a parenteral route, most preferably subcutaneous. A series of injections is preferably given at different subcutaneous sites.

Pharmaceutical compositions for oral, intranasal, or topical administration can be supplied in solid, semi-solid or liquid forms, including tablets, capsules, powders, liquids, and suspensions. Compositions for injection can be supplied as liquid solutions or suspensions, as emulsions, or as solid forms suitable for dissolution or suspension in liquid prior to injection. For administration via the respiratory tract, a preferred composition is one that provides either a solid or liquid aerosol when used with an appropriate aerosolizer device. Although not required, pharmaceutical compositions are preferably supplied in unit dosage form suitable for administration of a precise amount. Also contemplated by this invention are slow release or sustained release forms, whereby a relatively consistent level of the active compound are provided over an extended period.

It is recognized that a number of alternative vaccine compositions, not limited to those described herein, may be efficacious in inducing an immune response. All such compositions are embodied within the present invention, providing they include a 1A7 polynucleotide or polypeptide as an active ingredient. The pharmaceutical compositions of this invention can be used in conjunction with other modes of therapy, whether established or experimental, whenever his is clinically desirable.

Testing 1A7 Compounds and compositions for the Ability to Elicit a Specific Immune Response Compounds embodied in this invention may be assessed for their ability to elicit a specific immune response. Accordingly, test compounds are prepared as a suitable pharmaceutical composition and administered to test subjects. Initial studies are preferably done in small animals such as mice or rabbits, optionally next in non-human primates and then ultimately in humans. Immunogenicity is preferably tested in individuals without a previous anti-1A7 response.

A test composition in an appropriate test dose is administered on an appropriate immunization schedule. It may be appropriate to compare different doses and schedules within the predicted range.

Samples (usually blood samples) are collected regularly during treatment, and assayed for a specific immune response. The response may include antibody, helper-inducer T cells, or cytotoxic T cells, or a combination thereof. As a screening test, the samples may be measured for an anti-1A7 response. Since the objective is typically to identify compositions useful in cancer therapy, the samples are preferably measured for an anti-GD2 response, as manifest in direct or inhibition type experiments.

This section outlines some non-limiting examples of assays that are suitable to monitor the immune response.

Presence of anti-1A7 (Ab3) and anti-GD2 (Ab1') activity in a humoral response is preferably determined after first pre-incubating sera with autologous immunoglobulin or adsorbing on a suitable affinity resin to remove antibody activity against isotypic and allotypic determinants. The adsorbed serum is then tested for Ab3 or Ab1' activity, for example, using ELISA or RIA. For instance, different dilutions of pre-reacted sera are reacted with 1A7 (or 1A7 polypeptide) coated on microtiter plates. An unrelated Ab2 serves as a control. After washing, the Ab3-1A7 complex is labeled using, for example, $^{125}$I-labeled 1A7 in a homogeneous sandwich assay. Results from this assay are compared to those obtained before administration of the 1A7 polypeptide (Example 1). Alternatively, binding to GD2 positive cells, such as M21/P6 cells, can be tested using immune flow cytometry. In a third example, the specificity of Ab3 is determined by Western blot GD2 is separated by SDS-PAGE and blotted to a nitrocellulose filter. The filter is then incubated with sera containing Ab3, and the reaction developed by a suitably labeled anti-immunoglobulin. If the Ab3 binds to GD2, a band at the appropriate molecular weight should appear.

If desired, the specificity of the Ab3 can be further characterized. For example, competition assays can be performed to determine whether Ab3 share Ab1 idiotopes. Accordingly, competition experiments are conducted in which Ab3 is tested for inhibition of binding between 1A7 and 14G2a Inhibition indicates that Ab3 and 14G2a contain at least some similar binding determinants. Competition of Ab3 with the binding of 14G2a to GD2 may also be measured.

Another way of characterizing a composition of this invention is testing its ability to elicit an antibody that is cytotoxic. For determination of complement mediated cytotoxicity (CMC), M21/P6 target cells expressing GD2 are labeled with $^{51}$Cr. Labeling may be accomplished by incubating about $10^6$ cells with approximately 200 μCi $Na_2SO_4$ for 60 minutes at 37° C., followed by washing. The assay is conducted by adding and incubating serum suspected of containing antibody. Guinea pig serum pre-adsorbed with M21/P6 cells (or other source of complement) is then added. After a suitable incubation period at 37° C., extent of $^{51}$Cr release is then measured and compared with that of unopsonized control cells. Release of $^{51}$Cr correlates with CMC activity (Herlyn et al. (1981) Int J. Cancer 27:769).

Another way of characterizing a composition of this invention is by testing its ability to elicit an anti-GD2 antibody that participates in an ADCC response (Cheresh et al. (1986) Cancer Research 46:5112-5118). In this assay, cultured human M21/P6 cells (which express GD2 in their surface) are labeled with $^{51}$Cr and are used as target cells. Normal human peripheral blood mononuclear cells (PBMC) are used as effector cells. The Ab3 containing serum from immunized subjects is supplied to mediate the ADCC reaction. Preferably, the ADCC assay is conducted in the presence of heat-inactivated serum with an effector to target cell ratio of 100:1 for 4 hours, although other suitable conditions may be used. The amount of $^{51}$Cr released is then measured.

The 1A7 antibodies, polynucleotides and polypeptides of this invention can also be characterized by their ability to elicit a cellular immune response. As used herein, a "cellular immune response" is a response that involves T cells, and can be observed in vitro or in vivo. Subjects are immunized with the 1A7 composition, and cells are recovered for assaying the response. Where the subject is a small animal, cells are typically obtained from the spleen. For larger animals including humans, cells are typically obtained from peripheral blood. A suitable cell population is recovered from the sample by standard separation techniques, typically involving centrifugation over an appropriate medium such as FICOLL-HYPAQUE™.

One way of detecting a cellular immune response is by assaying for T cell proliferative activity. In this test, cellular immune response is measured by proliferation of peripheral blood mononuclear cells (PBMCs) incubated with 1A7 polypeptide. PBMCs are isolated after a requisite number of administrations of 1A7 polypeptide, and are incubated with varying concentrations of 1A7 polypeptide. A non-specific mitogen such as PHA serves as a positive control; incubation with an unrelated anti-idiotype antibody serves as a negative control. Preferably, the stimulator cells are autologous with the responder cells, particularly in terms of histocompatibility Class II antigens. After incubation of the PBMCs for an appropriate period (typically 5 days), [$^3$H]thymidine incorporation is measured. If desired, determination of which subset of T cells are proliferating can be performed using flow cytometry. Optionally, splenic T cells can be pre-depleted of either $CD4^+$ or $CD8^+$ cells before the proliferation assay by incubation with monoclonal antibody RL.172 (anti-$CD4^+$) or monoclonal antibody.168 (anti-$CD8^+$) and complement.

Another way of detecting a cellular immune response is to test for T cell cytotoxicity (CTL) activity. In this test, an enriched T cell population are used as effectors in a standard $^{51}$Cr release assay (Kantor et al. (1992) J. Natl. Cancer Inst. 84:1084-1091). An example of a $^{15}$Cr release assay is the following. GD2-positive tumor cells (typically 1-2×$10^6$ cells) are radiolabeled as target cells with about 200 μCi of $Na_2$$^{51}$$CrO_4$ (Amersham Corp., Arlington Heights, Ill.) for 60 minutes at 37° C., followed by thorough washing to remove unincorporated isotopes. T cells and targets ($1\times10^4$/well), both resuspended in culture medium, are then be combined at various effector-to-target ratios in 96-well, U-bottom plates (Costar Corp.). The plates are centrifuged at 100×g for 5 minutes to initiate cell contact, and are incubated for 4 or 16 hours at 37° C. with 5% $CO_2$. After incubation, supernatants are collected using a Supernatant Collection System (Skatron, Inc., Sterling, Va.) and radioactivity will be quantitated in a gamma counter (Beckman Instruments). Spontaneous release of $^{51}Cr$ is determined by incubation of targets in the absence of effectors, while maximum or total release of $^{51}Cr$ will be determined by incubation of targets in 0.1% TRITON X-100. Percentage of specific release of $_{51}Cr$ is calculated in relation to spontaneous and maximal release.

Another way of chat a 1A7 polypeptide is testing its ability to ameliorate, delay the progression or reduce the extent of GD2-associated disease, as outlined in the following section.

Use of Pharmaceutical Compositions for Eliciting an Immune Response and Treating Disease Compositions embodied in this invention such as those outlined in the previous section may be used for administration to individuals. They may be administered for experimental purposes, or to obtain a source of anti-GD2.

Compositions of this invention are particularly suitable for administration to human individuals with a GD2-associated disease. A GD2 associated disease is one in which expression of the GD2 ganglioside is altered at the affected tissue site, usually an elevation in cell-surface expression Relevant diseases are those in which an active immune response against GD2 would confer a clinical benefit Especially relevant are GD2-associated cancers; particularly melanoma, neuroblastoma, glioma, sarcoma, and small cell lung cancer.

The compositions of this invention may be administered to an individual with one of several objectives in mind. For example, the various compositions of this invention may be used to elicit an immune response. This includes an anti-1A7 specific response, and more preferably an anti-GD2 response. The desired response may be a specific antibody response; a specific T helper-inducer repines, or a specific cytotoxic T cell response. An ADCC response or a cytotoxic T cell response is especially preferred in the context of cancer therapy, since these arms of the immune system are believed to be important effector elements in immune surveillance. The presence of an antibody response may provide a convenient means for routine clinical monitoring. Thus, a response that involves several components of the immune response in combination is especially preferred.

Assays for measuring and characterizing antibody response, ADCC, antibody-mediated cytolytic activity, T cell proliferative activity, and cytotoxic T cell activity are all described elsewhere in this disclosure.

Also included in this invention are methods for tinting GD2-associated disease, such as a tumor expressing GD2. The method comprises administering an amount of a pharmaceutical composition effective to achieve the desired effect be it palliation of an existing tumor mass or prevention of recurrence.

Dose

For treatment of a GD2-associated disease in vivo, the amount of a pharmaceutical composition administered is an amount effective in producing the desired effect. An effective amount may be provided in one or a series of administrations.

For intact 1A7, a mouse requires approximately 100 μg of KLH-coupled 1A7 emulsified in CFA and IFA in each of at least about three and typically at least four administrations. Monkeys require approximately 2 mg. The range of intact 1A7 that can be appropriately administered to humans is from about 10 μg to 20 mg, preferably 200 μg to 15 mg, more preferably 500 μg to 10 mg, still more preferably 1 mg to 4 mg, and even more preferably 2 mg. Smaller peptides and fusion proteins may be more potent on a per-weight basis, and the preferred dose may be lower than with the intact molecule. Appropriate doses can easily be determined by comparing various doses of intact 1A7 and derivatives thereof in animal models, and scaling appropriately for human use.

The amount of 1A7 polynucleotide to be administered will depend upon several factors, such as the route of administration, the condition of the individual, and the desired objective. Typically, if administered directly, the amount per administration is about 10 μg to 1 mg, preferably 25 μg to 500 μg, more preferably 30 μg to 250 μg, even more preferably 50 to 100 μg.

Administrations are typically conducted on a weekly or biweekly basis until a desired, measurable parameter is detected, such as elicitation of an immune response. Administration can then be continued on a less frequent basis, such as biweekly or monthly, as appropriate.

The various compounds of this invention can be used alone, or in conjunction with other active agents that promote the desired objective, or provide a desirable adjunct therapy.

The exact dose and timing for the administration of any composition of this invention depends on the individual to be treated, the capacity of the individual's immune system to synthesize antibodies, the route of administration, the degree of protection desired, and the immunological and clinical response to previous doses. The immunological response may be assessed by assays given in the previous section. Choosing an appropriate amount to administer accordance with the guidelines suggested are the responsibility of the administering physician.

Appropriate Subjects for Therapy, and Desirable Effects

Suitable subjects include those who are suspected of being at risk of a pathological effect of any GD2-associated condition are suitable for treatment with the pharmaceutical compositions of this invention. Those with a history of a GD2-associated cancer are especially suitable.

The clinical studies described in the Example section are designed to exclude subjects who have not been treated previously with mouse immunoglobulin. The concept is that a proportion of subjects who have been so treated may have circulating anti-mouse immunoglobulin (HAMA). This selection criteria has been implemented to facilitate initial testing. However, the presence of HAMA is not believed to be an impediment to therapy, since the purpose of the 1A7 is to elicit a response, not remain in the circulation. Patients are more typically chosen for therapy irrespective of their history of previous treatment with mouse immunoglobulin. Of course, for certain engineered compounds like humanized 1A7 and scFv, most mouse isotype determinants have been deleted, and the presence of HAMA in a potential recipient is even less of a consideration.

Suitable human subjects for therapy comprise two groups, which may be distinguished by clinical criteria.

Patients with "advanced disease" or "high tumor burden" are those who bear a clinically measurable tumor. A clinically measurable tumor is one that can be detected on the basis of tumor mass (e.g., by palpation, CAT scan, or X-ray, positive biochemical or histopathological markers on their own are insufficient to identify this population). A pharmaceutical composition embodied in this invention is administered to these patients to elicit an anti-GD2 response, with the objective of palliating their condition. Ideally, reduction in tumor mass occurs as a result, but any clinical improvement constitutes a benefit. Clinical improvement includes decreased risk or rate of progression or reduction in pathological consequences of the tumor.

A second group of suitable subjects is known in the art as the "adjuvant group". These are individuals who have had a history of a GD2-associated cancer, but have been responsive to another mode of therapy. The prior therapy may have included (but is not restricted to) surgical resection, radiotherapy, and traditional chemotherapy. As a result, these individuals have no clinically measurable tumor. However, they are suspected of being at risk for progression of the disease, either near the original tumor site, or by metastasis.

This group may be further subdivided into high-risk and low-risk individuals. The subdivision is made on the basis of features observed before or after the initial treatment These features are known in the clinical arts, and are suitably defined for each different GD2-associated cancer. Features typical of high risk subgroups are those in which the tumor has invaded neighboring tissues, or who show involvement of lymph nodes.

A pharmaceutical composition embodied in this invention is administered to patients in the adjuvant group, or in either of these subgroups, in order to elicit an anti-GD2 response. Ideally, the composition delays recurrence of the cancer, or even better, reduces the risk of recurrence (i.e., improves the cure rate). Such parameters may be determined in comparison with other patient populations and other modes of therapy.

Of course, cross-overs between these two patient groups are possible, and the pharmaceutical compositions of this invention may be administered at any time that is appropriate. For example, 1A7 therapy may be conducted before or during traditional therapy of a patient with high tumor burden, and continued after the tumor becomes clinically undetectable. 1A7 therapy may be continued in a patient who initially fell in the adjuvant group, but is showing signs of recurrence. The attending physician has the discretion to determine how or when the compositions of this invention are to be used.

It is recognized in the art that the immunological status of each of the aforementioned category differs one from another by several criteria. For example, patients with active disease are generally immunosuppressed, either due to tumor-related pathology or to recent radiotherapy or chemotherapy. Their immune system may be under a barrage of tumor-associated antigen from the tumor site. On the other hand, patients who are in remission may have stronger active suppression against autoantigens. Accordingly, the ability of an anti-idiotype based vaccine to elicit an anti-tumor response, or improve the clinical condition, must be determined separately for each patient category.

Other Clinical Indications

Various compounds and compositions of this invention have other clinical indications, of which this section provides only a survey.

One indication is the treatment of cells ex vivo. This may be desirable for experimental purposes, or for treatment of an individual with a GD2-associated disease. In one example, the 1A7 antibody, or a polynucleotide or polypeptide derivative are administered to a culture of cells, such as peripheral blood cells obtained from a donor, or a suitable cell line. This may be done, for example, with the objective of stimulating T cell activity. About 0.5 to 2 µg/mL of 1A7 is an effective dose for this purpose. If desired, the stimulated cells may then be administered to a recipient, in an effort to convey passive immunity. In a second example, donor cells are genetically altered with an expression vector of this invention, to provide for ongoing secretion of 1A7 antibody after administration of the cells to the recipient.

The invention also encompasses compositions and methods using 1A7 antibodies and polypeptide derivatives to remove a label (particularly a radiolabel) from an individual who has received a labeled anti-GD2 antibody (such as 14G2a) in the course of radioscintigraphy or radiotherapy. Effective imaging using radiolabeled antibodies is hampered due to excess circulating radiolabeled antibody, which often takes several days to clear. Accordingly, 1A7 antibody or a polypeptide derivative is administered to the individual at a specified time after administration of the labeled anti-GD2. The intention is for the 1A7 polypeptide to complex with anti-GD2 at sites other than the tumor, such as in the circulation and interstitial spaces, and thereby promote its clearance. As a result, the level of label in unaffected tissues is reduced, and the image of the tumor (in comparison to neighboring tissues) is enhanced. Similarly, when radionuclides are given to subjects for irradiation of a tumor site, it is desirable to reduce collateral exposure of unaffected tissue. This invention thus includes methods of treatment in which a radiolabeled anti-GD2 antibody is administered in a therapeutic dose, and followed by a molar excess of 1A7.

In either of these applications, an amount of 1A7 polypeptide is chosen that is in sufficient molar excess over the labeled anti-GD2 to locate and bind any anti-GD2 that is not localized at the tumor site. The timing of administration and amount of 1A7 polypeptide will depend upon the nature of the radiolabeled antibody, the type of radioisotope used and the condition of the individual. Preferably, the molar ratio of 1A7 polypeptide to the anti-GD2 antibody is at least about 5:1, more preferably about 25:1 to 200:1. Preferably, 1A7 polypeptide is administered 5 to 24 hours after the individual has received the anti-GD2 antibody.

The invention also includes methods of detecting the presence of an anti-GD2 antibody bound to a tumor cell comprising the steps of treating an individual with 1A7 for a sufficient time to allow binding to the anti-GD2 antibody, and detecting the presence of any complex formed. The invention is for the 1A7 to detect anti-GD2 that has pre-attached to the tumor cell; or alternatively, to promote the binding of anti-GD2 to the tumor cell by forming a polyvalent anti-GD2/1A7 immune complex. In the former instance, the anti-GD2 is provided with a detectable label or a means by which a label can be attached. In the latter instance, either the anti-GD2 or the 1A7 is provided with a label. Suitable labels include radiolabels such as $^{111}$In, $^{131}$I and $^{99m}$Tc. The anti-GD2 and 1A7 are administered (usually sequentially) into the subject and allowed to accumulate at the tumor site. The tumor is then detected or visualized using standard techniques of radioscintigraphy.

Diagnostic Kits

The present invention encompasses kits containing 1A7 antibodies, polynucleotides, or polypeptides. Diagnostic procedures using the 1A7 polynucleotides or polypeptides of this invention can be performed by diagnostic laboratories, experimental laboratories, practitioners, or private individuals. Kits embodied by this invention include those that allow someone to conduct an assay for anti-GD2 or anti-1A7 activity, or for an 1A7 encoding sequence. An alteration in one of these components resulting, for example, from the presence of a GD2-associated disease or treatment directed towards it is typically compared with that in a sample from a healthy individual. The clinical sample is optionally pre-treated for enrichment of the target being tested for. The user then applies a reagent contained in the kit in order to detect the changed level or alteration in the diagnostic component.

Each kit necessarily comprises the reagent which renders the procedure specific: a reagent 1A7 antibody or polypeptide, used for detecting anti-1A7 or anti-GD2 in the sample; or a reagent 1A7 encoding polynucleotide, used for detecting a 1A7 encoding polynucleotide in the sample. Optionally, the reagent may be conjugated with a label to permit detection of any complex formed with the target in the sample. In another option, a second reagent is provided that is capable of combining with the first reagent after it has found its target. For example, labeled anti-mouse IgG may be provided as a secondary reagent for use with intact 1A7. Labeled avidin may be provided as a secondary reagent when the primary reagent has been conjugated with biotin.

The kits may be employed on a variety of biological samples, including both liquid samples, cell suspensions and tissue samples. Suitable assays using 1A7 antibodies, polypeptides, and polynucleotides that can be supplied in kit form include those described elsewhere in this disclosure.

Each reagent is supplied in a solid form or liquid buffer that is suitable for inventory storage, and later for exchange or addition into the reaction medium when the test is performed. Suitable packaging is provided. The kit may optionally provide additional components that are useful in the procedure. These optional components include buffers, capture reagents, developing reagents, labels, reacting surfaces, means for detection, control samples, instructions, and interpretive information.

Deposit

The foregoing description provides, inter alia, detailed methods for preparing monoclonal antibody 1A7, along with 1A7 encoding polynucleotides, 1A7 polypeptide fragments, and other derivatives.

A practitioner of ordinary skill in the art may practice embodiments of this invention by referring to the sequence data for 1A7, which is provided herein. Alternatively, a practitioner may practice the invention by first purifying the 1A7 antibody, or a 1A7 encoding polynucleotide from a 1A7 antibody producing cell. A hybridoma cell line producing 1A7 antibody has been deposited with the American Type Culture Collection (ATCC) under terms of the Budapest Treaty, and has been given Accession No. HB-11786.

The following examples are provided to illustrate but not limit the present invention.

STATEMENT OF DEPOSIT

A deposit of the hybridoma producing the 1A7 monoclonal antibody was made prior to the filing date of the above-identified patent application under the terms of the Budapest Treaty with the American Type Culture Collection, Parklawn Drive, Rockville, Md., USA, Accession No. HB-11786.

During the pendency of this application, access to the deposit will:

(a) be forwarded to one determined by the Commissioner to be entitled thereto;

(b) all restrictions imposed by the depositor on the availability to the public of the deposited material will be irrevocably removed upon the granting of the patent;

(c) the deposit will be maintained for a period of at least thirty years or at least five years after the most recent request for the furnishings of a sample of the deposited material; and (d) the deposit will be replaced should it become necessary due to inviability, containment or loss of capability to function in the manner described in the specification.

EXAMPLES

Example 1

Generation and Characterization of 1A7 Anti-Idiotype Antibody

The monoclonal anti-idiotype antibody producing hybridoma cell line 1A7 was created and identified according to the following description. Aspects of both the immunization procedure and the screening procedure were important to obtain an antibody with the desired specificity and functionality. 1A7 was one of a number of Ab2 that were initially produced, and was identified as the candidate with the most desirable features.

1A7 was obtained by using the 14G2a mouse monoclonal antibody as immunogen for an anti-idiotype response. 14G2a binds to a unique epitope of GD2 that is not present on other members of the ganglioside family. Since the responding animal was also a mouse, the Ab2 generated were expected to be directed against idiotypic features of 14G2a. However, only a fraction of those would be directed against the 14G2 paratope, an even smaller proportion would be immunogenic and able of eliciting an Ab3, and a still smaller proportion would elicit Ab3 that cross-reacted with the tumor-associated antigen.

To render 14G2a sufficiently immunogenic in an autologous species, it was conjugated to the carrier KLH, and emulsified in Freund's adjuvant. It was administered repetitively into the recipient animals on an unusual schedule with only 2 weeks between doses. Five mice were immunized according to this schedule. Substantial responses arose in about 3 mice only after the fourth immunization. Responding animals were boosted with a fifth dose of 14G2a intravenously., spleen cells were isolated, and hybridomas were prepared separately from each animal. Cloning was performed according to standard techniques.

The screening procedure comprised four important steps: (1) Positive selection for antibody binding to 14G2a; (2) Negative selection against antibody recognizing isotypic or allotypic determinants; (3) Positive selection for an ability to inhibit the binding of 14G2a to GD2; and (4) Positive selection for an ability to induce a humoral immune response against the original tumor-associated antigen (GD2) in both mice and rabbits. The rest of this section provides an overview of the screening procedure, which is given in more detail in the sections that follow.

Initial screening was conducted by immunoassay to identify the clones that reacted with 14G2a, but not with other target monoclonal antibodies sharing the same allotypic or isotypic determinants. A critical assay was a sandwich RIA in which 14G2a is attached to a solid phase, overlaid with culture supernatant, and developed with radioiodinated 14G2a. This assay requires the antibody in the hybridoma supernatant to be functionally bivalent, and be able to span between the capture 14G2a and the developing 14G2a. Several clones that were idiotype specific and gave a strong signal in this assay were selected for further study.

Subsequent screening was conducted by competition assays, in which the Ab2 was required to block the binding of 14G2a to GD2. This established that Ab2 recognized the paratope of 14G2a. GD2 was provided in the form of M21/P6 cells, a human melanoma cell line expressing GD2 at the cell surface. The nature of the assay requires the Ab2 to block the interaction between 14G2a and the tumor antigen in its particular manner of presentation on tumor cells. At a minimum, candidate Ab2 which had passed the earlier screening tests were required to inhibit the binding of 14G2a to the cells by at least 75%. There were about three Ab2 that substantially exceeded the minimum, with 1A7 providing about the highest level of inhibition.

The ultimate screening test was a determination of whether the candidate Ab2 were capable of eliciting an Ab3 of the desired specificity when injected into a recipient Sufficient quantities of Ab2 were prepared from mouse ascites, and tested in mice and rabbits. Sera from the test animals were first assayed for the presence of Ab3 in a sandwich immunoassay using the same labeled Ab2 used for immunization. Sera testing positively were then assayed for ability of the Ab3 to react against the tumor-associated antigen; namely GD2. A preparation of GD2 was used to coat microtiter plates, overlaid with the test serum in serial dilutions, and the Ab3 that bound was detected using labeled anti-immunoglobulin. The titer of the Ab3 binding to GD2 defined the "quality" of Ab2, as a reflection of its capacity as an inducer of anti-GD2.

Monoclonal antibody 1A7 emerged as the anti-idiotype with the highest quality, and is the original basis for various compounds, compositions, and procedures embodied in this invention. The cell line producing 1A7 was recloned twice by limiting dilution, to ensure the stability of the line.

Materials

Antibody: The hybridoma cell line producing monoclonal antibody 14G2a was obtained from the Scripps Research Institution. 14G2a has been subtyped as an IgG2aκ. The specificity of 14G2a was reconfirmed by immunoperoxidase staining and flow microfluorimetry analysis using cells expressing GD2. Other monoclonal and myeloma mouse immunoglobulins were used as controls in various experiments herein described.

Ascites of 14G2a hybridomas and other cell lines were prepared by injection individual Pristane-primed mice i.p. with $2-10 \times 10^6$ viable cells. The IgG fraction was isolated from ascites by 45% saturated ammonium sulfate precipitation and subsequent chromatography on Protein A SEPHAROSE™ CL-4B (Ey et al. (1978) Immunochemistry 15:429). The purity of the isolated IgG was checked by immunodiffusion, immunoelectrophoresis, and high pressure liquid chromatography (HPLC) fractionation.

Coupling of antibody with KLH: 14G2a was coupled to keyhole limpet hemocyanin (KLH) according to a method described by Maloney et al. (1985; *Hybridoma* 4:191). Antibody stock solution (1 mg/ml) was mixed with KLH (1 mg/ml) in PBS in the presence of freshly diluted glutaraldehyde solution (final concentration 0.05%). The mixture was rotated end-over-end for 1 h at room temperature, and then dialyzed exhaustively against PBS at 4° C.

Immunization of syngeneic BALB/c mice: BALB/c females were immunized four times over a period of 2 months. The first injection was given i.p. using 100 μg of 14G2a, emulsified in complete Freund's adjuvant. The next two injections were given with 100 μg of 14G2a coupled to KLH in incomplete Freund's adjuvant, either s.c. or i.p. Mice were bled from time to time, and sera were checked for anti-Id activity by ELISA in a binding assay by using F(ab')₂ fragments of 14G2a and normal pooled BALB/c mouse serum IgG as control. Three days before the fusion, the mice were boosted i.v. with 14G2a in PBS.

Production of Anti-Idiotype Hybridomas

The fusion partner used to produce the hybridoma lines was the mouse non-secretory myeloma cell line P3-653, ancestrally related to P3X63Ag8.653, available from the ATCC as No. CRL-1580. Established human cell lines were cultured in RPMI 1640 supplemented with 5% fetal calf serum as described elsewhere (Seon et al. (1984) J. Immunol. 132:2089).

Hybridomas were produced essentially following the method of Oi and Herzenberg ((1980) *Selected Methods of Cellular Immunology*, Mishell & Shiigi eds., Freeman Publs., at 351-372). Spleen cells from immunized mice were mixed with P3-653 cells at a ratio of 1:1 to 10:1, in the presence of 50% polyethylene glycol (PEG, mw ~4500). Fused cells were then washed and cultured Hybrids were selected using hypoxanthine-aminopterin-thymidine media.

Initial Selection of Anti-Idiotype Antibody (Ab2) Secreting Hybridoma Clones:

Initial screening of the hybridoma clones was performed by RIA. Purified 14G2a was radioiodinated by the Chloramine T method (Hunter (1970) Proc. Soc. Exp. Biol. Med. 133:989). The assay was conducted by coating microtiter plate wells with 14G2a antibody (or control) at 500 ng/well. After incubating overnight at 4° C., the plates were blocked with 1% bovine serum albumin (BSA) in PBS. 100 μl of hybridoma culture supernatants or 20× concentrate was incubated in the well for 4 h at room temperatures After washing with PBS, the plates were further incubated for 4 h at room temperature or overnight at 4° C. with labeled 14G2a, washed, and counted. This RIA is a stringent test for antibody specificity, since it requires that the antibody be able to span between two 14G2a molecules.

An ELISA was conducted in a similar fashion, using subclass-specific anti-immunoglobulin as both the plate coat and detecting reagent. Generally, antibody of certain IgG subclasses is desired because it is stable, easily purified by protein A chromatography, and may have useful effector functions.

A number of monoclonal Ab2 secreting cell lines emerged from these screening assays with the desired properties. Amongst them was monoclonal antibody 1A7.

Confirmation that Ab2 are Specific for 14G2a Idiotype

Idiotype specificity of Ab2 was confirmed by direct binding to Ab1. Various purified Ab2 were labeled with $^{125}$I, and tested for binding to plates coated with a panel of monoclonal anti-TAA Ab1. 1A7 bound almost exclusively to 14G2a; there was virtually no cross-reactivity with any of the other Ab1 tested.

Specificity for the 14G2a idiotype was further established in competition experiments. ~25,000 cpm of various labeled Ab2 was mixed with different members of a panel of unlabeled competitors comprising Ab2, Ab1, and other mouse immunoglobulins. The Ab2 was then tested for binding to 14G2a coated plates. For the best Ab2, greater than 90% inhibition was obtained using either Ab2 or 14G2a as competitor. Virtually no inhibition was obtained, up to a concentration of 5 μg, using control immunoglobulins as potential competitors.

Screening for Anti-Idiotypes Directed Against the 14G2a Paratope

To determine whether the Ab2 were directed against the paratope of 14G2a, the Ab2 were used to compete for the binding of radiolabeled 14G2a to GD2. This was performed conducted using M21/P6 cells, a human cancer cell line expressing GD2 as a membrane constituent.

To conduct the assay, M21/P6 cells were grown as confluent monolayer in 96-well tissue culture plates. Various dilutions of the test Ab2 (either culture supernatant or purified antibody) were mixed with the labeled 14G2a, and then added to the cultured cells. Percent inhibition of the assay was calculated according to the formula:

$$\% \text{ inhibition} = \left[1 - \left(\frac{R_T - R_C}{R_{\text{MAX}} - R_C}\right)\right] \times 100\%$$

where $R_T$ is the average cpm of the experimental well with inhibitors; $R_C$ is the average background cpm; and $R_{MAX}$ is the average maximum binding without any inhibitors.

Three Ab2, including 1A7, inhibited the binding of labeled 14G2a to the GD2 expressing cells at amounts as low as about 25 ng. Purified control antibody demonstrated no inhibition.

Antibody-producing clones testing positively in the screening tests described so far were used to prepare mouse ascites as a source of Ab2. The Ab2 were purified by chromatography using Protein A and Protein G affinity resins by standard techniques.

Screening for Anti-Idiotypes Capable of Eliciting a Tumor-Specific Immune Response Since a central purpose of these experiments was to find an anti-idiotype capable of eliciting an anti-GD2 immune response, the next screening step was to test its immunogenicity in animal models. The Ab2 would have to be not only immunogenic, but capable of raising Ab3 that cross-reacted back to the tumor antigen GD2.

Accordingly, the monoclonal antibody that gave the strongest result in the competition experiments with the GD2-expressing cells was brought forward for testing in this part of the study. The other two antibodies showing specific inhibition were held in reserve in case 1A7 failed to demonstrate the desired properties in this test.

Accordingly, 1A7 was prepared as a vaccine composition and injected into test animals. First, syngeneic BALB/c mice (6~8 weeks old) were immunized with 50 μg of 1A7 coupled to the carrier KLH (1:1 ratio) in the presence of equal volume (0.1 ml) of Freund's Complete or Incomplete adjuvant on days 0, 14, 28, and 42, subcutaneously. Blood samples were drawn from each mouse 10 days after the 4th immunization and analyzed for total Ab3 response (anti-iso/allo/idiotypic) by sandwich RIA and anti-anti-idiotypic response by the inhibition of Ab1 (14G2a) binding to Ab2 (1A7 on the plate) by Ab3 sera. In addition, serum was checked for inhibition of $^{125}$I-14G2a binding to GD2 positive melanoma cells (M21/P6). Also, direct binding of sera to purified GD2, coated onto microtiter plate, was determined by ELISA assay. Representative date from 3 BALB/c mice are shown in Table 1

TABLE 1

Results of immunizing BALB/c Mice with 1A7-KLH

| Assay | Serum Dilution | Mouse #1 | Mouse #2 | Mouse #3 |
|---|---|---|---|---|
| Sandwich RIA (CPM) | 1:50 | 16.700 | 24.576 | 26.214 |
| % Inhibition of Ab1-Ab2 Binding by Ab3 Sera | 1:50 | 87 | 95 | 97 |
| % Inhibition of Ab1 Binding to M21/P6 Melanoma Cells | 1:50 | 28 | 32 | 27 |
| Direct Binding to GD2 by ELISA (OD405 nm) | 1:10 PBS-BSA Control 0.08 | 0.70 | 0.76 | 0.71 |

There was no reactivity with GD2 negative cell lines or unrelated gangliosides such as GD3 and GM3. Results are expressed as mean value of triplicate determinations (S.D.<10%).

Next, allogeneic C57BL/6 mice (6~8 weeks old) were immunized with three different formulations of anti-id 1A7 vaccine: (I) 1A7-KLH+Freund's Adjuvant; (ii) 1A7-KLH+QS-21 (10 μg per mouse); (iii) 1A7+QS-21 (10 μg per mouse). Results shown in Table 2.

TABLE 2

Humoral Immune Response

| Immunized with | Sandwich RIA of Ab3 Sera (1:50 dilution) cpm | % Inhibition of Ab1-Ab2 Binding by Ab3 Sera (1:50 dilution) | % Inhibition of Ab1 Binding to M21/P6 Melanoma Cells by Ab3 Sera (1:50 dilution) | Direct Binding of Ab3 Sera (1:10 dilution) to GD2 by ELISA (OD 405 nm) |
|---|---|---|---|---|
| 1A7-KLH + Freunds | | | | |
| Mouse #1 | 4,729 | 80 | 27 | 1.28 |
| Mouse #2 | 6,067 | 83 | 14 | 0.62 |
| Mouse #3 | 9,391 | 96 | 13 | 0.41 |
| PBS-BSA Control | 650 | — | — | 0.10 |
| 1A7-KLH + QS-21 | | | | |
| Mouse #1 | 5,506 | 79 | 37 | 0.64 |
| Mouse #2 | 5,831 | 95 | 38 | 0.63 |
| Mouse #3 | 7,315 | 94 | 43 | 0.63 |
| PBS-BSA Control | 549 | — | — | 0.09 |
| 1A7 + QS-21 | | | | |
| Mouse #1 | 847 | 70 | 73 | 0.66 |
| Mouse #2 | 738 | 77 | 79 | 0.62 |
| Mouse #3 | 1,000 | 74 | 80 | 0.64 |
| PBS-BSA Control | 153 | — | — | 0.09 |

Results are expressed as mean value of the triplicate determinations (S.D.<10%). There was no reactivity with GD2-negative cell lines or unrelated gangliosides, such as GD3 and GM3.

Comparison between the three vaccine preparations suggests that in C57BL/6 allogeneic mice 1A7-KLH and Freund's adjuvant induced almost identical humoral immune responses as 1A7-KLH and QS-21. The production of total Ab3 response was less in 1A7+QS-21 immunized mice; however, the binding of Ab1 to melanoma cells was inhibited much more strongly and the production of anti-GD2 antibodies (Ab1') was comparable to the other two groups. Thus, there was no additional advantage of coupling of KLH to 1A7. KLH apparently induced strong anti-isotypic and antiallotypic responses in C57BL/6 mice. Immune mice sera at 1:100 dilution reacted strongly with M21/P6 melanoma cells and EL4 lymphoma cells, but not with the unrelated colon carcinoma LS174-T cells by FACS analysis.

The T cell responses of the spleen cells were also compared from the differently immunized groups of mice to various stimuli by T-cell proliferation assay. Representative data from all three groups of C57BL/6 mice and BALB/c mice are presented in Table 3.

with 1A7-KLH+Freunds', 1A7-KLH+.QS-21 and 1A7+QS-21 were given intradermal foot pad injection of irradiated M21/P6 cells or irradiated LS174-T (control) cells. In another experiment, mice received intradermal foot pad injection of purified GD2 or purified GD3. Mice were observed for development of DTH response at the inoculation site at 24 hours and 48 hours. There were significant DTH responses directed at GD2-positive M21/P6 cells but not GD2-negative LS174-T cells in all three groups of immunized mice (data not shown).

TABLE 3

| | T cell proliferation | | | |
|---|---|---|---|---|
| | 1A7-KLH + Freunds (BALB/c) | 1A7-KLH + Freunds (C57BL/6) | 1A7-KLH + QS-21 (C57BL/6) | 1A7 + QS-21 (C57BL/6) |
| Stimulant | CPM (S.I.) | CPM (S.I.) | CPM (S.I.) | CPM (S.I.) |
| Anti-id 1A7 (2 μg) | 10,919 (15.1) | 4,428 (4.4) | 8,288 (6.3) | 5,629 (4.3) |
| Anti-id 3H1, Control 2 μg) | 8,451 (10.1) | 1,468 (1.4) | 5,296 (4.0) | 3,235 (2.4) |
| M21/P6 irradiated Melanoma Cells ($1 \times 10^6$) | 29,671 (35.5) | 9,648 (9.5) | 17,753 (13.5) | 27,739 (21.0) |
| EL4 Murine Lymphoma Irradiated Cells ($1 \times 10^6$) | n.d. | 12,037 (11.8) | 17,528 (13.3) | 12,999 (9.8) |
| LS174-T Control Colon Carcinoma Irradiated Cells ($1 \times 10^6$) | 2,973 (3.5) | 2,074 (2.0) | 3,944 (3.0) | 2,340 (1.7) |
| GD2 (1 μg) | 514 (0.6) | 2,121 (2.1) | 2,932 (2.2) | 2,520 (1.9) |
| GD3 (1 μg) | 290 (0.3) | 1,346 (1.3) | 1,180 (0.9) | 1,285 (0.9) |
| Medium | 834 (1.0) | 1,015 (1.0) | 1,313 (1.0) | 1,320 (1.0) |

The data are expressed as mean CPM of triplicate wells (S.D.<10%). S.I.=Stimulation Index. S.I.>3.0 was arbitrarily considered as positive.

The results indicated that in C57BL/6 mice, immunization with all three regimens induced 1A7 specific, M21/P6 melanoma cell specific and EMA cells specific proliferative responses, some reactivity against control 3H1 and no reaction against control cell line LS174-T cells or ganglioside GD2 or GD3. These data support the postulate that for T cell activation, GD2 needs to be associated with cell surface oligopeptides. There was also no significant difference in Stimulation Index obtained with any of these three regimens. 1A7+ QS-21 was as good as 1A7-KLH+QS-21 or 1A7-KLH+ Freunds in C57BL/6 mice.

In order to assess the ability of these vaccines to induce T-cell mediated DTH response, C57BL/6 mice immunized There was, however, no DTH reactivity directed at GD2 or GD3 in any of the groups of immunized mice.

Rabbits were selected next for the immunization studies with 1A7-KLH+QS-21 and 1A7+QS-21. The relative composition and tissue distribution of gangliosides in rabbits is similar to that of humans. Each group of three rabbits were immunized with either 500 μg of 1A7 mixed with 50 μg of QS-21, or 500 μg of 1A7-KLH+50 μg of QS-21. The injections were given intramuscularly on days 0, 14, 28 and 42. Blood samples were collected 10 days after the fourth immunization, and analyzed for Ab3 (Ab1') responses and T-cell proliferation. Table 4 shows the humoral immune response induced.

TABLE 4

| | Binding studies using rabbit serum | | | | | |
|---|---|---|---|---|---|---|
| | | 1A7-KLH + QS-21 Rabbit Nos. | | | 1A7 + QS-21 Rabbit Nos. | |
| Assays | ® Serum Dilution | #4819 | #4821 | #4823 | #4818 | #4820 | #4822 |
| Sandwich RIA (CPM) | 1:50 | 101,313 | 107,219 | 100,157 | 72,554 | 100,837 | 52,702 |
| % Inhibition of Ab1-Ab2 Binding by Ab3 | 1:50 | 45 | 52 | 56 | 72 | 65 | 79 |
| % Inhibition of Ab1 Binding to M21/P6 Melanoma Cells | 1:100 | 33 | 41 | 37 | 42 | 35 | 44 |
| Direct Binding to GD2 by ELISA (OD 450 nm) | 1:10 | 0.64 | 0.59 | 0.18 | 0.95 | 0.17 | 1.75 |

Results are expressed as the mean value of triplicate determinations (S.D.<10%). There was no reactivity with GD2-negative cell lines or the gangliosides GD3 or GM3. The O.D. value obtained with PBS-BSA control was 0.08.

KLH-coupled 1A7 plus QS-21 induced higher levels of anti-isotypic and anti-allotypic responses in all three rabbits. Ab3 and GD2-positive cell binding inhibition reactions were better in all three 1A7+QS-21 immunized rabbits. Two out of 3 rabbits in each group raised anti-GD2 antibodies, and the response was better in 1A7+QS-21 immunized group as compared to 1A7-KLH+QS-21 group.

Thus, 1A7+QS-21 was capable of raising desired anti-tumor responses in both mice and rabbits. There was no additional advantage of coupling 1A7 to KLH. The isotype of the anti-GD2 antibodies in the rabbit sera was mostly of IgG type with trace amount of IgM. The Ab1' antibody in rabbit sera also reacted with melanoma cells but not with GD2-negative carcinoma cells by FACS analysis.

The Ab3 sera were cytotoxic to M21/P6 and EL4 cells by in vitro ADCC assay, conducted as described elsewhere in this disclosure. Briefly, target cells were labeled with $^{51}Cr$, washed thrice with DMEM without FCS and suspended in growth medium. $10^4$ target cells in 25 μL were added to microtiter plate wells and incubated with different dilutions of sera from immunized animals and effector cells. The immune sera induced 30-40% specific lysis of the target cells.

PBL were isolated from immunized rabbits and used to study the cellular immune response in a PBL-transformation assay. Results are shown in Table 5.

TABLE 5

T Cell Proliferation Assay of Rabbit PBL

| Stimulant | 1A7-KLH + QS-21 | | 1A7 + QS-21 | |
|---|---|---|---|---|
| | CPM | Stimulation Index | CPM | Stimulation Index |
| Anti-id 1A7 (2 μg) | 21,329 | 4.42 | 9,794 | 4.92 |
| Anti-id 3H1 Control (2 μg) | 11,550 | 2.39 | 5,691 | 2.85 |
| M21/P6 Melanoma Cells (1 × 10⁶), Irradiated | 71,596 | 14.86 | 28,845 | 14.48 |
| EL4 Murine Lymphoma Cells (1 × 10⁶), Irradiated | 44,619 | 9.26 | 28,040 | 14.08 |
| LS174-T Colon Carcinoma Cells (1 × 10⁶), Irradiated | 5,196 | 1.07 | 3,131 | 1.57 |
| GD2 (1 μg) | 11,345 | 2.35 | 5,988 | 3.00 |
| GD3 (1 μg) | 7,329 | 1.52 | 4,678 | 2.34 |
| Medium | 4,816 | 1.0 | 1,991 | 1.0 |

Results are expressed as the mean value of triplicate determinations (S.D.<10%). Stimulation Index >3.0 was considered as positive.

The results demonstrate that immunization of rabbits with both 1A7-KLH+QS-21 and 1A7-S-21 induced T cell proliferation in PBL against anti-Id 1A7, irradiated GD2-positive M21/P6 cells and ELM cells but not against GD2-negative LS174-T cells or against GD2 and GD3. There was insignificant stimulation against normal isotype-matched control Ab2 (S.I.<3.0). Stimulation Index against various stimuli was almost identical in both groups of immunized rabbits.

Rabbits immunized with 1A7 were subjected to skin testing to confirm that the cellular response induced by administration of 1A7 can mediate a hypersensitivity response. The rabbits were shaved on the back and challenged with an intradermal inoculum of purified gangliosides. Slight erythema and induration was observed as a result of challenge with either GD2 or GD3. In a separate experiment, immunized rabbits were challenged with an intradermal inoculum of $1×10^6$ cells inactivated by irradiation at 12,000 rads. In a rabbit immunized with 1A7+QS-21 and challenged with M21/P6 cells (a GD2-expressing line), the induration was 13×12 mm at 24 h and 18×13 mm at 48 h. In a rabbit immunized with 1A7-KLH+QS-21 and challenged with M21/P6 cells, the induration was 18×16 mm at 24 h and 24×16 mm at 48 h. In contrast, when challenged with LS174-T cells (a GD2-negative line), the induration was 4×4 mm and 5×3 mm respectively at 24 h, and negligible at 48 h.

Example 2

Obtaining the 1A7 Heavy and Light Chain Sequences

The polynucleotide sequence was obtained for the 1A7 antibody by isolating messenger RNA from the 1A7 producing cell line. For each sequence determination, total RNA was isolated from $1×10^7$ 1A7 hybridoma cells. Messenger RNA was prepared by passage through two cycles of chromatography of oligothymidylate-cellulose columns. The yield of mRNA was about 10 μg. First strand cDNA was synthesized using SUPERSCRIPT™ Preamplification kit (GIBCO/BRL).

To sequence the heavy chain variable region, PCRs were conducted on the cDNA using a reverse primer corresponding to amino acids 126 to 119 of the murine $\gamma_1$ constant region:

(SEQ. ID NO:46)
5'-CCCAAGCTTCCAGGGRCCARKGGATARACIGRTGG -3' and various mixtures of forward primers, corresponding to the N-terminal leader sequences of murine variable region subgroups. The forward primer that gave a positive reaction was:

(SEQ. ID NO:47)
5'-ACTAGTCGACATGGCTGTCYTRGBGCTGYTCYTCTG-3' corresponding to amino acids −20 to −12.

The amplified fragment of cDNA was subcloned into pT7 plasmid and NOVABLUE™ competent cells were transformed using a protocol provided by the supplier (Novagen). Recombinant colonies were picked up by color selection and plasmid DNA was prepared by miniprep procedure. The DNA sequence of the double stranded plasmid was determined using a Sequenase Version 2.0 kit (USB, Cleveland, Ohio). The sequence of the DNA insert in the plasmid was determined from both orientations using primers specific for the plasmid; namely T7 promoter (TAATACGACTCACTAT-AGGG) (SEQ. ID NO:48) and U-19 (GTTTTCCCAGT-CACGACGT) (SEQ. ID NO:49). At least 8 clones were picked for sequence determination.

The sequence of the 1A7 light chain variable region was determined in a similar fashion. The forward and reverse primers giving a positive result in the PCR were:

```
                                                        (SEQ.ID NO:50)
5'-ACTAGTCGACATGAAGTTGCCTGTTAGGCTGTTGGTGCT-3'

(SEQ.ID NO:51)
5'-CCCAAGCTTACTGGATGGTGGGAAGATGGA-3'
``` corresponding to amino acids −19 to −10 of the leader sequence, and 122 to 116 of the mouse κ chain constant region.

In order to minimize the error rates in PCR amplification, pfu DNA polymerase (Stratagene, San Diego) was used for amplification in all subsequent experiments. Mutant frequency with this thermostable DNA polymerase is 1/10 compared to Taq DNA polymerase.

Confirmation that the isolated cDNA correspond to the 1A7 heavy and light chains is obtained by amino acid sequencing of the N-terminal of the isolated antibody. Fifty μg of purified 1A7 antibody is diluted with sample loading buffer (50 mM Tris-HCl, pH 6.8, 1% SDS, 1% glycerol, 0.1% β-mercaptoethanol) and heated to 100° C. for 3 minutes. The denatured protein is loaded onto a 7.5% polyacrylamide gel (BioRad Miniprotean II Dual Slab Cell) containing SDS and subjected to electrophoresis at 200 V for 1 hour. Proteins in the gels are transferred to polyvinylidene difluoride (PVDF) membranes by the procedure described by Towbin et al. ((1979) Proc. Natl. Acad. Sci. USA. 78: 4350-4354) at 150 mA overnight. The transfer buffer contains 25 mM Tds, 192 mM glycine, 20% (vNt) methanol. The membranes are stained by quick dipping in 0.1% Coomassie Brilliant Blue in 50% methanol-50% acetic acid, followed by washing in a solution containing 40% methanol plus 10% acetic acid. After drying the membrane at room temperature, the stained heavy and light chain bands are excised with a clean razor blade. The proteins on the membrane slices are subjected to N-terminal microsequencing by automated Edman degradation using an Applied Biosystem Model 477A protein sequencer employing pulsed-liquid chemistry and on-line phenyl-ethiohydantion amino acid identification. Each protein is subjected to 10-15 degradative cycles and the converted cleavage products from each cycle were analyzed by reverse-phase HPLC The nucleic acid sequence and the corresponding translation for the heavy and light chain variable regions of monoclonal antibody 1A7 is shown in FIGS. 1 and 2.

The heavy and light chain polynucleotide and amino acid sequences were compared using the BLAST algorithm at the National Center for Biotechnology. Information with sequences available from the PDB, SwissProt, PIR, SPUpdate, GenPept, and GPUpdate databases. The comparison was performed on Dec. 16, 1995.

FIG. 17 shows the ten most closely matched polynucleotide sequences to the 1A7 light chain variable region encoding sequence. FIG. 18 shows the ten most closely matched polynucleotide sequences to the 1A7 heavy chain variable region encoding sequence.

FIG. 3 is a comparative depiction of the 1A7 light and heavy chain amino acid sequence with the 15 closest sequences found in the BLAST search. Panel (A) shows the light chain comparison. Panel (B) shows the heavy chain comparison. The database identifiers for the matched sequences are shown in Table 6:

TABLE 6

Matched immunoglobulin amino acid sequences

Light Chain Variable Region

| | | |
|---|---|---|
| 1 | gp| M34588|MU SIGKABR_1 | Mouse Ig kappa-chain mRNA V-J regi . . . |
| 2 | gp| L18941|MU SIG438B_1 | Mouse rearranged immunoglobulin li . . . |
| 3 | gp| Z22035|MD IGKVAH_1 | immunoglobulin variable region [Mu . . . |
| 4 | gp| M32857|MU SIGKCSP_1 | Mouse Ig rearranged kappa-chain mR . . . |
| 5 | gp| M34589|MU SIGKABS_1 | Mouse Ig kappa-chain mRNA V-J regi . . . |
| 6 | gp| J04438|MUSIGKCWA_1 | Mouse Ig-kappa chain (PAC1) mRNA V . . . |
| 7 | gp| M31271|MUSIGKCSM_1 | IgM gene product [*Mus musculus*] |
| 8 | gp| M32858|MUSIGKCSQ_1 | Mouse Ig rearranged kappa-chain mR . . . |
| 9 | gp| U29428|MMU29428_1 | anti-PC Ig kappa chain [*Mus musculus*] |
| 10 | gp|X65770|MMIGMMM4_1 | IgM gene product [*Mus musculus*] |
| 11 | gp|M83723|MUSIGKD2A_2 | immunoglobulin kappa-chain VK-1 [M . . . |
| 12 | pir|B39276|B39276 | Ig light chain precursor V-D-J reg . . . |
| 13 | gp|L14370|MUSIGKJVSA_1 | immunoglobulin kappa chain [*Mus mu* . . . |
| 14 | pir|A31807|A31807 | Ig kappa chain V region (PAC1) - m . . . |
| 15 | gp|U29267|MMU29267_1 | IgL rearranged kappa chain V-J reg . . . |

Heavy Chain Variable Region

| | | |
|---|---|---|
| 1 | gp|M36221|MUSIGHAEB_1 | immunoglobulin heavy chain V-region |
| 2 | gp|U01185|MMU01185_1 | immunoglobulin heavy chain [*Mus mu* . . . |
| 3 | sp|P01819|HV43_MOUSE | IG HEAVY CHAIN PRECURSOR V REGION . . . |
| 4 | gp|M26985|MUSIGH1PR_2 | Igh gene product [*Mus musculus*] |
| 5 | gp|M36217|MUSIGHADX_1 | immunoglobulin heavy chain V-regio . . . |
| 6 | gp|M36228|MUSIGHAEI_1 | immunoglobulin heavy chain V-regio . . . |
| 7 | gp|M34626|MUSIGHACK_1 | Mouse Ig rearranged heavy chain (N . . . |
| 8 | gp|A05515|A05515_1 | Vector pSW2HPOLY DNA sequence. [un . . . |
| 9 | pdb|1FDL|H | IgG1 Fab Fragment (Anti-Lysozyme A . . . |
| 10 | gp|L43544|MUSALCA_1 | antibody [*Mus musculus*] |
| 11 | gp|A03907|A03907_1 | antibody D1.3 V region (VDJ) [*Homo* . . . |
| 12 | pir|S38563|S38563 | Ig heavy chain V region (ASWS1) - . . . |
| 13 | pir|A32456|A32456 | Ig heavy chain precursor V region . . . |
| 14 | gp|A05504|A05504_1 | pSW1 protein [unidentified] >gp|A0 . . . |
| 15 | gp|L43544|MUSALCA_3 | *Mus musculus* (clone pCT.kvhd1) ant . . . |

Amongst the 50 database sequences matched most closely to that of the 1A7 light chain variable region, none was identical. 1A7 differed from the five closest sequences by 2 substitution differences at residues 50 and 55, which are contained in the second complementary determining region (CDR2). The two differences at these positions were non-conservative substitutions, and persisted in comparisons with other light chain sequences.

Amongst the 50 database sequences matched most closely to that of the 1A7 heavy chain variable region, none was identical. The following summarizes the main points deduced from the comparison.

The closest match was with a heavy chain fragment beginning at residue 9 (designation gp|M36221|MUSIGHAEB_1). There were 6 substitutions between residues 1 and 97 (before the VDJ junction), 6 substitution differences after residue 97, and 1A7 was shorter about the VDJ junction by 2 residues.

The closest match with a full length heavy chain variable region had the following features (designation gp|01185|MMU01185): There were 10 substitution differences between residues 1 and 97, 7 substitutions after residue-97, and 1A7 was shorter about the VDJ junction by 3 residues.

1A7 differed in length from all sequences but one, due to insertions or deletions of 1 to 8 residues about the VDJ junction. For the sequence of equal length (designation pir|S11106|S11106), there were 18 substitution differences between residues 1 and 97, and 8 substitutions after residue 97.

All other comparisons showed at least 14 substitution differences between residues 1 and 97.

All other comparisons showed at least 4 substitution differences after residue 97.

All other comparisons showed a total of at least 22 insertions, deletions and substitution differences.

Differences appeared throughout the variable region.

Amino acid consensus sequences of the 15 most closely matched $V_L$ and $V_H$ regions were designed, and compared with the 1A7 sequences. This is shown in FIG. 3(C). Other than splicing differences about the VDJ junction, there appear to be about 16 differences between 1A7 and the prototype sequences. Two of these differences are present in the light chain; 14 are present in the heavy chain. Seven occur in the CDRs, while nine occur in the variable region framework. The point differences likely have arisen from somatic mutation of germline variable region sequences.

Example 3

1A7 as an Immunogen in Non-Human Primates

As a model more closely related to humans, the effect of anti-Id 1A7 on the induction of GD2-specific humoral responses was investigated in cynomolgus monkeys (*Macaca fascicularis*). The normal tissue distribution of GD2 in cynomolgus monkeys is very similar to that in humarn. As such, this primate model is ideal to gauge toxicities induced by these agents and to establish useful dosage for initial clinical trials.

Cynomolgus monkeys (two per group, 2-4 kg weight) received four intramuscular injections of purified Ab2 (2 mg) mixed with 100 μg of QS 21 as adjuvant. Control monkeys were immunized with unrelated Ab2, 3H1 mixed with QS 21 in the similar way. All injections were given at 2-week intervals. Monkeys were bled 10 days after each immunization.

The sera were analyzed for Ab3 responses by sandwich RIA and inhibition of Ab2 binding to Ab1. For these assays, the sera were pretreated with normal mouse immunoglobulin (500 μg/ml) to block anti-isotypic and antiallotypic reactivities. 250 ng of 1A7 (Ab2) was coated into 96-well plate. After blocking, 50 μl of different concentrations of PRO#685 or PRO#778 (Ab3) was added and incubated 2 h at room temp with shaking. After washing, 90,000 cpm of $^{125}$I-1A7 was added to each well and incubated 1.5 h at room temp. The plate was then washed and bound radioactivity was measured.

Results are shown in FIG. 4. Ab3 sera from monkeys (PRO 685 and PRO 778) immunized with 1A7 bound specifically to the immunizing Ab2 (1A7) with minimal reactivity with unrelated Ab2 (3H1).

FIG. 5 shows that monkey Ab3 sera also inhibited the binding of radiolabeled Ab2 to Ab1 500 ng of 1A7 (Ab2) or 14G2a (Ab1) was coated into 96-well plate. After blocking, 50 μl of different concentrations of PRO#685 (Ab3) along with 50 μl of $^{125}$I-14G2a or $^{125}$I-1A7 (90,000 cpm) where added to each well. After 1.5 h incubation, plates were washed and bound radioactivity was counted. There was no inhibition with preimmune sera or sera obtained from monkeys (PRO 541 and PRO 667) immunized with the unrelated Ab2 3H1. These results indicate that monkey Ab3 sera share idiotypes with the Ab1.

To measure anti-GD2 reactivity in the serum of immunized monkeys, purified GD2 (250 ng/well) was absorbed into 96-well plates. After blocking wells with 1% BSA in PBS, test serum and Ab1 were diluted in same buffer and added to wells and incubated overnight at room temp. After washing, the bound antibodies were detected using alkaline phosphatase labeled anti-mouse or anti-human Ig reagents as second antibodies. Sera from both monkeys tested positively.

To determine whether 1A7 immunized monkey sera bound specifically to GD2 positive melanoma cells, the binding of monkey Ab3 sera to the melanoma cell line M21/P6 was tested M21/P6 cells ($2 \times 10^6$) were incubated with different concentrations of PRO#685, PRO#778 (Ab3) or 14G2a (Ab1), and the amount of bound antibody was determined.

Figure 6:
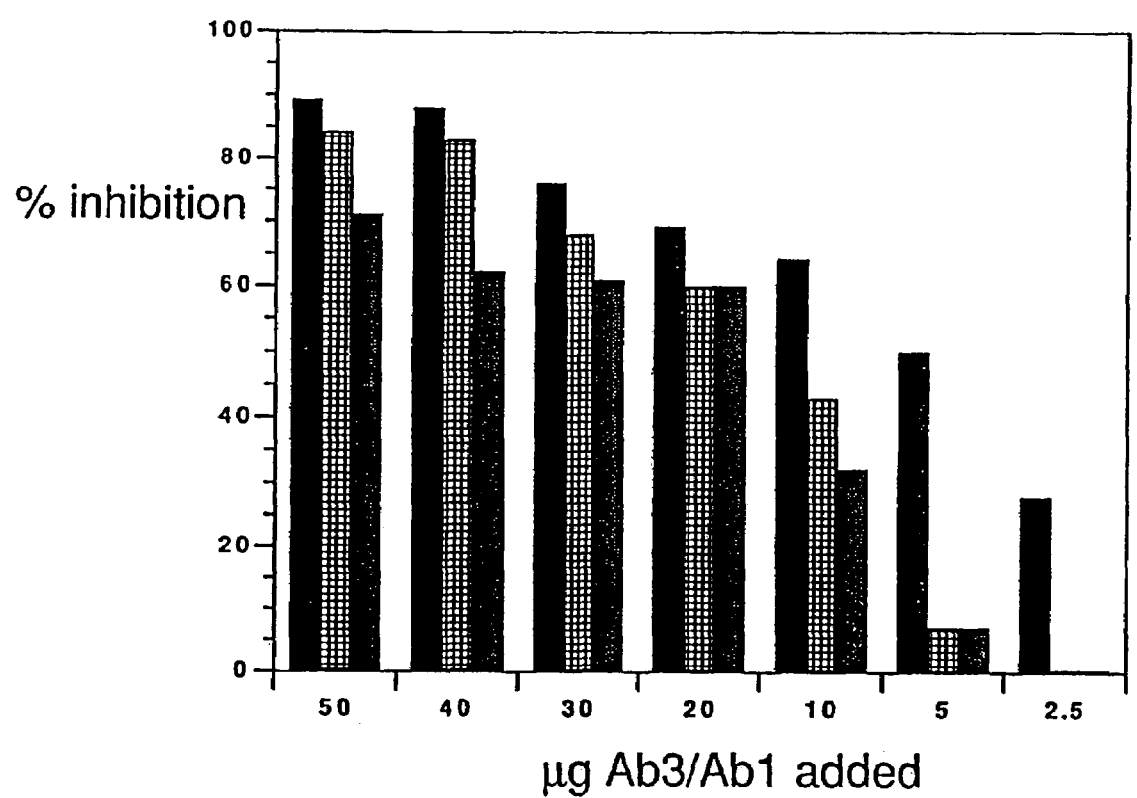
FIG. 6 is a bar graph depicting inhibition of binding of $^{125}$I labeled 14G2a antibody to GD2 positive melanoma cell line M21/P6 in the presence of different concentrations of Ab1 and monkey Ab3. Parallel inhibition curves were obtained using either purified Ab1 or Ab3 from monkey sera. For each triad of bars, the left hand bar denotes control binding with 14G2a; the middle (hatched) bar denotes binding of Ab3 from monkey PRO#685; the right hand bar denotes binding of Ab3 from monkey PRO#778.

FIG. 6 shows the sera collected after the fourth immunization, reacted with melanoma cells but not with the antigen-negative MCF-7 breast cancer cell line. The Ab3 sera also bound specifically to purified GD2 coated onto microtiter plates by ELISA. Control sera from preimmune monkeys or monkeys immunized with unrelated Ab2 (3H1) did not show appreciable binding to GD2. In parallel experiments, the same Ab3s from monkey PRO 685 were compared on a plate coated with CEA (an unrelated tumor-specific antigen) and were negative.

The Ab3 antibodies were then purified from sera by absorption and elution from the affinity column made of antibody 1A7 coupled to SEPHAROSE™ 4B. The eluted antibody was then passed over an immunoadsorbent column consisting of normal mouse Ig coupled to SEPHAROSE™ 4B to remove anti-isotypic and anti-allotypic reactivities. Antibody that passed through was concentrated and used as purified Ab3. The purified Ab3 from monkey sera were then compared with the reactivity of purified Ab1 (14G2a) in different assays. 2.6 mg of purified Ab3 were recovered from 10 ml of sera (i.e. about 260 μg of Ab3 per ml of serum) from monkey # PRO 685 and a little less from monkey # PRO 778.

Binding of Ab3 to M21/P6 cells was analyzed by flow cytometry. Target cells M21/P6 or control cells MOLT-4 ($5 \times 10^5$ in PBS supplemented with 0.2% BSA) were incubated with different dilutions of Ab3 and Ab1 for 1 h at 4° C.

After washing with PBS, the staining was done with FITC labeled second antibody and analyzed on a FACScan flow cytometer.

Figure 7A:
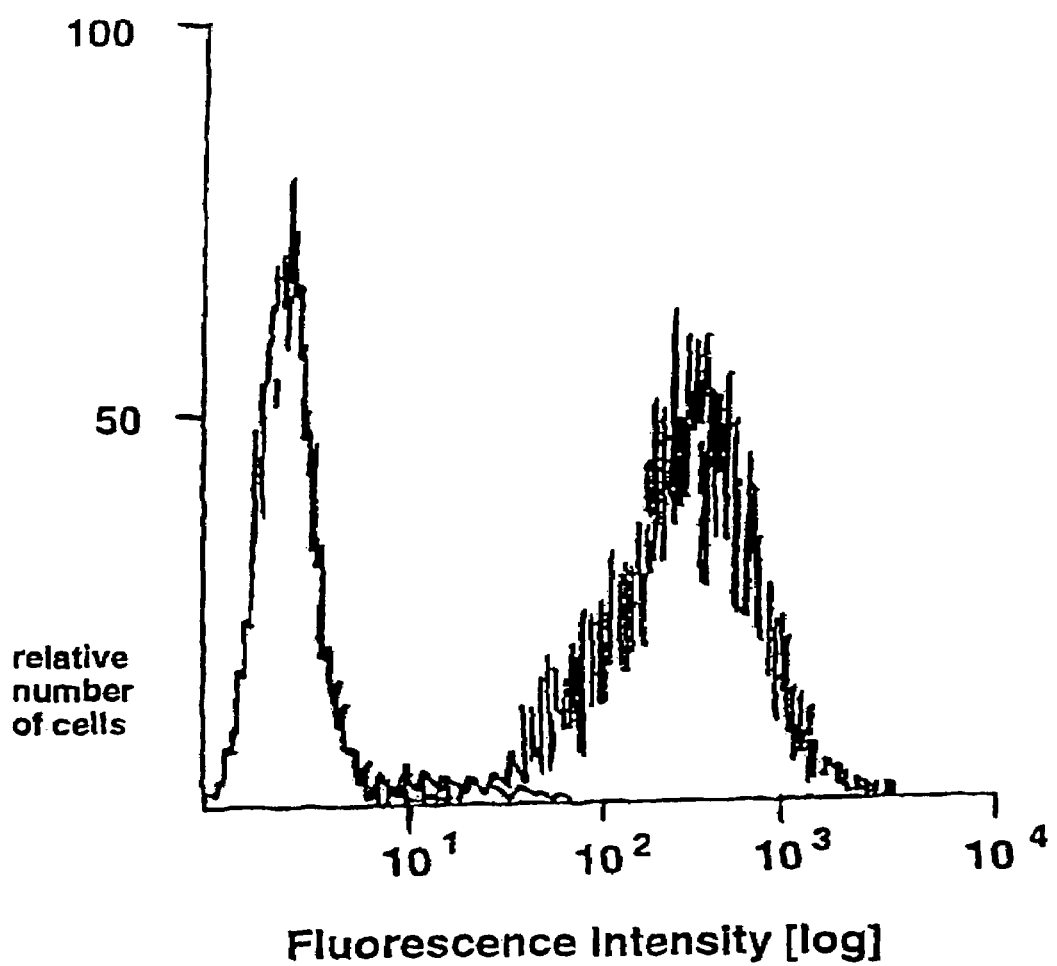
FIG. 7 is a graph from a FACS analysis of the binding of monkey Ab3 to tumor cells. Panel A shows the staining observed of GD2-expressing M21P6 cells-labeled with preimmune and immune Ab3. Panel B shows the staining observed on another cell line not expressing Gd2. Panel C shows control staining of M21/P6 cells using the GD2-specific antibody 14G2a, or no antibody.
Figure 7B:
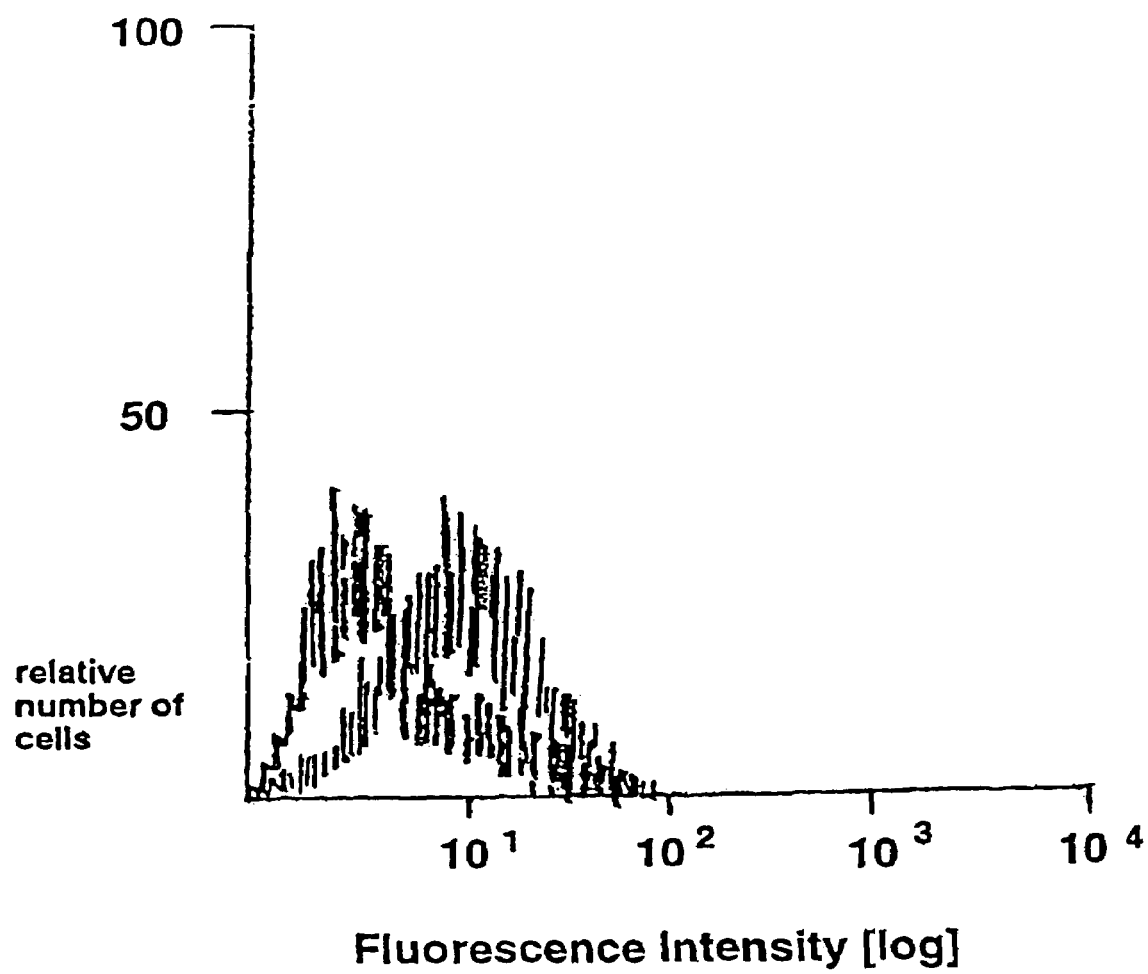
Figure 7C:
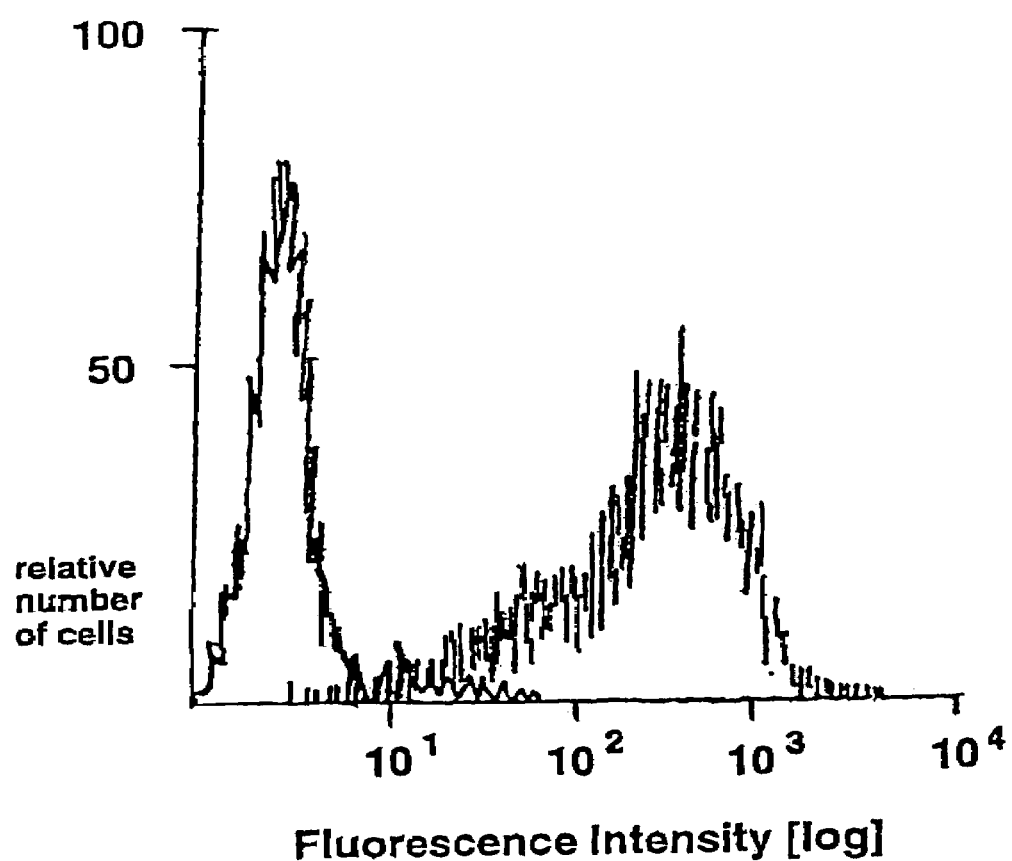

Results are shown in FIG. 7. In Panel A, tumor cells (M21/P6) were reacted with preimmune sera and Ab3 sera (1:100 dilution) from monkeys immunized with 1A7 mixed with QS-21. The reaction was developed with goat anti-human F(ab')$_2$ IgG-FITC-labeled antibody. In Panel B, MOLT-4 cells that do not express-GD2 were reacted with preimmune and immune monkey Ab3 sera raised against 1A7 plus QS-21. In Panel C, tumor cells (M21/P6) were reacted with PBS-BSA control and purified Ab1 (14G2a). The reaction was developed with goat-anti-mouse-F(ab')$_2$ IgG-FITC-labeled antibody. The results show that Ab3 from immune but not preimmune sera was specific for GD2-bearing M21/P6 cells.

Figure 8:
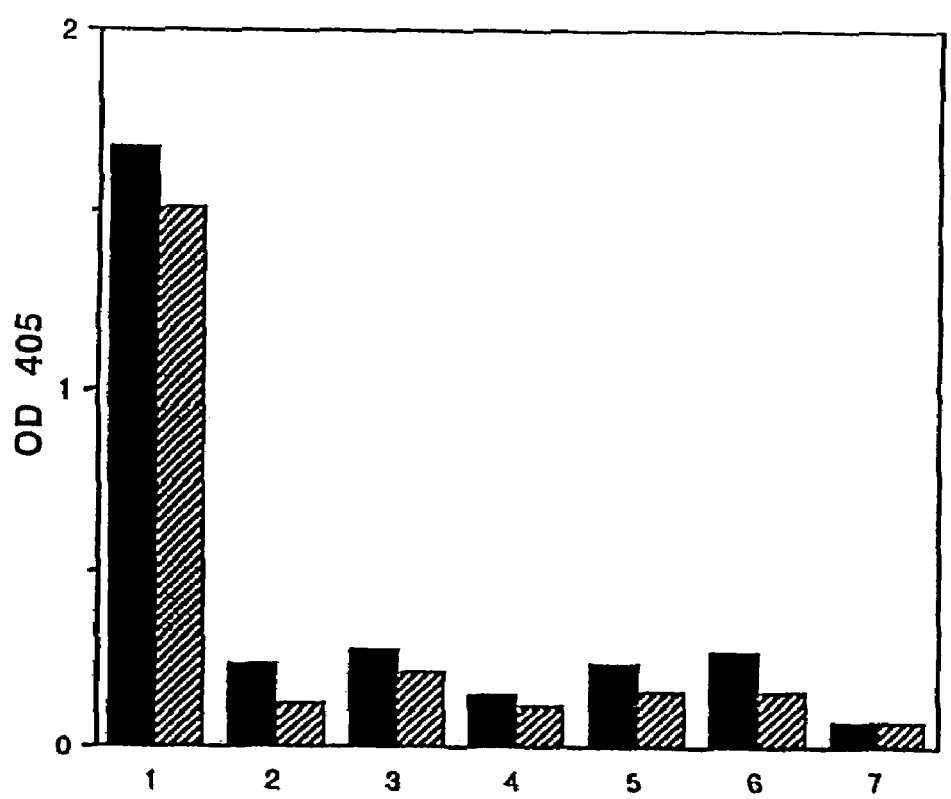
FIG. 8 is a bar graph depicting binding of Ab1 and monkey Ab3 to different gangliosides by ELISA. For each pair of bars, the left hand (solid) bar denotes the binding of Ab3 from monkey PRO#685; the right hand (hatched) bar denotes control binding by anti-GD2 antibody 14G2a. This experiment shows the antibody induced upon immunization with the anti-idiotype 1A7 is antigen specific.

FIG. 8 shows results from an experiment in which Ab3 was shown to bind directly to the GD2 target antigen in a specific fashion. 250 ng of different gangliosides were coated into 96-well plate. After blocking, 50 µg of different concentrations of PRO#685 (Ab3) and 14G2a (Ab1) was added and incubated 4 h at room temp. Bound antibody was detected using alkaline phosphatase conjugated second antibody.

Figure 9:
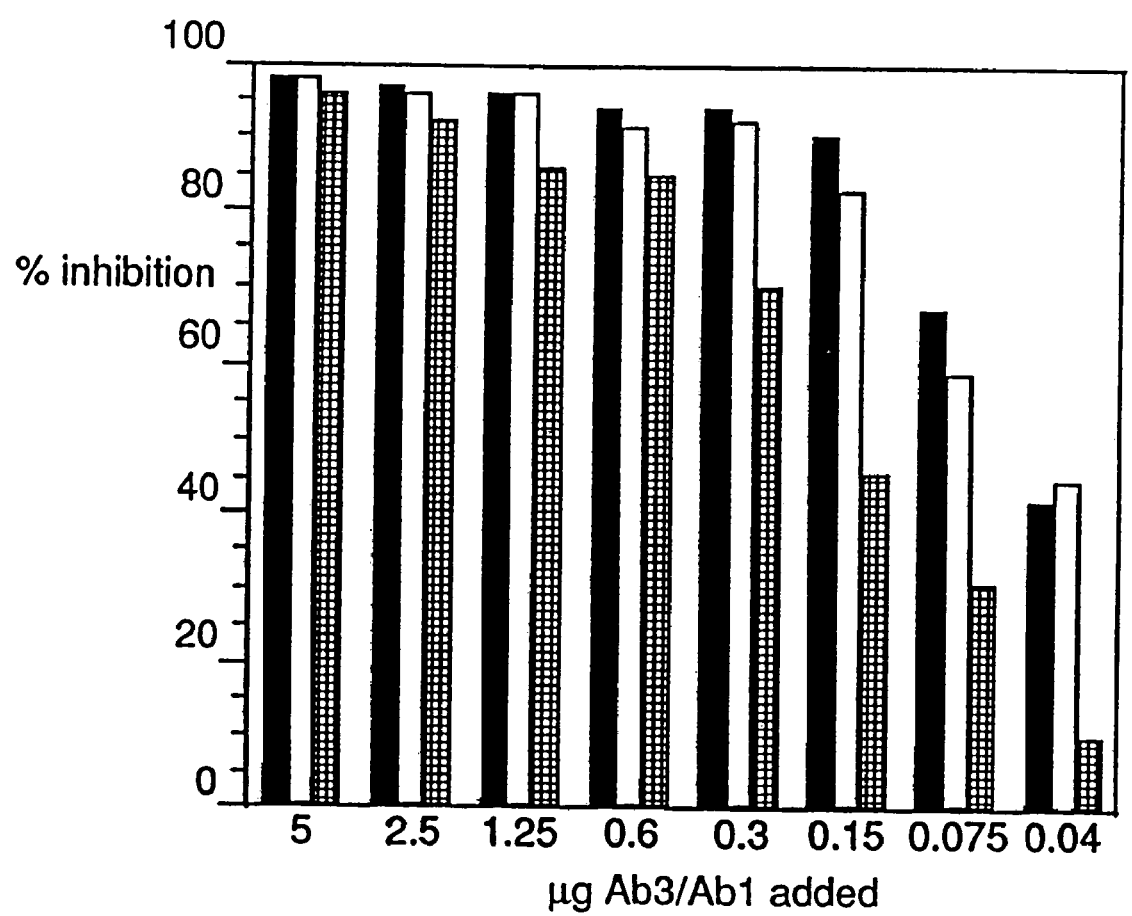
FIG. 9 is a bar graph depicting inhibition of binding of $^{125}$I-labeled 14G2a antibody to purified GD2 by 14G2a and monkey Ab3. For each triad of bars, the left hand (solid) bar denotes monkey PRO#778; the middle (open) bar denotes 14G2a, the right hand (hatched) bar denotes monkey PRO#685.

FIG. 9 shows the corresponding inhibition experiment Different gangliosides (250 ng) were coated into 96-well plate as before. Different concentrations of Ab3 and Ab1 along with 90,000 cpm of $^{125}$I-14G2a were added. The plate was incubated 2 h at room temperature with shaking, washed and counted. Percent inhibition was calculated and plotted against concentration of Ab1 and Ab3.

Figure 10:
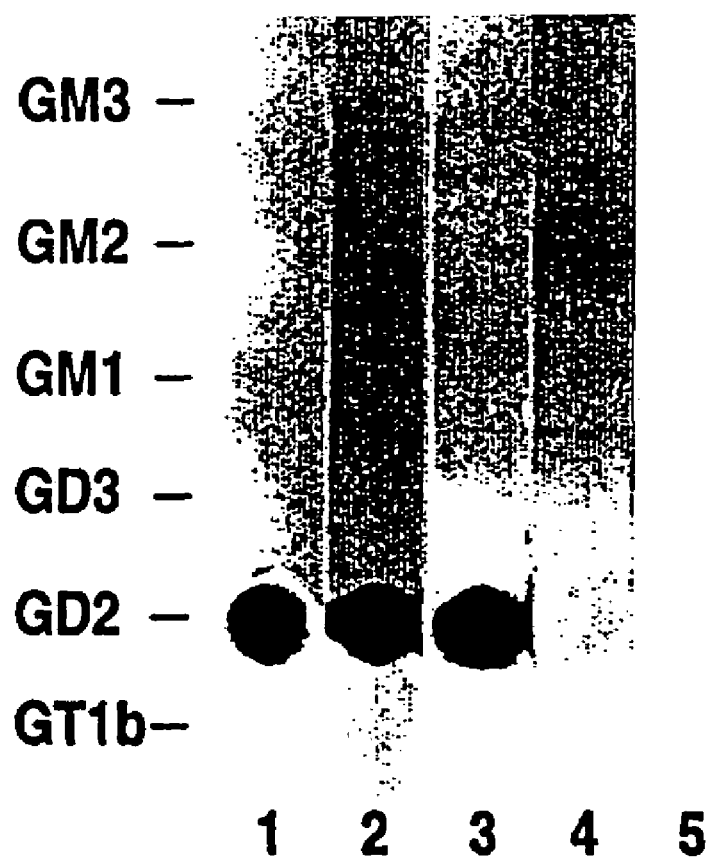
FIG. 10 is a half-tone reproduction of a blot analysis showing binding of 14G2a and monkey Ab3 to different gangliosides. Lane 1, monkey PRO#685; lane 2, monkey PRO#778; lane 3, 14G2a; lane 4, monkey anti-IID10; lane 5, PBS-BSA.

Reactivity of immunized sera and purified Ab3 for anti-GD2 antibodies against various gangliosides was also measured by immunoblotting (FIG. 10). Purified gangliosides (2 µg each of GM3, GM2, GM1, GD3, GD2 and GT1b) were spotted on strips of PVDF cellulose membrane at 1 cm intervals. After blocking with 3% BSA in PBS, the strips were incubated with PRO#685 (Ab3) or PRO#778 (Ab3) or 14G2a (Ab1) or an unrelated monkey Ab3 which was raised against an unrelated Ab2, 11D10 and PBS control; each antibody was used at 10 µg/ml, 5 ml of total solution. The incubation was done for 4 h at room temperature with shaking. After washing the strips were incubated with alkaline-phosphatase labeled second antibody (1:1000 dilutions) for 2 h at room temperature.

The results clearly demonstrate that 1A7-QS21 immunized monkey Ab3 antibody binds to the same antigen GD2 as Ab1.

The ability of the induced Ab3 to mediate antibody-dependent cellular cytotoxicity was confirmed in a standard ADCC assay. M21/P6 cells were labeled with $^{51}$Cr, and incubated in microtiter plate wells with dilutions of immune monkey sera. Normal human PBMC isolated by FICOLL/HYPAQUE® were then added as effector cells at an effector:target ratio of 50:1. The plates were centrifuged at 400×g for 2 min, and incubated for 4 h at 37° C. in a humidified atmosphere containing 5% CO$_2$. After incubation, the plates were centrifuged at 400×g for 5 min, and specific lysis was calculated from the cpm released into the supernatant The sera of two immunized monkeys (PRO 778 and PRO 685) each mediated specific lysis of −40-50% of target cells at a dilution of 1:10. In contrast, preimmune serum or the serum from a monkey immunized with an unrelated antiidiotype mediated specific lysis of only 4-8% of the labeled target cells.

The presence of a cellular immune response in the immunized monkeys was demonstrated in an in vitro proliferation assay. Mononuclear cells were isolated from the peripheral blood of immunized monkeys by FICOLL/HYPAQUE® gradient centrifugation. 5×10$^5$ cells per well were incubated with different concentrations of stimulant for 5 d at 37° C., and then-pulsed with 1 µCi/well [$^3$H]-thymidine for 20 h. Stimulation index was calculated by dividing the sample cpm by the average cpm obtained in medium control wells. The SD was <10% for each determination, done in triplicate.

Figure 11:
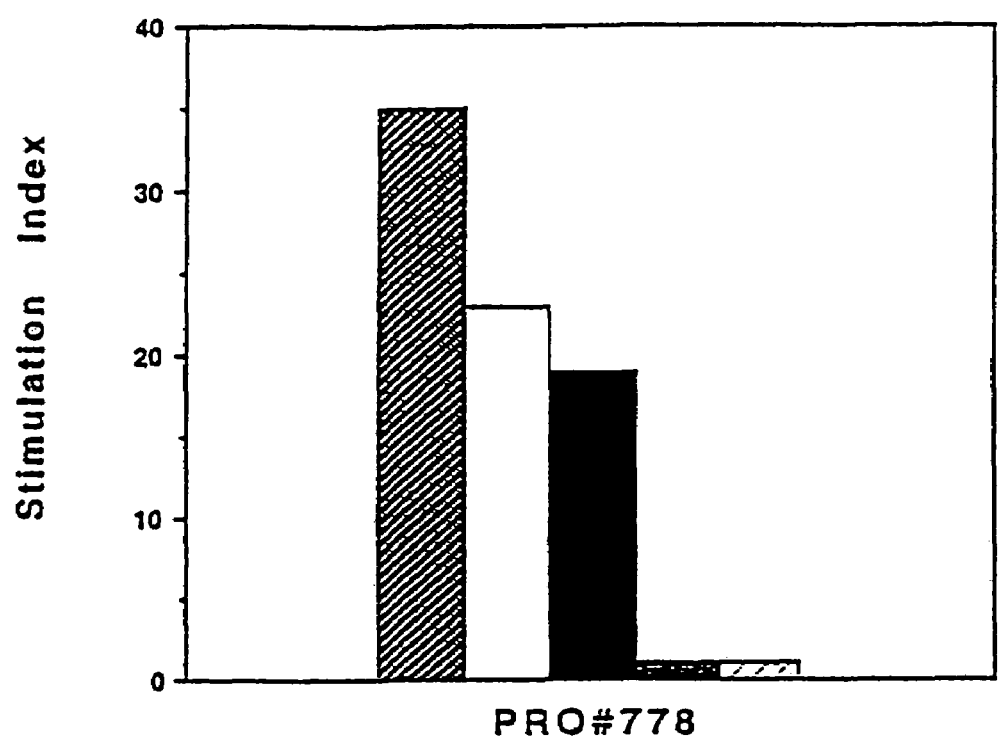
FIG. 11 is a bar graph depicting the proliferation of T cells obtained from monkeys immunized with monoclonal antibody 1A7, when they are stimulated in culture using either antibody 1A7 or a cancer cell line expressing GD2.
Figure 14:
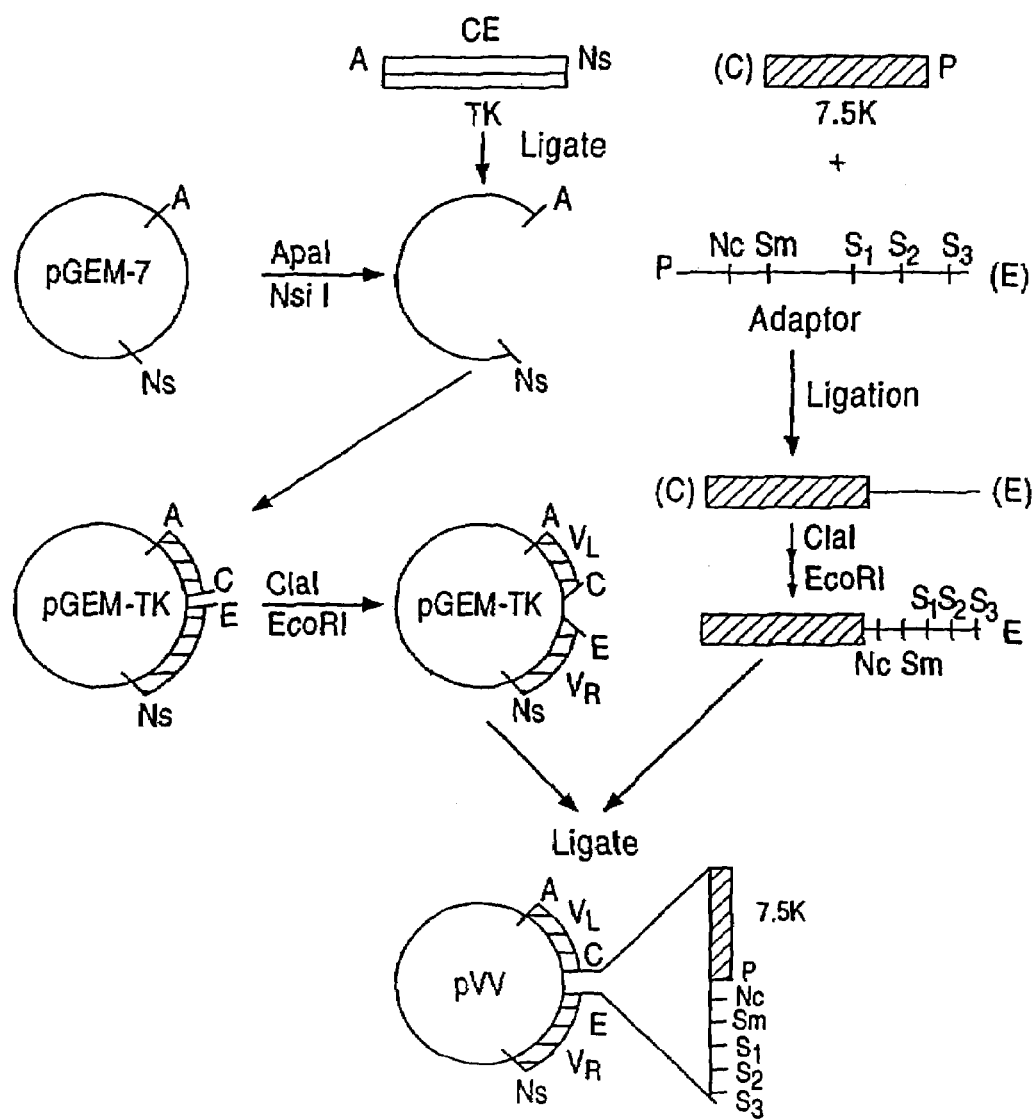
FIG. 14 is a map of a model plasmid construct for creating a vaccinia vector comprising a region encoding a 1A7 heavy or light chain variable region.

Results of the proliferation assay are shown in FIG. 11. Legend: Close hatching, 2 µg antibody 1A7; Open bars, 2 µg of an unrelated murine antiidiotype; Filled bars, radiation-killed M21/P6 cells (a GD2-expressing cancer line); Shaded bars, radiation-killed LS174-T cells (a GD2-negative cancer line); Light hatching, medium control. The reactivity indicated by the open bars likely represents a cellular response to non-idiotypic antibody components (i.e., an anti-murine immunoglobulin reaction). The additional reactivity observed when stimulated with 1A7 is consistent with a cellular response to the idiotypic components of 1A7. The ability of a GD2-expressing cell line but not a GD2-negative cell line to induce proliferation suggests that the cellular response comprises anti-GD2 activity.

The induction of Ab3 responses in monkeys did not cause any apparent side effects in animals despite the presence of GD2 in some normal tissues. Only mild local swelling and irritation were observed at the injection site as a result of multiple immunizations. The monkeys were routinely checked by physical examinations and weight measurements. They did not show any signs of abnormalities or neurological problems. Immunohistochemistry analysis of autopsy specimens obtained after 7 months indicated that there was no toxicity induced by the anti-Id 1A7 plus QS-21 vaccine treatment.

Example 4

Clinical use of 1A7 Antibody Vaccines in Patients with High Tumor Burden 9.7 g of purified 1A7 antibody have been prepared for clinical use. The antibody was purified by TSD BioServices under GMP-conditions. The regulatory testings on the antibody preparation have been completed according to FDA guidelines. Approval from the FDA has been obtained (BB-IND #6183) for use of 1A7 plus QS-21 in advanced melanoma patients.

The objectives of this study are to determine the effects of a first generation vaccine on various components of the immune response (both humoral and cellular), to determine the optimum immunomodulatory dose and toxicity of anti-Id antibody, and to determine whether there is a the benefit to clinical condition.

Eligible patients are those having metastatic melanoma that is confirmed as bearing the GD2 antigen. Patients must have a life expectancy greater than six months, adequate nutrition, non-pregnant, Southwest Oncology Group performance score 0, off all previous anti-cancer therapy for at least four weeks, no prior mAb therapy, no ongoing use of nonsteroidal anti-inflammatory agents or cimetidine or other H$_2$ receptor antagonists, adequate blood count and the ability to sign an informed consent.

All patients in the study are immunized with either 1 mg, 2 mg, 4 mg or 8 mg of 1A7 mixed with 100 µg of QS-21 adjuvant. Patients are randomized to one of the four dose levels. The total number of patients is between about 12 and 32. Injections are given biweekly for four total doses, or until an immune response is observed. Therapy continues with monthly injections until tumor progression is found. Patients are monitored carefully for anaphylaxis, serum sickness, and other potential side effects.

Periodic blood samples are obtained to determine the effect on hematopoietic cells as well as renal and hepatic function. All patients entered into the study undergo leukapheresis prior to the first immunization (pre-therapy). In addition, blood samples are obtained prior to each injection of 1A7 to determine serum levels of Ab3 and Ab1' antibodies and cytotoxic T cell responses. The specificity of the humoral responses is confirmed by immune flow cytometry, radioimmunoassay, and dot blot analysis. Antiglobulin responses to the murine antibody is tested by sandwich RIA. Sera are also be tested for the ability to inhibit the binding of anti-GD2 mAb to GD2 antigen. The immune profile of patients is further assessed by testing the proliferative response of patient's lymphocytes to anti-id antibody, purified GD2 antigen, and irradiated tumor cells and the cytotoxicity of patient's lymphocytes for GD2-positive HLA-matched cell lines or autologous tumor cells (where possible).

The development of humoral immunity induced by immunization with Ab2 is assessed by testing sera obtained from patients at different time points (pre-therapy, after 3 and 4 immunizations, and then periodically before injection if therapy continues). The sera is initially tested for total human anti-murine antibody (HAMA) response (anti-isotype and anti-allotype) by sandwich RIA. Briefly, microtiter plates are coated with 1A7 and incubated with different dilutions of patients' sera After washings, the antigen-antibody reaction is developed using $^{125}$I-labeled 1A7 in a homogeneous sandwich RIA. Since 1A7 is injected as intact IgG in this study, patients are expected to mount HAMA responses.

Sera from immunized patients with positive responses are then tested for the presence of anti-anti-idiotypic antibodies (Ab3). Sera are diluted with buffer coating normal murine immunoglobulin to block human antibodies against isotypic and allotypic determinants, and then checked for the presence of anti-1A7 by RIA Unrelated Ab2 is used as a control. After washing, the antigen-antibody reaction is developed using $^{125}$I-labeled anti-id reagent in a homogeneous sandwich RIA as above. Pre-treatment non-immune sera and sera from normal donors is used as control in these assays.

If antibody is detected against 1A7, the sera are checked for its ability to inhibit the binding of $^{125}$I-labeled 1A7 to 14G2a bound to microtiter plates, or inhibit the binding of radiolabeled 14G2a to 1A7 on the plate. An unrelated Ab1-Ab2 system is used as a control. This demonstrates whether Ab3 in patients' sera share idiotopes with 14G2a (Ab1). This inhibition assay of Ab1-Ab2 binding by Ab3 sera also demonstrates whether Ab3 is a true anti-anti-idiotype.

To assess humoral immune responses directed against native target antigens, patients' Ab3 sera is tested for reactivity with cell lines known to express GD2 in a RIA, and also by FACS analysis, using anti-human IgG and IgM tracer reagents. In addition, the sera is checked for reactivity against a solubilized purified preparation of GD2 antigen coated onto microtiter plates. The antigen-antibody reaction is detected by using $^{125}$I-labeled anti-human Ig reagents. Pre-immune sera is used as a control. Unrelated antigen is also used in the assay. Isotype of human Ab3 sera binding to GD2 antigen is determined by ELISA using anti-human isotype specific reagents.

To demonstrate that Ab3 and Ab1 bind to the same antigenic determinant, inhibition of 14G2a binding to an Ag positive tumor cell line or GD2 antigen by Ab3 sera is determined in an RIA. If Ab3 in patients' sera bind specifically to tumor cells, the ability of Ab3 to lyse these cell in conjunction with ADCC effector cells or complement can be demonstrated in standard ADCC or complement-mediated cytolysis (CMC) assays.

Quantitation of the Response:

Host Ab3 (anti-1A7 antibody) and Ab1' (anti-tumor antibody) reactivity are a key measurement in this example. The expression of anti-antiidiotyoe antibody (Ab3) in the patients' sem is quantitated by RIA inhibition studies as follows. Briefly, microtiter plates are coated with 14G2a (Ab1) and reacted with a fixed amount of $^{125}$I-labeled Ab2. A standard inhibition curve is generated using purified 14G2a as inhibitors. Next, patients' sera depleted of anti-iso-allotypic activity at different dilutions are checked for an ability to inhibit the Ab1-Ab2 reaction, and the amount of Ab1-like antibody in the sera is estimated from the standard inhibition curve. The induction and duration of Ab3 response are compared among different dose levels. If there is no statistical difference between Ab3 responses or duration at a number of doses, the titer of specific anti-tumor response (Ab1') in the sera by ELISA assay against purified GD2 antigen coated plates is compared among different dose levels.

If the serum of a particular patient tests positive for anti-1A7 (Ab3) but negative for anti-GD2 (Ab1'), it may be because the anti-GD2 is bound to the patent's tumor cells. The production of anti-GD2 is optionally demonstrated by stimulating the patients' PBMC in culture with 1A7 and then measuring anti-GD2 activity in the supernatant According to network hypothesis, patients immunized with 1A7 may eventually also induce an Ab4 response (anti-anti-antiidiotype) which may mimic the specificity of the anti-idiotype 1A7. To study this possibility, Ab3 positive patients' sera (depleted of anti-isotype and anti-allotype antibodies) are optionally measured for anti-idiotype activity by reacting with 14G2a (Ab1) by ELISA or RIA. Positive and negative controls are included as described for the Ab3 assay. Sera for this assay are obtained three months after the last therapy.

Cell-Mediated Immunity

Whether a specific T Cell response to the tumor associated glycolipid GD2 is generated in the 1A7 treated melanoma patients is tested by the following criteria: (1) if a T cell response is present which targets GD2 on the tumor cells, and (2) whether this response increases with repeated immunizations. Analysis proceeds in 2 phases. The first is to determine whether T cells from all PBMC samples received can be expanded following in vitro immunizations against the 1A7. If this occurs, the next step is to determine whether these T cells, can lyse or release cytokines against autologous GD2 bearing melanoma tumor cells or allogeneic GD2 expressing melanoma cells sharing a single HLA antigen in common with the autologous CTL.

Patients entered into the study are leukapheresed prior to the first immunization and FICOLL-HYPAQUE® separated peripheral blood mononuclear cells (PBMC) are prepared and cryopreserved for future studies. These PBMC (1) provide antigen presenting feeder cells for subsequent studies (2) serve as baseline for T cell responses and (3) are used to generate an autologous EBV cell line which is a transfection target for immunological studies. In addition, following each immunization, 60 ml of peripheral blood is drawn, FICOLL-HYPAQUE® separated and cryopreserved for the determination of T cell responses. The T cell responses to be studied are generation of specific cytotoxic T cells, cytokine producing T cells, and proliferation of the T cell cultures in response to the antigens. When available, cutaneous tumor biopsies are obtained from the patients to provide a source of tumor infiltrating lymphocytes (TIL). Similar studies are run using TIL to determine if tumor biopsies become a source of GD2 specific cells. Also, tumor biopsies provide a source of tumor cells to serve as critical autologous targets for cytotoxicity assays, cytokine production, and proliferation assays.

In-Vitro Functional activity of T cells is measured as follows: FICOLL HYPAQUE® separated PBMC ($1-3 \times 10^6$) are incubated in the presence of medium alone, IL-2 (10 Cetus units/ml), or 0.1 to 100 μg/ml anti-id 1A7 antibody. The cell culture medium includes Iscoves medium supplemented with 10% human AB serum, gentamycin, sodium pyruvate, nonessential amino acids, L-glutamine and 10 Cetus units/ml recombinant IL-2. Every 7 days the cultures are stimulated with irradiated autologous PBL pre-senzitized with the appropriate antigen used at day 0. The method of in vitro sensitization is similar to that recently described by Rivolitini et al., (1995) J. Immunol. 154:2257-2265. Beginning day 21 and on a weekly basis, proliferating cells are assessed for cell surface phenotype and cytotoxic and cytokine producing potential. Initially, all T cells are tested for their ability to recognize and lyse from autologous and allogeneic EBV cells transfected with the cDNA containing the sequence for the 1A7 anti-id molecule. Cultures lysing 1A7 transfected autologous EBV cells>10% are further tested against the NK sensitive line K562, the LAK sensitive line Daudi, autologous tumor if available and other HLA matched and mismatched GD2 bearing melanoma tumor cells. Preferably, a panel of over 40 well characterized melanoma tumor cell lines each expressing both class I and class II antigens is used. In addition, GM-CSF assays are run to determine if there is specific release of cytokines in addition to or in place of specific cytotoxicity. Proliferation of the cultures to the agents is determined by increases in cell numbers following in vitro stimulations.

The possible outcome of these studies following up to 6 rounds of in vitro stimulation is a kinetic increase in T cell cytotoxicity against both 1A7 transfected EBV cells, and autologous tumor and/or HLA matched allogeneic melanoma tumor cell lines. This indicates a successful immunization of the patients against their own tumor cells using the anti-id 1A7 molecule. Studies are then done to determine if the antigen recognized is GD2 on the tumor cells and identify the possible mechanisms of recognition.

Objectives of this study include: (1) determination of an optimal dose to elicit an immune response against GD2 in the various arms of the immune system; a T cell response being particularly desirable; (2) ideally, remission or palliation of the cancer.

Results

Five patients have been participating in the study over a sufficient period to provide confirmation of an immunological response. Each patient was immunized with 1 mg, 2 mg, 4 mg, or 8 mg of antibody 1A7 in QS-21 on a biweekly schedule. The first 2-4 doses were given intramuscularly, and periodic serum samples were collected to determine the presence of human anti-mouse (HAMA) activity and anti-1A7 activity. Titers were low, and it was decided to continue the course of immunization subcutaneously. All patients seroconverted positive with respect to both HAMA and anti-1A7, as determined by immunoassay. The response comprised specific Ab3 activity, as demonstrated by the ability of each serum to inhibit the binding of radiolabeled 1A7 to solid-phase linked 14G2a (Ab1).

To investigate the nature of the response further, anti-1A7 antibody was affinity purified from the sera of 4 of the patents. First, each sample was passed over a column of 14G2a antibody, eluted with a glycine buffer (pH~2.5), and exchanged into PBS. Next, HAMA activity that was not Ab3 was depleted by negative selection on a mouse immunoglobulin adsorbant. The amount of specific anti-1A7 (Ab3) obtained was as follows: Patient 1 (administered 1 mg 1A7 per dose), yield 0.67 mg Ab3 from 10 mL serum. Patient 2 (administered 2 mg 1A7 per dose), yield 1.32 mg Ab3 from 10 mL serum. Patient 3 (administered 4 mg 1A7 per dose), yield 1.71 mg Ab3 from 10 mL serum. Patient 4 (administered 4 mg 1A7 per dose), yield 0.73 mg Ab3 from 10 mL serum. This indicates that a substantial amount of Ab3 is produced as a result of administering 1A7 at any of the doses tested, and apparently is in molar excess of antigen in the circulation.

The affinity and specificity of the response to GD2 was further confirmed by using the affinity purified Ab3 in several of the assay systems described earlier. Results are shown in FIGS. 12 and 13.

FIG. 12 shows the results of ELISA conducted on Ab3 affinity purified from three different patients. In the upper panel an assay plate has been coated with ganglioside GD2 (batched bars) or GD3 (solid bars), overlaid with purified Ab3, and then developed with alkaline phosphatase labeled anti-immunoglobuli. The results show that each patient's response comprises the production of anti-GD2 antibody (Ab1'). In the lower panel, the plate was coated with GD2, overlaid with purified Ab3, and then developed with isotype-specific anti-immunoglobulin reagents. The anti-GD2 response is apparently a mature response comprising more IgG (hatched bars) than IgM (solid bars).

FIG. 13 shows the results of inhibition titration experiments conducted using purified Ab3 from three different patients. In the upper panel, an assay plate was coated with ganglioside GD2, and varying amounts of purified Ab3 were tested for the ability to inhibit the binding of radiolabeled 14G2a (Ab1). Diamonds: Patient 1; Squares: Patient 2; Triangles, Patient 3. The half-titration point was comparable to that of unlabeled 14G2a (Circles). In the lower panel, varying amounts of purified Ab3 were tested for their ability to inhibit the binding of radiolabeled 14G2a to the GD2-expressing murine lymphoma cell line EL4. The results indicate that the Ab3 induced by administration of 1A7 competes for binding to GD2 both in plate-binding assays and when presented on cancer cells.

Additional patients are enrolled in the study to characterize the immune response elicited by administration of antibody 1A7, and to follow any effect on the melanoma.

At the completion of the study, a second study is designed using the optimum immunomodulatory dose. The total number of patients in the second study is chosen for statistical reasons and is between about 16 to 25.

Example 5

Clinical use of 1A7-Antibody Vaccines in the Adjuvant Setting

The objectives of this study comprise ascertaining the effects of the 1A7 in patients who have been treated for a GD2-associated cancer and have no clinical manifestations of the disease. Ideally, 1A7 given at an optimal dose lessens the risk or rate of recurrence.

Eligible patients are those with GD2-positive small cell lung cancer. All of the patients must have entered a complete clinical remission following standard chemotherapy, and be within 6 weeks of completion of chemotherapy and radiation therapy. Patients must have a life expectancy greater than six months, adequate nutrition, non-pregnant, Southwest Oncology Group performance score 0, no history of monoclonal antibody therapy, no ongoing use of nonsteroidal anti-inflammatory agents or cymetidine or other $H_2$ receptor antagonists, adequate blood count, and the ability to sign an informed consent Various dose levels of 1A7 are combined with a suitable adjuvant. One candidate is QS-21. The QS-21 molecule consists of a triterpene glycoside with the general structure of a quillaic acid 3,28-O-bis glycoside. It consists of two structural isomers designated V-1 and V-2 at a typical ratio of about 2:1. Both isomers have adjuvant activity. QS-21 has been shown to promote a response to both T-dependent antigens and unconjugated T-independent antigens. QS-21 also augments the induction of Class I MHC-restricted cytotoxic T lymphocytes as well as antigen specific T-cell proliferation when used in subunit antigen vaccines. 100 µg QS-21 has been established as the optimal amount of adjuvant per dose in a trial conducted at the Memorial Sloan-Kettering Cancer Center, NY. The other candidate is RIBI™PC, which is obtained from Ribi Immunochem Research Inc., Hamilton Mont., and used according to manufacturer's directions.

Patients receive one intramuscular injection of 1A7 every two weeks for a total of four injections. Patients are immunized with either 1 mg, 2 mg, or 4 mg of 1A7 per injection mixed with 100 µg QS-21. Therapy continues on a monthly basis for 24 months, then every 3 months or until tumor progression is detected. The total number of patients is between 9 and 24.

Blood samples are obtained monthly prior to each treatment. Serum levels of Ab3 (anti-1A7), Ab1' (anti-Gd2) and human anti-mouse antibody (HAMA) are measured by standard immunoassay. The specificity of these responses is confirmed by indirect immunoprecipitation of radiolabeled cells and SDS-PAGE. Sera is also tested for the ability to inhibit the binding of labeled 1A7 to M21/P6 cells or purified GD2.

To determine if the vaccine is inducing T-cell immunity, the buffy coat of one unit of blood is centrifuged on FICOLL-HYPAQUE®. The peripheral blood mononuclear cells (PBMC) are removed, washed, and the lymphocyte precursor frequency is determined. Immunostaining for CD3, CD28, and CD45R markers is used to measure and sort cytotoxic T cells from suppressor T cells, using three-color flow cytometry. The proliferative response to 1A7 antibody and purified tumor antigen is determined. Cytotoxicity assays are conducted using HLA-matched colon cancer cell lines or autologous tumor cells. Suppressor cell function of CD8+ CD28+ CD45R+ cells is measured as the suppression of B cell immunoglobulin secretion.

The clinical features of each recipient are monitored regularly, and compared with the control population to determine the efficacy of treatment The dose and frequency of 1A7 treatment is adjusted if necessary as more patents enter the study. A dose of 1A7 is identified that significantly increases the risk or rate of progression compared with controls.

Example 6

Construction of a Recombinant Vaccinia Vector Encoding a 1A7 Polypeptide Fragment Recombinant vaccinia virus (rvv) can provide a powerful agent for overcoming immune tolerance. Vaccinia virus is highly immunogenic and stimulates both humoral and cell-mediated immune responses. Vaccinia is also capable of representing TAA along with the cellular MHC complex.

This example describes plasmid construction and production of recombinant vaccinia viruses. The scheme for construction of a general vaccinia vector (rvv) is shown in FIG. 14. The complete sequence of TK gene of the wild type WR strain of vaccinia virus (GenBank, accession number J02425,) was obtained from the National Center for Biotechnology Information (NCBI) by the BLAST program. Aitschul et al. (1990) *J. Mol. Biol.* 215:403-410. From the sequence data, forward and reverse PCR primers 5'-CAGATGGAAGGGCCCAAC (SEQ. ID NO:52) and 5'GATTGATGCATATCATTACC (SEQ. ID NO:53) were synthesized, corresponding to nucleotides 22-39 and 727-708 respectively of the TK sequence Hruby et al. (1983) Pro. Natl. Acad. Sci. USA 80:3411-3415. An Apa I site (underlined) was introduced into the forward primer and a Nsi I site (underlined) in the reverse primer for insertion into the plasmid pGEM-7Zf(+) (Promega). DNA from the wild type WR strain of vaccinia was isolated and TK gene was amplified by PCR. A DNA fragment of expected size (about 700 bp) was obtained by PCR. This DNA was separated by electrophoresis in low melting point agarose and purified by digestion with GELase (Epicentre Tech.). The TK DNA fragment was ligated to the pGEM-7Zf (+) after digestion with Apa I plus Nsi I. The resulting plasmid (pGEM-TK) was amplified by standard transformation techniques. Insertion was verified by restriction mapping.

Promoter 7.5 K was amplified from wild type vaccinia virus by PCR using the forward primer 5'-GTTATCGATGTCGAATAGCC (SEQ. ID NO:54) and the reverse primer 5-TTGCTGCAGATTGAGTACTGTTCT (SEQ. ID NO:55), corresponding to nucleotides-69-88 and 335-312 of the 7.5 K promoter sequence. Cochran et al. (1985) J. Virol. 54:30-37. A Cla I site (forward) and a Pst I site (reverse) were included in the primers. The amplified DNA fragment was digested with Pst I. A polynucleotide adaptor was synthesized with the smaller oligonucleotide being phosphorylated at the 5'-end by polynucleotide kinase. The hemi-phosphorylated adaptor was ligated to Pst I digested PCR amplified 7.5 K promoter DNA fragment The product was digested with Cla I/EcoR I digested pGEM-TK.

A cDNA insert encoding a 1A7 polypeptide is inserted between the Nco I and Xma I (Sma I) sites of pVV. This plasmid also contains the leader sequence of the $V_H$ at the 5' end of the scFv cDNA. If desired, a vaccinia control plasmid can be constructed containing cDNA for *E. Coli* β-galactosidase.

Construction of rvv: Rvvs are constructed by homologous recombination of vaccinia plasmids and wild-type WR strain of vaccinia virus according to the procedure of Mackett et al. (DNA Cloning, Vol. II, D. M. Glover, ed., IRL Press 1985) using CV-1 cells. Recombinant viral clones expressing β-galactosidase are selected by growth on $TK^-$ 143B cells in the presence of 5'-bromodeoxyuridine and 5-bromo-4-chloro-3-indoyl-β-D-galactosidase (X-Gal). Blue recombinant viruses are picked by Pasteur pipettes and plaque purified. As a second step in clone selection, Southern blot of extracted DNA is performed, using 1A7 cDNA as the probe. Further selection of rvv is made by assay of culture supernatant of the virally infected CV-1 or any other eukaryotic cells by ELISA. If cell-associated 1A7 polypeptide is in the rvv (i.e., if the leader sequence is deleted), cell lysate is assayed. Western blotting with 14G2a as probe is also performed. Biological activity of the 1A7 polypeptide synthesized by the vaccinia virus is determined by cell binding inhibition assay, as described above. Rvv clones containing 1A7 polynucleotides are selected by staining with 0.1% neutral red and plaque purified as above. Viral clones are grown into a high-titer lysate using standard techniques (Mackett et al (1982) Proc. Natl. Acad. Sci. USA 79:7415-7419). Typically a clone producing the highest amount of 1A7-polypeptide is selected for further studies.

Assay of 1A7 Polypeptides (Foreign Proteins) Expressed By Recombinant Vaccinia Virus: CV-1 cells are propagated in Dulbecco's modified Eagle's medium (DMEM) supplemented with 10% fetal calf serum and 100 units of penicillin and 100 µg of streptomycin per ml in 25-cm² flasks or Swell Cluster flasks. Cells are inoculated with rvv at a MOI of 30. The virus is allowed to absorb for 2 hours at 37° C. in a tissue culture incubator, following which the inoculum is replaced with the culture medium and the incubation was continued. Supernatant is removed after incubation for indicated time and the 1A7 polypeptide secreted is assayed. As a control, supernatant from mock infected cells is used. Assay of 1A7 polypeptides can be performed by testing for binding to 14G2a as described elsewhere in this disclosure. β-D-galactopyranoside produced by rvv-lacZ is assayed according to Miller (Experiments in Molecular Genetics, Cold Spring Harbor Pines 1972) with p-nitro-β-D-galactopyranoside as the substrate. Culture supernatant from virus infected cells is treated with β-propionate to inactivate the virus before assay (Corcoran et al. (1988) J. Parasit 74:763). Incorporation of ³H-thymidine by NFS60 cells is used as a measure of cell proliferation (Jaffee et al. (1993) Cancer Res. 53:2221-2226). Radioactivity due to ³H-thymidine incorporation in the presence of supernatant from mock infected CV-1 cells is subtracted as background. As positive control and for standard of biological activity, intact 1A7 is used. Alternatively, standard solutions of GM-CSF can be used as described in Qin and Chatterjee (1996) Gene Therapy.

Testing vaccinia 1A7 vaccines: For administration of vaccinia, a virus titer of $10^4$ to $10^7$ pfu is injected in a mouse. Injections can be subcutaneous, intramuscular, intradermal or interperitoneal. Immunizations are performed weekly. Mice are bled 7 days after every immunization for determination of Ab3 (including Ab1'). Testing for development of T cell immunity is performed 10 days after the booster immunization. Mice can also be tested by tumor challenge, in which survival after injection with tumor cells is monitored.

For administration of vaccinia via virally infected tumor cells, autologous tumor cells are maintained in Eagles medium containing 10% (vol/vol) fetal calf serum, 2 mM glutamine and gentamicin. A monolayer of confluent cells in a 75-cm2 flask is inoculated with ($3\times10^8$) plaque forming units (pfu) of rvv. After 2 hours at 37° C., the inoculum is replaced by DMEM and the incubation was continued for another 24 hours. After examination under microscope, cells are collected by scraping and washed two times with PBS and resuspended in PBS at a desired concentration. ($10^3$to $10^5$/200 μl). Female C57BL/6 mice, 6-8 weeks old are purchased from Harlan Bioproducts for Science Inc., (IN). Animals are injected subcutaneously with the cellular vaccine in the rear left flank and two weeks later tumor cells are injected at the rear right flank for challenge. Survival of mice following tumor challenge and the presence of tumor is monitored daily. If the tumor is measurable, tumors are measured weekly by a caliper in two dimensions and the volumes are calculated using the formula (width$^2$×length)/2. Tumors which are palpable but too small for measuring the volume accurately are recorded as zero volume, but tumor incidence is recorded as positive. Tumor volumes are averaged only for those that actually develop tumors over the observation period of 120 days. Zero values are included for those mice that eventually develop tumors but were tumor-free at a given time point.

Statistical evaluation is done using SigmaStat software (Jandel, Inc. San Rafael, Calif., USA). A P value of <0.05 is considered to indicate statistical significance.

Example 7

Expression and Characterization of a 1A7 Single Chain Variable Region Molecule Based on the sequence data listed elsewhere in this application, a cDNA construct is prepared by standard recombinant cloning techniques for single chain 1A7 derivatives in which $V_H$ and $V_L$ are joined through a linker sequence.

The strategy is as follows. The construct is incorporated into the pET-22b(+) plasmid vector (Novagen, Madison, Wis.) and expressed in *E. coli*. Sequence analysis is performed to confirm the plasmid construct, which contains the carboxy end of $V_H$ linked to the framework of $V_L$ and not the leader region. pET-22b(+) contains a nickel ion binding domain consisting of 6 sequential histidine residues ($His_6$). The $His_6$ domain has a high affinity for nickel, which is used for the purification of the recombinant 1A7 scFv.

A cell binding competition assay is performed to investigate whether the 1A7 scFv retains the antigen mimicry shown by intact 1A7. GD2-positive M21/P6 cells ($1\times10^5$ cells/well in 50 μl volume) are placed in a 96-well plate. The cells are incubated for 2 hours at room temperature with [$^{125}$I] 14G2a (Ab1), 100,000 cpm, in the absence and presence of increasing concentrations of 1A7 or the 1A7 scFv fragment Percent inhibition is calculated according to standard formulae.

The strategy has been implemented to prepare genetic constructs encoding scFv of the form $V_H$-$(GGGGS)_3$-$V_L$ and $V_L$-$(GGGGS)_3$-$V_H$. T-vector derived plasmids containing the encoding sequence for the 1A7 heavy chain variable region (pT1A7VH) and for the 1A7 light chain variable region (pT1A7VL) were obtained as described in Example 2. The plasmids were linearized by digestion with AvaI. Using the linearized plasmids as template, PCR amplification was conducted using a special set of primers designed to incorporate the following features:

1. A unique restriction nuclease site for subsequent ligation of the construct into a vector plasmid. An EcoRV site was used.
2. A Kozak's consensus sequence for ribosome binding operably linked at the 5' end to a start codon and the encoding region for the signal peptide of the first variable region;
3. A $(GGGGS)_n$ encoding sequence linked directly at the 3' end of the coding sequence of the first variable region (Framework 4);
4. A $(GGGGS)_n$ encoding sequence linked directly at the 5' end of the coding sequence of the second variable region without the signal peptide (Framework 1);
5. A stop codon linked directly at the 3' end of the coding sequence of the second variable region (Framework 4).
6. A second unique restriction nuclease site. XbaI was used For the construct $V_H$-$(GGGGS)_3$-$V_L$, $V_H$ was the first variable region and $V_L$ was the second; whereas for $V_L$-$(GGGGS)_3$-$V_H$, $V_L$ was the first variable region and $V_H$ was the second.

Using these primers in the initial PCR incorporates the translation and linker sequences during amplification. A region of overlap is present through the linker, which then permits the heavy and light chain sequences to be amplified together in a second round of PCR using the outermost primers.

The primers were synthesized by standard techniques by the Macromolecular Structure Analysis Facility at the University of Kentucky. The sequences are shown in Table 7. The abbreviation Lk stands for the linker (GGGGS)$_3$ (SEQ. ID NO:45).

TABLE 7

PCR primers used for constructing plasmid for 1A7 scFv expression

| Designation | Construct | Used to amplify | Orientation | Sequence (5'→3') |
|---|---|---|---|---|
| P1-VH SEQ. ID NO: 56 | V$_H$-(Lk)-V$_L$ | V$_H$ | forward | GCCGATATCACCAT GGCTGTCTTGGGGC TGCTC |
| P3-VLL SEQ. ID NO: 57 | | V$_H$ | reverse | TTGGGTCATCAAAA CATCGGATCCGCCG CCACCCGAGCCGCC ACCGCCCGAGCCAC CTCCCCCTGAGGAG ACGGTGACTGA |
| P2-VHL SEQ. ID NO: 58 | | V$_L$ | forward | TCAGTCACCGTCTC CTCAGGGGGAGGTG GCTCGGGCGGTGGC GGCTCGGGTGGCGG CGGATCCGATGTTT TGATGACCCAA |
| 3'-VL SEQ. ID NO: 59 | | V$_L$ | reverse | CATCTCTAGATTAT TTGATTTCCAGCTT GGTGCC |
| 5'-VL SEQ. ID NO: 60 | V$_L$-(Lk)-V$_H$ | V$_L$ | forward | GCCGATATCACCAT GGAGTTGCCTGTTA GGCTG |
| VLL3 SEQ. ID NO: 61 | | V$_L$ | reverse | TGACTGCTTCACCT GCACCTGGGATCCG CCGCCACCCGAGCC GCCACCGCCCGAGC CACCTCCCCCTTTG ATTTCCCAGCTTGG TGCC |
| 5'-VLLVH SEQ. ID NO: 62 | | V$_H$ | forward | GGCACCAAGCTGGA AATCAAAGGGGGAG GTGGCTCGGGCGGT GGCGGCTCGGGTGG CGGCGGATCCCAGG TGCAGGTGAAGGAG TCA |
| 3'-VH SEQ. ID NO: 63 | | V$_H$ | reverse | CATCTCTAGATTAT GAGGAGACGGTGAC TGAGGT |

The V$_H$-(Lk)-V$_L$ construct was assembled in the following way: A PCR amplification was conducted on the linearized pT1A7VH plasmid using P1-VH and P3-VLL, and on the linearized pT1A7VL plasmid using P2-VHL and 3'-VL. The amplified products were freed of primers, annealed, and another round of PCR amplification was done using the primers P1-VH and 3'-VL. The product was a DNA fragment comprising an encoding sequence for a single-chain molecule containing in order: the V$_H$ signal sequence, V$_H$, the linker, and V$_L$.

FIG. 15 lists the nucleotide sequence (SEQ. ID NO:65) for the V$_H$-(Lk)-V$_L$ obtained from the second round of PCR amplification. Restriction sites EcoRV and XbaI are shown by underlining. The ATG start codon is italicized and preceded by a |. The linker sequence is the long underlined section near the middle of the sequence. The termination codon TAA is italicized and followed by a |. The Kozak's consensus sequence ACCATGG (SEQ. ID NO:64) precedes the start codon Shown below the nucleotide sequence is the expected translation product (SEQ. ID NO:66) which is 263 amino acids in length The V$_L$-(Lk)-V$_H$ construct vas assembled in exactly the same fashion, except that the second set of primers listed in Table 7 were used in the PCR amplification reactions.

Each of the constructs was cloned into a pcDNA3-derived vector plasmid. pcDNA is a ~5445 base-pair circular DNA containing in order the CMV promoter, a polycloning site, and the bovine growth hormone polyadenylation signal (BGHpA), and was obtained from InVitrogen. The pcDNA3 plasmid was first modified to remove unneeded sequences to improve its suitability for administration to human subjects. First, it was digested with PvuII and self-ligated. This resulted in removal of 2165 base pairs comprising the neomycin resistance gene. The product was digested with NruI and PvuI, and blunted by digestion with 3'-5'-exonuclease. This removed the ampicillin resistance gene, resulting in a linear DNA designated pcDNA 3.2. Kanamucin resistance gene was cut out from pUC4K with PstI, and blunted by 3'-5'-exonuclease digestion to make a DNA fragment designated pUC4K1.2. pUC4K1.2 and pcDNA3.2 were then ligated, resulting in the formation of a "humanized" plasmid with a kanamucin resistance gene, designated pHcDNA3. The scFv encoding sequences were cloned into pHcDNA3 by digesting both the plasmid and the scFv DNA fragment with EcoRV and XbaI, followed by ligation.

Figure 16:
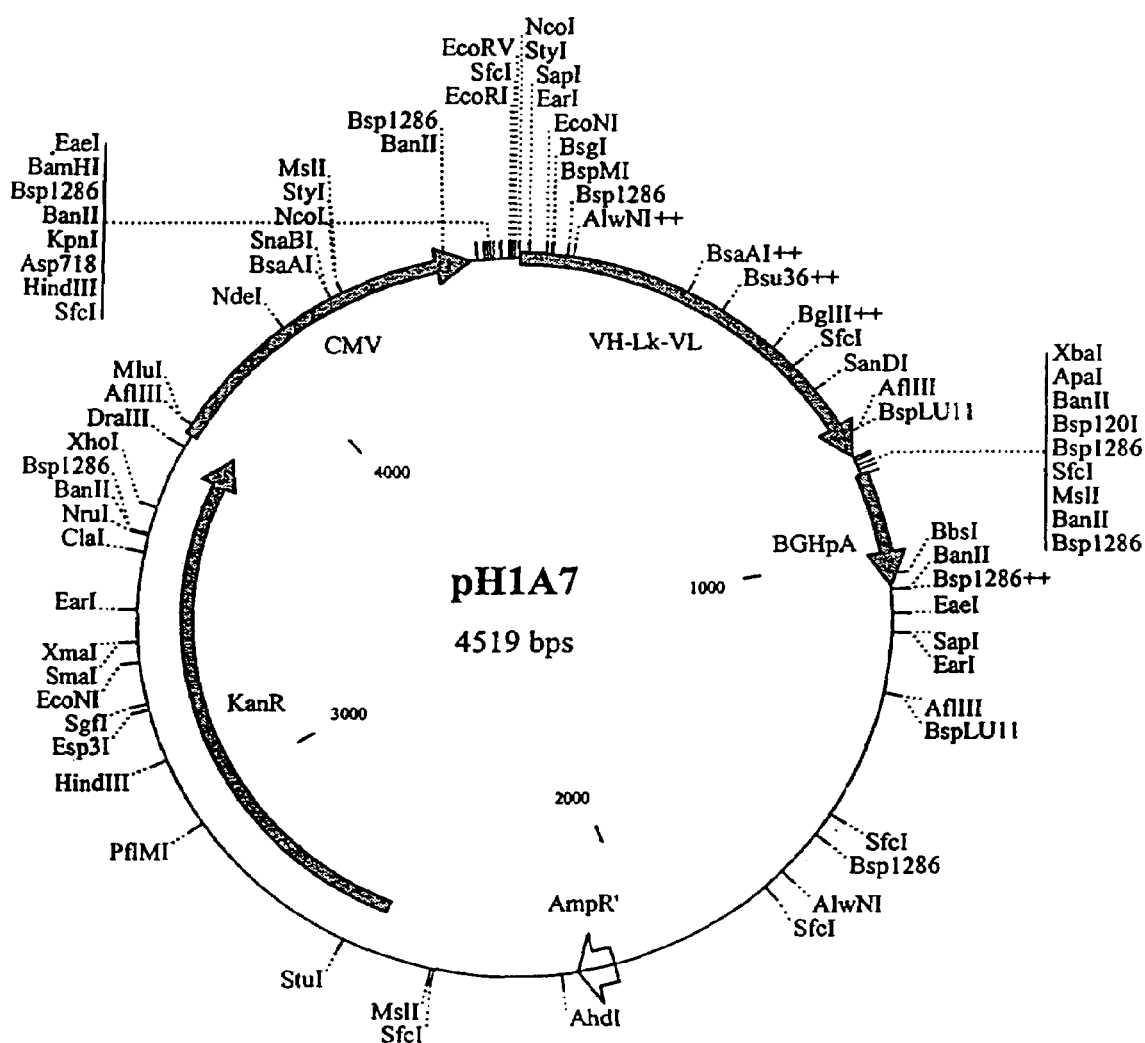
FIG. 16 is a map of a vector plasmid comprising an expression cassette for a scFv and adapted for administration as a human polynucleotide vaccine.

FIG. 16 is a map of the construct comprising an expressible gene for the V$_H$-(Lk)-V$_L$ scFv. The encoding region is under control of the CMV promoter, and linked downstream to the bGHpA polyadenylation sequence.

Ability of the plasmids to express the encoded protein in a suitable conformation is tested by transfecting CHO cells and MC38 cells. TRANSFECTAMINE™ or electroporation are alternatively used to effect the transfections. Both the culture supernatant and a cell lysate are tested for the presence of the gene product. A sandwich ELISA is conducted using antibody 14G2a (Ab1) as both plate coat and $^{125}$I-labeled developing reagent. A parallel assay using an irrelevant antibody as developing reagent is used as negative control. Positive results are confirmed by conducting a Western blot using $^{125}$I-14G2a. The expected size of the scFv gene product is ~44 kDa.

The scFv can be isolated by affinity chromatography using a 14G2a adsorbant, eluted with a pH ~2.5 glycine buffer. Further investigation of the specificity of the scFv is conducted using the affinity-purified protein. GD2-positive M21/P6 cells (1×10$^5$ cells/well in 50 µl volume) are placed in a 96-well plate. The cells are incubated for 2 hours at room temperature with $^{125}$I-14G2a (Ab1), 100,000 cpm, in the absence and presence of increasing concentrations of 1A7 or the 1A7 scFv fragment Percent inhibition is calculated according to standard formulae.

Plasmids encoding scFv with the correct specificity are assembled into candidate 1A7 vaccines using methods known in the art for assembling polynucleotide vaccines. One such candidate is a naked DNA vaccine. It is prepared by growing the plasmid to sufficient quantities, purifying it from the host cell, and mixing it with a pharmaceutically compatible buffer. Another candidate comprises cationic liposomes to facilitate transfection. Materials and methods for assembling cationic liposomes are known in the art: see U.S. Pat. Nos. 5,264,618; 5,334,761; and 5,459,127.

Candidate 1A7 polynucleotide vaccines are tested for immunogenicity as follows. Two groups of 10-15 female C57BL/6 mice (6-8 weeks old) are immunized intramuscularly with doses of 50-100 μg purified plasmid. Various routes of administration are compared, such as intramuscular, intradermal, subcutaneous and interperitoneal.

Mice are bled 7 days after each immunization for determination of anti-1A7 and anti-GD2 activity as described elsewhere in this disclosure. Three mice are sacrificed from each group for isolation of spleens for the T cell proliferation assay 10 days after a booster immunization. To determine whether effects are specific, the following negative controls are used: (a) plasmid without the 1A7-scFv polynucleotide insert; (b) plasmid with the scFv polynucleotide insert in the opposite orientation with respect to the promoter, and (c) plasmid containing a polynucleotide encoding an scFv of an unrelated anti-idiotype antibody.

Example 8

Development of an Animal Model for Testing Vaccines Comprising a 1A7 Polynucleotide or Polypeptide Derivative A number of different fragments, constructs, plasmids, and fusion proteins are contemplated in this invention as a second generation vaccine for GD2-associated tumors. Animals have been established in the examples given so far as suitable for testing whether a candidate vaccine can elicit an immune response. Ultimately, the objective is to use the vaccine in tumor therapy, and it is desirable to have an animal model that can be used to screen candidate vaccines for this end-point.

Accordingly, a (57BL/6) mouse EL4 lymphoma model was developed.

Cheung et al. (1993, Int. J. Cancer 54:499-505) reported that murine lymphoma EL4 cells express GD2 at high density. MAb 14G2a was tested for binding to EL4 cells. Essentially 100% of the EL4 cells (a gift from Dr. Suzanne Rosenberg, Univ. of Maryland) bound at high fluorescence intensity with 14G2a by FACS analysis. The cell binding inhibition curve showed that 1A7 can effectively inhibit the binding of 125-labeled 14G2a to EL4 cells. Immunization of C57BL/6 mice with anti-Id 1A7 plus QS-21 induced anti-GD2 antibodies which bind to EL4 cells and kill EL4 cells in in vitro ADCC-assay. Also, spleen cells from immunized C57BL/6 mice showed in vitro T cell proliferation in presence of irradiated EL4 cells. Thus, murine EL4 lymphoma in syngeneic immunocompetent C57BL/6 mice can serve as a suitable animal model for evaluating the efficacy of anti-Id A7-based vaccines.

100,000 EL4 cells are injected subcutaneously (s.c.) into C57BL/6 mice. This is lethal to the host, and the median survival time is approximately four weeks. Since median survival time is dependent on the inoculum of tumor cells, a dose-related time curve is generated using $10^3$, $10^4$, $10^5$, $10^6$, and $10^7$ tumor cells/mouse, injected s.c., with 10 mice per group. A dose is determined that develops into a slow growing or rapidly growing tumor. The subcutaneous tumor model permits us to more closely monitor tumor growth and host immune response without slicing the mouse. EL4 cells also can be injected i.p. which grow very rapidly with intra-abdominal metastasis. The intraperitoneal model can be adapted to study the immune response to tumors which develop systemically.

Five different forms of vaccines are explored and compared for efficacy. The vaccines are:

(i) 1A7-QS21 (as our standard control)
(ii) Irradiated EL4 cells (Positive Control)
(iii) GD2-KLH plus QS-21 (Antigen Vaccine)
(iv) 1A7-plasmid
(v) 1A7-Vaccinia Construct The serum levels of anti-anti-Id (Ab3) and anti-GD2 antibodies is measured as described elsewhere in this disclosure. Typically, blood samples are obtained before vaccination and ten days after each immunization and assayed for anti-GD2 antibodies. The time course is determined over which the immune response develops, the intensity of the immune response, the effect of multiple injections of vaccine (boosting), duration of the humoral response and variability of the humoral response between animals. Comparing the anti-GD2 titers with survival of tumor challenge establishes whether there is any correlation between the level of humoral response and tumor protection. The specificity of the immune response is examined by ELISA, RIA, Dot Blot analysis and FACS analysis. The serum Ab3 is also studied by in vitro ADCC or CMC assays. The target cells are EL4. The isotypes of anti-GD2 antibodies in the serum of mice are determined by ELISA using isotype specific reagents.

The cellular immune response is assayed using a T cell proliferation assay and a cytotoxic T lymphocyte (CTL) assay. The proliferation assay is used to assess the proliferative response of cells from vaccinated mice to various stimuli. Spleen cells are harvested from animals immunized with an experimental vaccine or control vaccine and placed into in vitro cultures. The splenocytes are then stimulated with either media alone, phytohemagglutinin (PHA), irradiated EMA cells, purified GD2, anti-Id 1A7 or an irrelevant Ab2. Cell proliferation is measured after 5 days of culture and then stimulation for 18 hours by [$^3$H]-thymidine incorporation. Stimulation of the spleen cells with PHA shows the maximum proliferation of T cells, and culturing with media alone measures base line proliferation. Splenocyte cultures are of mixed cell type, including antigen presenting cells. Pulsing cells with the above stimulants results in antigen processing by these cells and a reactive T lymphocyte proliferation. By comparing the proliferative response of the differently vaccinated mice, it is possible to determine if there is an advantage of any particular vaccine form over others.

In order to determine which subset of T-cells are being induced, the proliferating cells are phenotyped by flow cytometry. Alternatively, splenic T-cells are depleted of either CD4+ or CD8+ cells before proliferation assay by incubation with monoclonal antibody RL.172 (anti-CD4+) or mAb.168 (anti-CD8+) and complement.

One of the effector mechanism thought to be important for tumor protection is antigen specific CT killing. EL4 or GD2 specific CTL activity will be assayed to determine if the vaccines induce this type of cellular response. Splenocytes are harvested from vaccinated mice and co-cultured with irradiated EL4 tumor cells and IL-2 for five days to expand Ag specific CTL. The splenocytes are then mixed with $^{51}$Cr-labeled target cells at various effector to target ratios, and then assayed for released radioactivity. The target cells are EL4 cells and MC38 cells. MC38 is a murine-colonic tumor cell line which was derived from the same mouse strain and thus shares the same H-2 haplotype but has different surface antigen makers. Both of these tumor cells take up $^{51}$Cr and have a low spontaneous release. Vaccination of mice should stimulate the production of CTL which specifically lyse EL4 cells and not MC38 cells.

By comparing the CTL activity in differently vaccinated mice, the particular type of vaccine stimulates different levels of CTL response is determined. Also determined is whether different adjuvants or cytokines are needed to influence this type of immune response generated.

Example 9

Evaluating the Efficacy of Derivative Vaccines

Efficacy of the different vaccinations is measured by the degree of tumor protection caused by vaccines using the animal model outlined in the previous example. Tumor protection is compared with other measurements of the immune response to determine if there is any correlation between tumor protection and level of humoral or cellular response.

To evaluate the ability of vaccinations to prevent tumor growth, vaccinated mice are challenged with a lethal number of tumor cells. The immunization schedule is determined by evaluating the humoral and cellular immune response as described above. It is likely that the schedule and number of immunizations necessary to induce a significant immune responses varies between the different types of vaccines. Fifteen mice are used in each vaccination group including one group of mice immunized with an irrelevant Ab2. Blood samples are obtained after 7 days of each immunization to monitor the humoral response. Once immunized, 10 of the mice are challenged with a previously established lethal number of EL4 cells injected s.c. The survival of the different vaccination groups is compared using Kaplan-Meier analysis. The other five mice in each vaccination group are used for CTL assays. These studies give information about the immune status at the time of tumor challenge and protection from tumor growth. Different types of vaccines are also compared (anti-Id protein, cells, GD2-KLH or DNA) for their ability to stimulate a protective immune response.

The level of tumor protection is evaluated by the number of mice that survive a tumor challenge and the dose of tumor cells immunized mice can survive. The level of tumor protection is measured for each of the vaccines which stimulate tumor protecting immune responses.

Specificity of tumor protection is evaluated using an unrelated tumor cell such as MC38 which grows subcutaneously in C57BL/6 mice. Groups of mice are vaccinated with different vaccines and then challenged with either EMA or MC38 cells. The mice are observed daily and survival comparison between two groups of mice is made using Kaplan-Meier analysis.

To evaluate the effectiveness of vaccine therapy in the treatment of mice with established tumor, C57BL/6 mice are injected with appropriate number of EL4 cells subcutaneously and then 24 hours later immunized with different vaccines or unrelated Ab2 vaccine. The mice are reimmunized every week and followed for tumor growth and survival.

Experiments are conducted to determine the immune effector arm, involved in protective immunity against syngeneic GD2 antigen bearing tumors. Adoptive transfer of immune Ab3 serum (containing Ab1') or immune T-lymphocyte subsets (CD4+ or CD8+) or NK cells is done into naive recipient C57BL/6 mice previously treated with sublethal dose of radiation to allow for cell expansion. The recipient mice and previously vaccine immunized positive control mice are then injected with a lethal number of tumor cells and followed for tumor growth and survival.

Example 10

Clinical Use of Derivative Vaccines

Promising results using plasmids in the animal tumor model of the previous example lead to development of plasmid vectors for human use. The pcDNA3 vector is modified according to Conry et al. for incorporation of the appropriate Ab2β fragment. This modification involves deletion of the neomycin gene and replacing it with Tn903 kanamycin resistance gene. Ampicillin resistance gene and viral sequences corresponding to nucleotide 5004-208 are also deleted. The plasmid is prepared on a large scale under Good Manufacturing Practice (GMP) conditions. Purified plasmid is stored at −70° C. in aliquots of 5 mg/ml.

Vaccinia constructs are made in Wyeth-calf adapted stain of vaccinia. This strain of vaccinia has been used for smallpox vaccination and has been shown to be safe in cancer patients. Clones of rvv are picked and plaque purified. Rvv are grown under GMP conditions using certified strains of eukaryotic cells. Virus is concentrated by sucrose gradient centrifugation.

An initial study is done in six advanced melanoma patients. Depending on results, anti-Id based DNA vaccines is combined with the standard control 1A7 plus QS-21 vaccines for augmenting tumor specific immunity in vaccinated patients.

ADDITIONAL REFERENCES

Gangliosides as Tumor Antigens

Livingston, P. O. Approaches to augmenting the immunogenicity of melanoma gangliosides: From whole melanoma cells to ganglioside-KLH conjugate vaccines. Immunol. Review, 145:147-166, 1995.

Hamilton, W. B., et al. Ganglioside expression human malignant melanoma assessed by quantitative immune thin layer chromatography. Ing. J. Cancer, 53:566-573, 1993.

Hamilton, W. B., et al. Ganglioside expression on sarcoma and small cell lung carcinoma compared to tumors of neuroectodermal origin. Proc. Am. Assoc. Cancer Res. 34:491, 1993.

Tsuchida, T., et al. Gangliosides of human melanoma. J. Natl. Cancer Inst. 78:45-54, 1987.

Cheresh, D. A., et al. Biosynthesis and expression of the disialoganglioside GD2, a relevant target antigen on small cell lung carcinoma for monoclonal antibody-mediated cytolysis. Cancer Res. 46:5412-5118, 1996.

Mujoo, K, et al. Disialoganglioside GD2 on human neuroblastoma cells. Target antigen for monoclonal antibody-mediated cytolysis and suppression of tumor growth. Cancer Res. 47:1098-1104, 1987.

Cheung, N-K. V., et al. Ganglioside GD2 specific monoclonal antibody 3F8. a Phase I study in patients with neuroblastoma and malignant melanoma J. Clin. Oncol. 5:1430-1440, 1987.

Irie, R. F. and Morton, D. L. Regression of cutaneous metastatic melanoma by intralesional injection with human monoclonal antibody to ganglioside GD2. Proc. Natl. Acad. Sci. USA. 83:8694-8698, 1986.

Saleh, M. N., et al. Phase I of the murine monoclonal anti-GD2 antibody 14G2a in metastatic melanoma. Cancer Res. 52: 4342-4347, 1992.

Cheung, N-K Cheung, et al. Antibody response to murine anti-GD2 monoclonal antibodies: Correlation with patient survival. Cancer Res. 54:2228-2233, 1994.

Handgretinger, R., et al. A Phase I study of neuroblastoma with the anti-ganglioside GD2 antibody 14G2a. Cancer Immunol. Immunother. 35:199-204, 1992.

Cheresh, D. A., et al. Localization of the gangliosides GD2 and $G_{p3}$ in adhesion plaques and on the surface of human melanoma cells. Proc. Natl. Sci. USA, 81:5767-5771, 1984.

Cheresh, D. A., et al. Disialogangliosides $G_{D2}$ and $G_{p3}$ are involved in the attachment of human melanoma and neuroblastoma cells to extracellular matrix proteins. J. Cell Biol. 102:688-696, 1986.

Cheresh, D. A. et al. Disialoganglioside $G_{D2}$ distributes preferentially into substrate-associated microprocesses on human melanoma cells during their attachment to fibronectin. J. Cell Biol., 102:1887-1897, 1986.

Plasmid and Vaccinia Vaccines

Spooner, R. A., et al. DNA vaccination for cancer treatment. Gene Therapy, 2:173-180, 1995.

Wang, B., et al. Immunization by direct DNA inoculation induces rejection of tumor cell challenge. Human Gene Therapy, 6:407-418, 1995.

Conry, R. M., et al. A carcinoembryonic antigen polynucleotide vaccine for human clinical use. Gene Therapy, 2:33-38, 1995.

Hawkins, R. E., et al. A genetic approach to idiotypic vaccination. J. Immunother. 14:273-278, 1993.

Pisetsky, D. S. DNA vaccination: a clue to memory? Human Immunol., 38:241-242, 1993.

Jiao, S., et al. Direct gene transfer into nonhuman primate myofibers in vivo. Human Gene Ther. 3:21-33, 1992.

Nabel, G. J., et al. Direct gene transfer with DNA-liposome complexes in melanoma: expression, biological activity, and lack of toxicity in humans. Proc. Natl. Acad. Sci. USA. 90:11307-11311, 1992.

Kaufman, H., et al. A recombinant vaccinia virus expressing human carcinoembryonic antigen (GD2). Int. J. Cancer, 48:900-907, 1991.

Moss, B. and Flexner, C. Vaccinia virus expression vectors. Ann. Rev. Immunol., 5:305-324, 1987.

Moss, B., et al. Live recombinant vaccinia virus protects chimpanzees against hepatitis B. Nature, 311:67-69, 1984.

Wachsman, M., et al. Expression of herpes simplex virus glycoprotein D on antigen presenting cells infected with vaccinia recombinants and protective immunity. Biosci. Res. 8:323-334, 1988.

Anti-idiotypes as Inducers of Anti-Tumor Immune Response

Foon, K. A., et al. Active Immunity to the Carcinoembryonic Antigen in Patients Treated with an Anti-Idiotype Antibody Vaccine. J. Clin. Invest. 96:334-342, 1995.

Bhattacharya-Chatterjee, M., et al. Idiotype vaccines against human T cell acute lymphoblastic leukemia. I. Generation and characterization of biologically active monoclonal anti-idiotypes. J. Immunol. 139:1354-1360, 1987.

Bhattacharya-Chatterjee, M., et al. Idiotype vaccines against human T-cell leukemia J. Immunol. 141:1398-1403, 1988.

Bhattacharya-Chatterjee, M., et al. Murine monoclonal anti-idiotype antibody as a potential network antigen for human carcinoembryonic antigen. J. Immunol. 145:2758-2765, 1990.

Bhattacharya-Chatterjee, M., et al. Anti-idiotype antibodies as potential therapeutic agents for human breast cancer. In Antigen and Antibody Molecular Engineering in Breast Cancer Diagnosis and Treatment Conf. on Breast Cancer Therapy Immunology, R. L. Ceriani (Ed.), Plenum Press, N.Y., pp 139-148, 1994.

Chakraborty, M., et al. Induction of Human Breast Cancer-Specific Antibody Response in Cynomolgus Monkeys by a Murine Monoclonal Anti-idiotype Antibody. Cancer Res. 55:1525-1530, 1995.

Bhattacharya-Chatterjee, M., et al. Syngeneic monoclonal anti-idiotype antibodies against a monoclonal antibody to human melanoma associated antigen. J. Immunol. 150: 142A, 1993.

Sen, G., et al. Murine Monoclonal Antibody-idiotype Antibody Breaks Tolerance and Induces Specific Antibody Response to Human Disialoganglioside GD2 in Cynomolgus Monkeys. Abstract presented at the 9th International Congress of Immunology, San Francisco, Calif., July 23-29, A5250, p885, 1995

Chapman, P. B. and Houghton, A. N. Induction of IgG antibodies against GD3 ganglioside in rabbits by an anti-idiotypic monoclonal antibody. J. Clin. Invest 88:186-192, 1991.

Saleh M. N., Stapleton, J. D., Khazaeli M. B. and LoBuglio, A. F. Generation of a human anti-idiotypic antibody that mimics the GD2 antigen. J. Immunol. 151:33909-3398, 1993.

Cheung, N.-K V., Canete, A., Cheung, I. Y., Ye, J.-N. and Liu, C. Disialoganglioside $G_{D2}$ anti-idiotypic monoclonal antibodies. Int. J. Cancer 54:499-505, 1993.

Kanda, S, Takeyama H., Kikumoto, Y., Morrison S. L., Morton D. L. and Irie, R. F. Both $V_H$ and $V_L$ regions contribute to the antigenicity of anti-idiotypic antibody that mimics melanoma associated ganglioside $GM_3$ Cell Biophys. 24/25:65-74, 1994.

Yamamoto S., Yamamoto T., Saxton R. E., Hoon D. S. B., and Irie, R. F. Anti-idiotype monoclonal antibody carrying the internal image of ganglioside GM3. J. Natl. Cancer Inst. 82:1757-1760, 1990.

Hastings, A., Morrison S. L., Kanada S., Saxton, R. E., and Irie, R. F. Production and characterization of a murine/human chimeric anti-idiotype antibody that mimics ganglioside. Cancer Res. 52:1681-1686, 1992.

Hakomori et al. U.S. Pat. No. 5,303,614. Methods for the production of antibodies and induction of immune responses to tumor-associated gangliosides by immunization with ganglioside lactones.

Livingston et al. WO 94/16731. Ganglioside-KLH conjugate vaccines with QS-21.

What is claimed as the invention is:

1. A monoclonal antibody 1A7 produced from hybridoma cell line deposited under ATCC Accession No. HB-11786.

2. An antibody producing cell, being progeny of hybridoma cells, deposited under ATCC Accession No. HB-11786 said progeny producing a monoclonal antibody which is the same as the monoclonal antibody produced from hybridoma cell line deposited under ATCC Accession No. HB-11786.

3. A purified antibody produced by a cell according to claim 2.

4. A vaccine comprising monoclonal antibody 1A7 of claim 1 and a pharmaceutically acceptable excipient for the treatment of melanoma.

5. The vaccine of claim 4, comprising an adjuvant.

* * * * *

SEQUENCE LISTING (1) GENERAL INFORMATION:

(iii) NUMBER OF SEQUENCES: 66

(2) INFORMATION FOR SEQ ID NO: 1:

(i) SEQUENCE CHARACTERISTICS:
      (A) LENGTH: 447 base pairs (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: CDS
    (B) LOCATION: 1..447

(ix) FEATURE:
    (A) NAME/KEY: mat_peptide
    (B) LOCATION: 58

(xi) SEQUENCE DESCRIPTION: SEQ ID NO: 1:

```
ATG AAG TTG CCT GTT AGG CTG TTG GTG CTG ATG TTC TGG ATT CCT GCT      48
Met Lys Leu Pro Val Arg Leu Leu Val Leu Met Phe Trp Ile Pro Ala
-19         -15                 -10                 -5

TCC AGC GAT GAT GTT TTC ATG ACC CAA ACT CCA CTC TCC CTG CCT GTC      96
Ser Ser Asp Asp Val Phe Met Thr Gln Thr Pro Leu Ser Leu Pro Val
             1               5                   10

AGT CTT GGA GAT CAA GCC TCC ATC TCT TGC AGA TCT AGT CAG AGC ATT     144
Ser Leu Gly Asp Gln Ala Ser Ile Ser Cys Arg Ser Ser Gln Ser Ile
        15                  20                  25

GTA CAT AGT AAT GGA AAC ACC TAT TTA GAA TGG TAC CTA CAG AAA CCA     192
Val His Ser Asn Gly Asn Thr Tyr Leu Glu Trp Tyr Leu Gln Lys Pro
30                  35                  40                  45

GGC CAG TCT CCA AAC CTC CTG ATC TAC TTT GTT TCC AAC CGA TTT TCT     240
Gly Gln Ser Pro Asn Leu Leu Ile Tyr Phe Val Ser Asn Arg Phe Ser
                50                  55                  60

GGG GTC CCA GAC AGG TTC AGT GGC AGT GGA TCA GGG ACA GAT TTC ACA     288
Gly Val Pro Asp Arg Phe Ser Gly Ser Gly Ser Gly Thr Asp Phe Thr
            65                  70                  75

CTC AAG ATC AGC AGA GTG GAG GCT GAG GAT CTG GGA GTT TAT TAC TGC     336
Leu Lys Ile Ser Arg Val Glu Ala Glu Asp Leu Gly Val Tyr Tyr Cys
        80                  85                  90

TTT CAA GGT TCA CAT GTT CCG TGG ACG TTC GGT GGA GGC ACC AAG CTG     384
Phe Gln Gly Ser His Val Pro Trp Thr Phe Gly Gly Gly Thr Lys Leu
                95                  100                 105

GAA ATC AAA CGG GCT GAT GCT GCA CCA ACT GTA TCC ATC TTC CCA CCA     432
Glu Ile Lys Arg Ala Asp Ala Ala Pro Thr Val Ser Ile Phe Pro Pro
110             115                 120                 125

TCC AGT AAG CTT GGG                                                  447
Ser Ser Lys Leu Gly
            130
```

(2) INFORMATION FOR SEQ ID NO: 2:

(i) SEQUENCE CHARACTERISTICS:
        (A) LENGTH: 149 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Lys Leu Pro Val Arg Leu Leu Val Leu Met Phe Trp Ile Pro Ala
-19         -15                 -10                 -5

Ser Ser Asp Asp Val Phe Met Thr Gln Thr Pro Leu Ser Leu Pro Val
             1               5                   10

Ser Leu Gly Asp Gln Ala Ser Ile Ser Cys Arg Ser Ser Gln Ser Ile
        15                  20                  25

Val His Ser Asn Gly Asn Thr Tyr Leu Glu Trp Tyr Leu Gln Lys Pro
30                  35                  40                  45
```

```
Gly Gln Ser Pro Asn Leu Leu Ile Tyr Phe Val Ser Asn Arg Phe Ser
             50                  55                  60

Gly Val Pro Asp Arg Phe Ser Gly Ser Gly Ser Gly Thr Asp Phe Thr
                 65                  70                  75

Leu Lys Ile Ser Arg Val Glu Ala Glu Asp Leu Gly Val Tyr Tyr Cys
         80                  85                  90

Phe Gln Gly Ser His Val Pro Trp Thr Phe Gly Gly Gly Thr Lys Leu
     95                 100                 105

Glu Ile Lys Arg Ala Asp Ala Ala Pro Thr Val Ser Ile Phe Pro Pro
110             115                 120                 125

Ser Ser Lys Leu Gly
             130

(2) INFORMATION FOR SEQ ID NO: 3:

(i) SEQUENCE CHARACTERISTICS:
        (A) LENGTH: 458 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..456

(ix) FEATURE:
        (A) NAME/KEY: mat_peptide
        (B) LOCATION: 58

(xi) SEQUENCE DESCRIPTION: SEQ ID NO: 3:

ATG GCT GTC TTG GGG CTG CTC TTC TGC CTG GTG ACA TTC CCA AGC TGT      48
Met Ala Val Leu Gly Leu Leu Phe Cys Leu Val Thr Phe Pro Ser Cys
-19             -15                 -10                 -5

GTC CTG TCC CAG GTG CAG GTG AAG GAG TCA GGA CCT TTC CTG GTG CCC      96
Val Leu Ser Gln Val Gln Val Lys Glu Ser Gly Pro Phe Leu Val Pro
                 1               5                  10

CCC TCA CAG AGC CTG TCC ATC ACA TGC ACT GTC TCA GGG TTC TCA TTA     144
Pro Ser Gln Ser Leu Ser Ile Thr Cys Thr Val Ser Gly Phe Ser Leu
         15                  20                  25

ACC ACC TAT GGT GTA AGC TGG ATT CGC CAG CCT CCA GGA AAG GGT CTG     192
Thr Thr Tyr Gly Val Ser Trp Ile Arg Gln Pro Pro Gly Lys Gly Leu
 30                  35                  40                  45

GAG TGG CTG GGA GCA ATT TGG GGT GAC GGG ACC ACA AAT TAT CAT TCA     240
Glu Trp Leu Gly Ala Ile Trp Gly Asp Gly Thr Thr Asn Tyr His Ser
             50                  55                  60

GCT CTC ATA TCC AGA CTG AGC ATC AGC AAG GAT AAC TCC AAG AGC CAA     288
Ala Leu Ile Ser Arg Leu Ser Ile Ser Lys Asp Asn Ser Lys Ser Gln
                 65                  70                  75

GTT TTC TTA AAA CTG AAC AGT CTG CAA ACT GAT GAC ACG GCC ACG TAC     336
Val Phe Leu Lys Leu Asn Ser Leu Gln Thr Asp Asp Thr Ala Thr Tyr
         80                  85                  90

TAC TGT GCC AAA CTG GGT AAC TAC GAT GCT CTG GAC TAC TGG GGT CAA     384
Tyr Cys Ala Lys Leu Gly Asn Tyr Asp Ala Leu Asp Tyr Trp Gly Gln
     95                 100                 105

GGA ACC TCA GTC ACC GTC TCC TCA GCC AAA ACG ACA CCC CCA CCC GTC     432
Gly Thr Ser Val Thr Val Ser Ser Ala Lys Thr Thr Pro Pro Pro Val
110                 115                 120                 125

TAT CCA TTG GTC CCT GGA AGC TTG GG                                  458
Tyr Pro Leu Val Pro Gly Ser Leu
             130
```

(2) INFORMATION FOR SEQ ID NO: 4:

(i) SEQUENCE CHARACTERISTICS:
        (A) LENGTH: 152 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Ala Val Leu Gly Leu Leu Phe Cys Leu Val Thr Phe Pro Ser Cys
-19             -15                 -10                 -5

Val Leu Ser Gln Val Gln Val Lys Glu Ser Gly Pro Phe Leu Val Pro
              1               5                  10

Pro Ser Gln Ser Leu Ser Ile Thr Cys Thr Val Ser Gly Phe Ser Leu
          15                  20                  25

Thr Thr Tyr Gly Val Ser Trp Ile Arg Gln Pro Pro Gly Lys Gly Leu
 30              35                  40                      45

Glu Trp Leu Gly Ala Ile Trp Gly Asp Gly Thr Thr Asn Tyr His Ser
             50                  55                      60

Ala Leu Ile Ser Arg Leu Ser Ile Ser Lys Asp Asn Ser Lys Ser Gln
             65                  70                  75

Val Phe Leu Lys Leu Asn Ser Leu Gln Thr Asp Thr Ala Thr Tyr
              80                  85                  90

Tyr Cys Ala Lys Leu Gly Asn Tyr Asp Ala Leu Asp Tyr Trp Gly Gln
         95                 100                 105

Gly Thr Ser Val Thr Val Ser Ser Ala Lys Thr Thr Pro Pro Pro Val
110                 115                 120                 125

Tyr Pro Leu Val Pro Gly Ser Leu
                130
```

(2) INFORMATION FOR SEQ ID NO: 5:

(i) SEQUENCE CHARACTERISTICS:
        (A) LENGTH: 98 amino acids
        (B) TYPE: amino acid
        (C) STRANDEDNESS: single
        (D) TOPOLOGY: linear (xi) SEQUENCE DESCRIPTION: SEQ ID NO: 5:

```
Gln Val Gln Val Lys Glu Ser Gly Pro Phe Leu Val Pro Pro Ser Gln
 1               5                  10                  15

Ser Leu Ser Ile Thr Cys Thr Val Ser Gly Phe Ser Leu Thr Thr Tyr
             20                  25                  30

Gly Val Ser Trp Ile Arg Gln Pro Pro Gly Lys Gly Leu Glu Trp Leu
         35                  40                  45

Gly Ala Ile Trp Gly Asp Gly Thr Thr Asn Tyr His Ser Ala Leu Ile
 50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                 85                  90                  95

Lys Leu
```

(2) INFORMATION FOR SEQ ID NO: 6:

(i) SEQUENCE CHARACTERISTICS:
        (A) LENGTH: 19 amino acids

-continued (B) TYPE: amino acid
        (C) STRANDEDNESS: single
        (D) TOPOLOGY: linear (xi) SEQUENCE DESCRIPTION: SEQ ID NO: 6:

```
Gly Asn Tyr Asp Ala Leu Asp Trp Trp Gly Gln Gly Thr Ser Val Thr
1               5                   10                  15

Val Ser Ser
```

(2) INFORMATION FOR SEQ ID NO: 7:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 7:

```
Tyr Asp Tyr Glu Xaa Xaa Xaa Xaa Xaa
1               5
```

(2) INFORMATION FOR SEQ ID NO: 8:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 8:

```
Xaa Xaa Xaa Xaa Xaa Xaa Xaa
1               5
```

(2) INFORMATION FOR SEQ ID NO: 9:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO: 9:

```
Ser Val Ser Ile Tyr Tyr Tyr Gly Arg Ser Asp Lys
1               5                   10
```

(2) INFORMATION FOR SEQ ID NO: 10:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO: 10:

```
Xaa Xaa Xaa Xaa Xaa Xaa
1               5
```

(2) INFORMATION FOR SEQ ID NO: 11:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO: 11:

```
Xaa Xaa Xaa Xaa
```

(2) INFORMATION FOR SEQ ID NO: 12:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO: 12:

```
Arg Asp Tyr Arg
1
```

(2) INFORMATION FOR SEQ ID NO: 13:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO: 13:

```
Gly Tyr Tyr Asp Xaa
1               5
```

(2) INFORMATION FOR SEQ ID NO: 14:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO: 14:

```
Xaa Xaa Xaa Xaa Xaa
1               5
```

(2) INFORMATION FOR SEQ ID NO: 15:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 15:

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Lys Gly Gln Ser
        35                  40                  45

Pro Lys Leu Leu Ile Tyr Phe Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110
```

(2) INFORMATION FOR SEQ ID NO: 16:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 16:

```
Gln Val Gln Leu Lys Glu Ser Gly Pro Gly Leu Val Ala Pro Ser Gln
  1               5                  10                  15
Ser Leu Ser Ile Thr Cys Thr Val Ser Gly Phe Ser Leu Thr Ser Tyr
             20                  25                  30
Gly Val His Trp Val Arg Gln Pro Pro Gly Lys Gly Leu Glu Trp Leu
         35                  40                  45
Gly Val Ile Trp Gly Asp Gly Ser Thr Asn Tyr Asn Ser Ala Leu Lys
     50                  55                  60
Ser Arg Leu Ser Ile Ser Lys Asp Asn Ser Lys Ser Gln Val Phe Leu
 65                  70                  75                  80
Lys Met Asn Ser Leu Gln Thr Asp Asp Thr Ala Arg Tyr Tyr Cys Ala
                 85                  90                  95
Arg Glu Xaa Xaa Xaa Xaa Tyr Tyr Ala Met Asp Tyr Trp Gly Gln Gly
            100                 105                 110
Thr Ser Val Thr Val Ser Ser
        115
```

(2) INFORMATION FOR SEQ ID NO: 17:

(i) SEQUENCE CHARACTERISTICS:
        (A) LENGTH: 336 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

```
GATGTTTTGA TGACCCAAAC TCCACTCTCC CTGCCTGTCA GTCTTGGAGA TCAAGCCTCC    60
ATCTCTTGCA GATCTAGTCA GAGCATTGTA CATAGTAATG AAACACCTA TTTAGAATGG    120
TACCTGCAGA AACCAGGCCA GTCTCCAAAG CTCCTGATCT ACAAAGTTTC CAACCGATTT    180
TCTGGGGTCC CAGACAGGTT CAGTGGCAGT GGATCAGGGA CAGATTTCAC ACTCAAGATC    240
AGCAGAGTGG AGGCTGAGGA TCTGGGAGTT TATTACTGCT TTCAAGGTTC ACATGTTCCG    300
TGGACGTTCG GTGGAGGCAC CAAGCTGGAA ATCAAA    336
```

(2) INFORMATION FOR SEQ ID NO: 18:

(i) SEQUENCE CHARACTERISTICS:
        (A) LENGTH: 336 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

```
GATGTTTTGA TGACCCAAAC TCCACTCTCC CTGCCTGTCA GTCTTGGAGA TCAAGCCTCC    60
ATCTCTTGCA GATCTAGTCA GAGCATTGTA CATAGTAATG AAACACCTA TTTAGAATGG    120
TACCTGCAGA AACCAGGCCA GTCTCCAAAG CTCCTGATCT ACAAAGTTTC CAACCGATTT    180
```

```
TCTGGGGTCC CAGACAGGTT CAGTGGCAGT GGATCAGGGA CAGATTTCAC ACTCAAGATC        240

AGCAGAGTGG AGGCTGAGGA TCTGGGAGTT TATTACTGCT TTCAAGGTTC ACATGTTCCG        300

TGGACGTTCG GTGGAGGCAC CAAGCTGGAA ATCAAA                                  336
```

(2) INFORMATION FOR SEQ ID NO: 19:

(i) SEQUENCE CHARACTERISTICS:
        (A) LENGTH: 336 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

```
GATGTTTTGA TGACCCAAAC TCCACTCTCC CTNCCTGTCA GTCTTGGAGA TCAAGCCTCC         60

ATCTCTTGCA GATCTAGTCA GAGCATTGTA CATAGTAATG GAAACACCTA TTTAGAATGG        120

TACCTGCAGA AACCAGGCCA GTCTCCAAAG CTCCTNATCT ACAAAGTTTC CAACCGATTT        180

TCTGGGGTCC CAGACAGGTT CAGTGGCAGT GGATCAGGGA CAGATTTCAC ACTCAAGATC        240

AGCAGAGTGG AGGCTGAGGA TCTGGGAGTT TATTACTGCT TTCAAGGTTC ACATGTTCCG        300

TGGACGTTCG GTGGAGGCAC CAAGCTGGAA ATCAAA                                  336
```

(2) INFORMATION FOR SEQ ID NO: 20:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

```
GATGTTTTGA TGACCCAAAC TCCACTCTCC CTGCCTGTCA GTCTTGGAGA TCAAGCCTCC         60

ATCTCTTGCA GATCTAGTCA GAGCATTGTA CATAGTAATG GAAACACCTA TTTAGAATGG        120

TACCTGCAGA AACCAGGCCA GTCTCCAAAG CTCCTGATCT ACAAAGTTTC CAACCGATTT        180

TCTGGGGTCC CAGACAGGTT CAGTGGCAGT GGATCAGGGA CAGATTTCAC ACTCAAGATC        240

AGCAGAGTGG AGGCTGAGGA TCTGGGAGTT TATTACTGCT TTCAAGGTTC ACATGTTCCG        300

TGGACGTTCG GTGGAGGCAC CAAGCTGGAA ATC                                     333
```

(2) INFORMATION FOR SEQ ID NO: 21:

(i) SEQUENCE CHARACTERISTICS:
        (A) LENGTH: 336 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

```
GATGTTTTGA TGACCCAAAC TCCACTCTCC CTGCCTGTCA GTCTTGGAGA TCAAGCCTCC         60

ATCTCTTGCA GATCTAGTCA GAGCATTGTA CATAGTAATG GAAACACCTA TTTAGAATGG        120

TACCTGCAGA AACCAGGCCA GTCTCCAAAG CTCCTGATCT ACAAAGTTTC CAACCGATTT        180

TCTGGGGTCC CAGACAGGTT CAGTGGCAGT GGATCAGGGA CAGATTTCAC ACTCAAGATC        240

AGCAGAGTGG AGGCTGAGGA TCTGGGAGTT TATTACTGCT TTCAAGGTTC ACATGTTCCT        300
```

```
CGGACGTTCG GTGGAGGCAC CAAGCTGGAA ATCAAA                                    336

(2) INFORMATION FOR SEQ ID NO: 22:

(i) SEQUENCE CHARACTERISTICS:
        (A) LENGTH: 336 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

GATGTTGTGA TGACCCAAAC TCCACTCTCC CTGCCTGTCA GTCTTGGAGA TCAAGCCTCC            60

ATCTCTTGCA GATCTAGTCA GAGCATTGTA CATAGTAATG GAAACACCTA TTTAGAATGG          120

TACCTGCAGA AGCCAGGCCA GTCTCCAAAG CTCCTGATCT ACAAAGTTTC CAACCGATTT          180

TCTGGGGTCC CAGACAGGTT CAGTGGCAGT GGATCAGGGA CAGATTTCAC ACTCAAGATC          240

AGCAGAGTGG AGGCTGAGGA TCTGGGAGTT TATTACTGCT TTCAAGGTTC ACATGTTCCT          300

TGGACGTTCG GTGGAGGCAC CAAGCTGGAA ATCAAA                                    336

(2) INFORMATION FOR SEQ ID NO: 23:

(i) SEQUENCE CHARACTERISTICS:
        (A) LENGTH: 336 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

GATGTTTTGA TGACNCAAAC TCCACTCTCC CTGCCTGTCA GTCTTGGAGA TCAAGCCTCC            60

ATCTCTTGCA GATCTAGTCA GAGCATTGTA CATAGTAATG GAAACACCTA TTTAGAATGG          120

TACCTGCAGA AACCAGGCCA GTCTCCAAAG CTCCTNATCT ACAAAGTTTC CAACCGATTT          180

TCTGGGGTCC CAGANAGGTT CAGTGGCAGT GGATCAGGGA CAGATTTCAC ACTCAAGATC          240

AGCAGAGTGG AGGCTGAGGA TCTGGGAGTT TATTACTGCT TTCAAGGTTC ACATGTTCCG          300

TGGACGTTCG GTGGAGGCAC CAAGCTGGAA ATCAAA                                    336

(2) INFORMATION FOR SEQ ID NO: 24:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

GATGTTTTGA TGACCCAAAC TCCACTCTCC CTGCCTGTCA GTCTTGGAGA TCAAGCCTCC            60

ATCTCTTGCA GATCTAGTCA GAGCATTGTA CATAGTAATG GAAACACCTA TTTAGAATGG          120

TACCTGCAGA AACCAGGCCN GTCTCCAAAG CTCCTGATCT ACAAAGTTTC CAACCGATTT          180

TCTGGGGTCC CAGACAGGTT CAGTGGCAGT GGATCAGGGA CAGATTTCAC ACTCAAGATC          240

AGCAGAGTGG AGGCTGAGGA TCTGGGAGTT TATTACTGCT TTCAAGGTTC ACATGTTCCG          300

TGGACGTTCG GTGGAGGCAC CAAGCTGGAA ATC                                       333
```

(2) INFORMATION FOR SEQ ID NO: 25:

(i) SEQUENCE CHARACTERISTICS:
        (A) LENGTH: 336 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 25:

```
GATGTTTTAA TGACCCAAAC TCCACTCTCC CTGCCTGTCA GTCTTGGAGA TCAAGCCTCC    60
ATCTCTTGCA GATCTAGTCA GAGCATTGTA CATAGTAATG AAACACCTA TTTAGAATGG    120
TACCTGCAGA AACCAGGCCA GTCTCCAAAG CTCCTGATCT ACAAAGTTTC CAACCGATTT   180
TCTGGGGTCC CAGACAGGTT CAGTGGCAGT GGATCAGGGA CAGATTTCAC ACTCAAGATC   240
AGCAGAGTGG AGGCTGAGGA TCTGGGAGTT TATTACTGCT TTCAAGGTTC ACATGTTCCG   300
TGGACGTTCG GTGGAGGCAC CAAGCTGGAA ATCAAA                             336
```

(2) INFORMATION FOR SEQ ID NO: 26:

(i) SEQUENCE CHARACTERISTICS:
        (A) LENGTH: 336 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 26:

```
GATGTTTTGA TGACCCAAAC TCCACTCTCC CTGCCTGTCA GTCTTGGAGA TCAAGCCTCC    60
ATCTCTTGCA GATCTAGTCA GAGCATTGTA CATAGTAGTG AAACACCTT TTTAGAATGG   120
TACCTGCAGA AACCAGGCCA GTCTCCAAAG CTCCTGATCT ACAAAGTTTC CAACCGATTT   180
TCTGGGGTCC CAGACAGGTT CAGTGGCAGT GGATCAGGGA CAGATTTCAC ACTCAAGATC   240
AGCAGGGTGG AGGCTGAGGA TCTGGGAGTT TATTACTGCT TTCAAGGTAC ACATGTTCCG   300
TGGACGTTCG GTGGAGGCAC CAAGCTGGAA ATCAAA                             336
```

(2) INFORMATION FOR SEQ ID NO: 27:

(i) SEQUENCE CHARACTERISTICS:
        (A) LENGTH: 291 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 27:

```
CAGGTGCAGC TGCAGGAGTC AGGACCTGGC CTGGTGGCGC CCTCACAGAG CCTGTCCATC    60
ACATGCACTG TCTCAGGGTT CTCATTAACC AGCTATGGTA TAACCTGGGT TCGCCAGCCT   120
CCAGGAAAGG GTCTGGAGTG GCTGGGAGTA ATATGGGGTG ACGGAAACAC AAATTATCAT   180
TCAGCTCTCA TATCCAGACT GAGCATCAGC AAGGATAACT CCAAGAGCCA AGTTTTCTTA   240
AAACTGAACA GTCTGCAAAC TGATGACACA GCCACGTACT ACTGTGCCAA A            291
```

(2) INFORMATION FOR SEQ ID NO: 28:

(i) SEQUENCE CHARACTERISTICS:
        (A) LENGTH: 45 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO: 28:

GCTAAGGACT ACTGGGGTCA AGGAACCTCA GTCACCGTCT CCTCA                45

(2) INFORMATION FOR SEQ ID NO: 29:

(i) SEQUENCE CHARACTERISTICS:
        (A) LENGTH: 292 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 29:

CAGGTGCAGC TGAAGGAGAC AGGACCTGGC CTGGTGGCGC CCTCACAGAG CCTGTCCATC    60

ACATGCACCG TCTCAGGGTT CTCATTAACC AGCTATGGTG TACACTGGGT TCGCCAGCCT   120

CCAGGAAAGG GTCTGGAGTG GCTGGTAGTG ATATGGAGTG ATGGAAGCAC AAACTATAAT   180

TCAGCTCTCA AATCCAGACT GAGCATCAGC AAGGACAACT CCAAGAGCCA AGTTTTCTTA   240

AAAATGAACA GTCTCCAAAC TGATGACACA GCCATGTACT ACTGTGCCAG AC          292

(2) INFORMATION FOR SEQ ID NO: 30:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 30:

GGTGACTACT ATGCTATGGA CTACTGGGGT CAAGGAACCT CAGTCACCGT CTCCTCA       57

(2) INFORMATION FOR SEQ ID NO: 31:

(i) SEQUENCE CHARACTERISTICS:
        (A) LENGTH: 336 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 31:

CAGGTGCAGC TGAAGGAGTC AGGACCTGGC CTGGTGGCGC CCTCACAGAG CCTGTCCATC    60

ACATGCACTG TCTCAGGGTT CTCATTAACC AGCTATGGTG TAAGCTGGGT TCGCCAGCCT   120

CCAGGAAAGG GTCTGGAGTG GCTGGGAGTA ATATGGGGTG ACGGGAGCAC AAATTATCAT   180

TCAGCTCTCA TATCCAGACT GAGCATCAGC AAGGATAACT CCAAGAGCCA AGTTTTCTTA   240

AAACTGAACA GTCTGCAAAC TGATGACACA GCCACGTACT ACTGTGCCAA GCATCTTGAC   300

TACTGGGGCC AAGGCACCAC TCTCACAGTC TCCTCA                            336

(2) INFORMATION FOR SEQ ID NO: 32:

(i) SEQUENCE CHARACTERISTICS:
        (A) LENGTH: 304 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 32:

CAGGTGCAGC TGAAGGAGTC AGGACCTGGC CTGGTGGCGC CCTCACAGAG CCTGTCCATC    60

ACTTGCACTG TCTCTGGGTT TTCATTAACC AGCTATGGTG TACACTGGGT TCGCCAGCCT    120

CCAGGAAAGG GTCTGGAGTG GCTGGGAGTA ATATGGGCTG GTGGAAGCAC AAATTATAAT    180

TCGGCTCTCA TGTCCAGACT GAGCATCAGC AAAGACAACT CCAAGAGCCA AGTTTTCTTA    240

AAAATGAACA GTCTGCAAAC TGATGACACA GCCATGTACT ACTGTGCCAG AGGGCATTAC    300

TACG                                                                304

(2) INFORMATION FOR SEQ ID NO: 33:

(i) SEQUENCE CHARACTERISTICS:
            (A) LENGTH: 49 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 33:

CTACTATGCT ATGGACTACT GGGGTCAAGG AACCTCAGTC ACCGTCTCC                 49

(2) INFORMATION FOR SEQ ID NO: 34:

(i) SEQUENCE CHARACTERISTICS:
            (A) LENGTH: 292 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 34:

CAGGTGCAGC TCAAGGAGTC AGGACCTGTC CTCGTGGCGC CCTCACAGAG CCTGTCCATC    60

ACTTGCACTG TCTCTGGGTT TTCATTAACC AGCTATGGTG TACACTGGGT TCGCCAGCCT    120

CCAGGCAAGG GTCTGGAGTG GCTGGGAGTA ATATGGGCTG GTGGAAGCAC AAATTATAAT    180

TCAGCTCTCA TGTCCAGACT GAGCATCAGC AAAGACAACT CCAAGAGCCA AGTTTTCTTA    240

AAAATGAACA GTCTGCAAAC TGATGACACA GCCATGTACT ACTGTGCCAA AC            292

(2) INFORMATION FOR SEQ ID NO: 35:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 35:

ACAATGCTAT GGACTACTGG GGTCAAGGAA CCTCAGTCAC NGTCTCCTCA                50

(2) INFORMATION FOR SEQ ID NO: 36:

(i) SEQUENCE CHARACTERISTICS:
            (A) LENGTH: 351 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 36:

```
CAGGTNCAGC TGAAGGAGTC AGGACCTGGC CTGGTGGCAC CCTCACAGAG CCTGTCCATC    60
ACATGCACTG TCTCTGGGTT CTCATTATCC AGATATAGTG TACACTGGGT TCGCCAGCCT   120
CCAGGAAAGG GTCTTGAGTG GCTGGGAATG ATATGGGGTG GTGGAAACAC AGACTATAAT   180
TCAGCTCTCA AATCCAGACT GAGCATCAGC AAGGACAACT CCAAGAGCCA AGTTTTCTTA   240
AAAATGAACA GTCTGCAAAC TGATGACACA GCCATGTACT ACTGTGCCAG AGATGGTTAC   300
TACGACTATG CTATGGACTA CTGGGGTCAA GGAACCTCAG TCACCGTCTC C            351
```

(2) INFORMATION FOR SEQ ID NO: 37:

(i) SEQUENCE CHARACTERISTICS:
        (A) LENGTH: 291 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 37:

```
CAGGTGCAGC TGAAGGAGTC AGGACCTGGC CTGGTGGCGC CCTCACAGAG CCTGTCCATC    60
ACTTGCACTG TCTCTGGGTT TTCATTAACC AGCTATGGTG TACACTGGGT TCGCCAGCCT   120
CCAGGAAAGG GTCTGGAGTG GCTGGGAGTA ATATGGGCTG GTGGAAGCAC AAATTATAAT   180
TCGGCTCTCA TGTCCAGACT GAGCATCAGC AAAGACAACT CCAAGAGCCA AGTTTTCTTA   240
AAAATGAACA GTCTGCAAAC TGATGACACA GCCATGTACT ACTGTGCCAG A            291
```

(2) INFORMATION FOR SEQ ID NO: 38:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 38:

```
TACTATGCTA TGGACTACTG GGGTCAAGGA ACCTCAGTCA CCGTCTCC                 48
```

(2) INFORMATION FOR SEQ ID NO: 39:

(i) SEQUENCE CHARACTERISTICS:
        (A) LENGTH: 292 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 39:

```
CACGTGCACC TGAAGGAGTC AGGACCTGTC CTGGTGGCGC CCTCACAGAG CCTGTCCATC    60
ACTTGCACTG TCTCTGGGTT TTCATTAACC AACTATGGTG TACACTGGGT TCGCCAGCCT   120
CCAGGAAAGG GTCTGGAGTG GCTGGGAGTA ATATGGGCTG GTGGAAACAC AAATTATAAT   180
TCAGCTCTCA TGTCCAGACT GAGCATCAGC AAAGACAATT CCAAGAGCCA AGTTTTCTTA   240
AAAATGAACA GTCTGCAAAT TGATGACACA GCCATATACT ACTGTGCCAA AC           292
```

(2) INFORMATION FOR SEQ ID NO: 40:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 40:

TACTATGCTA TGGACTATTG GGGTCAAGGA ACCTCAGTCA CCGTCTCCTC A            51

(2) INFORMATION FOR SEQ ID NO: 41:

(i) SEQUENCE CHARACTERISTICS:
        (A) LENGTH: 288 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 41:

CAGGTGCAGC TGAAGGAGTC AGGACCTGGC CTGGTGGCGC CCTCACAGAG CCTGTCCATC      60

ACTTGCACTG TCTCTGGGTT TCCATTAACC AGCTATGGTG TAGACTGGGT TCGCCAGCCT     120

CCAGGAAAGG GTCTGGAGTG GCTGGGAGTA ATATGGGGTG GTGGAAGCAC NAATTATAAT     180

TCAGCTCTCA TGTCCAGACT GAGCATCAGC AAAGACAACT CCAAGAGCCA AGTTTTCTTA    240

AAAATGAACA GTCTGCNAAC TGATGACACA GCCATGTACT ACTGTGCC                 288

(2) INFORMATION FOR SEQ ID NO: 42:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 42:

ACGGGGNNTT TACTATGCTA TGGACTACTG GGGTCAAGGA ACCTCAGTCA CCGTCTC        57

(2) INFORMATION FOR SEQ ID NO: 43:

(i) SEQUENCE CHARACTERISTICS:
        (A) LENGTH: 293 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 43:

CAGGTGCACC TGAAGGAGTC AGGACCTGGC CTGGTGGCGC CCTCACAGAG CCTGTCCATC      60

ACTTGCACTG TCTCTGGATT TTCATTAACC ACCTATGGTG TACACTGGTT TCGCCAGCCT    120

CCAGGAAAGG GTCTGGAGTG GCTGGGACTA ATATGGGCTG GTGGAAACAC AGATTATAAT    180

TCGGCTCTCA TGTCCAGACT GAGCATCAAC AAAGACAACT CCAAGAGCCA AGTTTTCTTA    240

AAAATGAACA GTCTGCAAGC TGATGACACA GCCATGTACT ACTGTGCCAG ATT           293

(2) INFORMATION FOR SEQ ID NO: 44:

(i) SEQUENCE CHARACTERISTICS:
        (A) LENGTH: 53 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 44:

ACGACTATGC TGTGGACTAC TGGGGTCAAG GAACCTCAGT CACCGTCTCC TCA          53

(2) INFORMATION FOR SEQ ID NO: 45:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 45:

Gly Gly Gly Gly Ser Gly Gly Gly Gly Ser Gly Gly Gly Gly Ser
1               5                  10                  15

(2) INFORMATION FOR SEQ ID NO: 46:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 30
        (D) OTHER INFORMATION: /note= "N represents the Nucleotide
            Inosine(I)"

(xi) SEQUENCE DESCRIPTION: SEQ ID NO: 46:

CCCAAGCTTC CAGGGRCCAR KGGATARACN GRTGG                              35

(2) INFORMATION FOR SEQ ID NO: 47:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 47:

ACTAGTCGAC ATGGCTGTCY TRGBGCTGYT CYTCTG                             36

(2) INFORMATION FOR SEQ ID NO: 48:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 48:

TAATACGACT CACTATAGGG                                               20

(2) INFORMATION FOR SEQ ID NO: 49:

(i) SEQUENCE CHARACTERISTICS:
        (A) LENGTH: 19 base pairs
        (B) TYPE: nucleic acid
        (C) STRANDEDNESS: single
        (D) TOPOLOGY: linear
```

(xi) SEQUENCE DESCRIPTION: SEQ ID NO: 49:

GTTTTCCCAG TCACGACGT                                                    19

(2) INFORMATION FOR SEQ ID NO: 50:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO: 50:

ACTAGTCGAC ATGAAGTTGC CTGTTAGGCT GTTGGTGCT                               39

(2) INFORMATION FOR SEQ ID NO: 51:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 51:

CCCAAGCTTA CTGGATGGTG GGAAGATGGA                                        30

(2) INFORMATION FOR SEQ ID NO: 52:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 52:

CAGATGGAAG GGCCCAAC                                                     18

(2) INFORMATION FOR SEQ ID NO: 53:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 53:

GATTGATGCA TATCATTACC                                                   20

(2) INFORMATION FOR SEQ ID NO: 54:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 54:

GTTATCGATG TCGAATAGCC                                                   20

(2) INFORMATION FOR SEQ ID NO: 55:

(i) SEQUENCE CHARACTERISTICS:
        (A) LENGTH: 24 base pairs
        (B) TYPE: nucleic acid
        (C) STRANDEDNESS: single
        (D) TOPOLOGY: linear

```
         (xi) SEQUENCE DESCRIPTION: SEQ ID NO: 55:

TTGCTGCAGA TTGAGTACTG TTCT                                           24

(2) INFORMATION FOR SEQ ID NO: 56:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (xi) SEQUENCE DESCRIPTION: SEQ ID NO: 56:

GCCGATATCA CCATGGCTGT CTTGGGGCTG CTC                                 33

(2) INFORMATION FOR SEQ ID NO: 57:

(i) SEQUENCE CHARACTERISTICS:
         (A) LENGTH: 81 base pairs
         (B) TYPE: nucleic acid
         (C) STRANDEDNESS: single
         (D) TOPOLOGY: linear (xi) SEQUENCE DESCRIPTION: SEQ ID NO: 57:

TTGGGTCATC AAAACATCGG ATCCGCCGCC ACCCGAGCCG CCACCGCCCG AGCCACCTCC    60

CCCTGAGGAG ACGGTGACTG A                                              81

(2) INFORMATION FOR SEQ ID NO: 58:

(i) SEQUENCE CHARACTERISTICS:
         (A) LENGTH: 81 base pairs
         (B) TYPE: nucleic acid
         (C) STRANDEDNESS: single
         (D) TOPOLOGY: linear (xi) SEQUENCE DESCRIPTION: SEQ ID NO: 58:

TCAGTCACCG TCTCCTCAGG GGGAGGTGGC TCGGGCGGTG GCGGCTCGGG TGGCGGCGGA    60

TCCGATGTTT TGATGACCCA A                                              81

(2) INFORMATION FOR SEQ ID NO: 59:

(i) SEQUENCE CHARACTERISTICS:
         (A) LENGTH: 34 base pairs
         (B) TYPE: nucleic acid
         (C) STRANDEDNESS: single
         (D) TOPOLOGY: linear (xi) SEQUENCE DESCRIPTION: SEQ ID NO: 59:

CATCTCTAGA TTATTTGATT TCCAGCTTGG TGCC                                34

(2) INFORMATION FOR SEQ ID NO: 60:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (xi) SEQUENCE DESCRIPTION: SEQ ID NO: 60:

GCCGATATCA CCATGGAGTT GCCTGTTAGG CTG                                 33

(2) INFORMATION FOR SEQ ID NO: 61:

(i) SEQUENCE CHARACTERISTICS:
         (A) LENGTH: 87 base pairs
         (B) TYPE: nucleic acid
```

-continued

```
            (C) STRANDEDNESS: single
            (D) TOPOLOGY: linear (xi) SEQUENCE DESCRIPTION: SEQ ID NO: 61:

TGACTCCTTC ACCTGCACCT GGGATCCGCC GCCACCCGAG CCGCCACCGC CCGAGCCACC      60

TCCCCCTTTG ATTTCCAGCT TGGTGCC                                         87

(2) INFORMATION FOR SEQ ID NO: 62:

(i) SEQUENCE CHARACTERISTICS:
            (A) LENGTH: 87 base pairs
            (B) TYPE: nucleic acid
            (C) STRANDEDNESS: single
            (D) TOPOLOGY: linear (xi) SEQUENCE DESCRIPTION: SEQ ID NO: 62:

GGCACCAAGC TGGAAATCAA AGGGGGAGGT GGCTCGGGCG GTGGCGGCTC GGGTGGCGGC      60

GGATCCCAGG TGCAGGTGAA GGAGTCA                                         87

(2) INFORMATION FOR SEQ ID NO: 63:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (xi) SEQUENCE DESCRIPTION: SEQ ID NO: 63:

CATCTCTAGA TTATGAGGAG ACGGTGACTG AGGT                                  34

(2) INFORMATION FOR SEQ ID NO: 64:

(i) SEQUENCE CHARACTERISTICS:
            (A) LENGTH: 7 base pairs
            (B) TYPE: nucleic acid
            (C) STRANDEDNESS: single
            (D) TOPOLOGY: linear (xi) SEQUENCE DESCRIPTION: SEQ ID NO: 64:

ACCATGG                                                                7

(2) INFORMATION FOR SEQ ID NO: 65:

(i) SEQUENCE CHARACTERISTICS:
            (A) LENGTH: 814 base pairs
            (B) TYPE: nucleic acid
            (C) STRANDEDNESS: double
            (D) TOPOLOGY: linear (ii) MOLECULE TYPE: DNA (genomic)

(ix) FEATURE:
            (A) NAME/KEY: CDS
            (B) LOCATION: 13..801

(xi) SEQUENCE DESCRIPTION: SEQ ID NO: 65:

GCCGATATCA CC ATG GCT GTC TTG GGG CTG CTC TTC TGC CTG GTG ACA         48
              Met Ala Val Leu Gly Leu Leu Phe Cys Leu Val Thr
              135                 140                 145

TTC CCA AGC TGT GTC CTG TCC CAG GTG CAG GTG AAG GAG TCA GGA CCT       96
Phe Pro Ser Cys Val Leu Ser Gln Val Gln Val Lys Glu Ser Gly Pro
            150                 155                 160

TTC CTG GTG CCC CCC TCA CAG AGC CTG TCC ATC ACA TGC ACT GTC TCA      144
Phe Leu Val Pro Pro Ser Gln Ser Leu Ser Ile Thr Cys Thr Val Ser
            165                 170                 175
```

-continued

| | |
|---|---|
| GGG TTC TCA TTA ACC ACC TAT GGT GTA AGC TGG ATT CGC CAG CCT CCA<br>Gly Phe Ser Leu Thr Thr Tyr Gly Val Ser Trp Ile Arg Gln Pro Pro<br>             180                          185                          190 | 192 |
| GGA AAG GGT CTG GAG TGG CTG GGA GCA ATT TGG GGT GAC GGG ACC ACA<br>Gly Lys Gly Leu Glu Trp Leu Gly Ala Ile Trp Gly Asp Gly Thr Thr<br>195                          200                          205 | 240 |
| AAT TAT CAT TCA GCT CTC ATA TCC AGA CTG AGC ATC AGC AAG GAT AAC<br>Asn Tyr His Ser Ala Leu Ile Ser Arg Leu Ser Ile Ser Lys Asp Asn<br>210                          215                          220                     225 | 288 |
| TCC AAG AGC CAA GTT TTC TTA AAA CTG AAC AGT CTG CAA ACT GAT GAC<br>Ser Lys Ser Gln Val Phe Leu Lys Leu Asn Ser Leu Gln Thr Asp Asp<br>             230                          235                          240 | 336 |
| ACG GCC ACG TAC TAC TGT GCC AAA CTG GGT AAC TAC GAT GCT CTG GAC<br>Thr Ala Thr Tyr Tyr Cys Ala Lys Leu Gly Asn Tyr Asp Ala Leu Asp<br>                   245                          250                          255 | 384 |
| TAC TGG GGT CAA GGA ACC TCA GTC ACC GTC TCC TCA GGG GGA GGT GGC<br>Tyr Trp Gly Gln Gly Thr Ser Val Thr Val Ser Ser Gly Gly Gly Gly<br>             260                          265                          270 | 432 |
| TCG GGC GGT GGC GGC TCG GGT GGC GGC GGA TCC GAT GTT TTG ATG ACC<br>Ser Gly Gly Gly Gly Ser Gly Gly Gly Gly Ser Asp Val Leu Met Thr<br>275                          280                          285 | 480 |
| CAA ACT CCA CTC TCC CTG CCT GTC AGT CTT GGA GAT CAA GCC TCC ATC<br>Gln Thr Pro Leu Ser Leu Pro Val Ser Leu Gly Asp Gln Ala Ser Ile<br>290                          295                          300                     305 | 528 |
| TCT TGC AGA TCT AGT CAG AGC ATT GTA CAT AGT AAT GGA AAC ACC TAT<br>Ser Cys Arg Ser Ser Gln Ser Ile Val His Ser Asn Gly Asn Thr Tyr<br>             310                          315                          320 | 576 |
| TTA GAA TGG TAC CTA CAG AAA CCA GGC CAG TCT CCA AAC CTC CTG ATC<br>Leu Glu Trp Tyr Leu Gln Lys Pro Gly Gln Ser Pro Asn Leu Leu Ile<br>                   325                          330                     335 | 624 |
| TAC TTT GTT TCC AAC CGA TTT TCT GGG GTC CCA GAC AGG TTC AGT GGC<br>Tyr Phe Val Ser Asn Arg Phe Ser Gly Val Pro Asp Arg Phe Ser Gly<br>             340                          345                          350 | 672 |
| AGT GGA TCA GGG ACA GAT TTC ACA CTC AAG ATC AGC AGA GTG GAG GCT<br>Ser Gly Ser Gly Thr Asp Phe Thr Leu Lys Ile Ser Arg Val Glu Ala<br>355                          360                          365 | 720 |
| GAG GAT CTG GGA GTT TAT TAC TGC TTT CAA GGT TCA CAT GTT CCG TGG<br>Glu Asp Leu Gly Val Tyr Tyr Cys Phe Gln Gly Ser His Val Pro Trp<br>370                          375                          380                     385 | 768 |
| ACG TTC GGT GGA GGC ACC AAG CTG GAA ATC AAA TAATCTAGAG ATG<br>Thr Phe Gly Gly Gly Thr Lys Leu Glu Ile Lys<br>                   390                          395 | 814 |

(2) INFORMATION FOR SEQ ID NO: 66:

(i) SEQUENCE CHARACTERISTICS:
        (A) LENGTH: 263 amino acids
        (B) TYPE: amino acid
        (D) TOPOLOGY: linear (ii) MOLECULE TYPE: protein (xi) SEQUENCE DESCRIPTION: SEQ ID NO: 66:

Met Ala Val Leu Gly Leu Leu Phe Cys Leu Val Thr Phe Pro Ser Cys
 1              5                 10                15

Val Leu Ser Gln Val Gln Val Lys Glu Ser Gly Pro Phe Leu Val Pro
           20                 25                 30

Pro Ser Gln Ser Leu Ser Ile Thr Cys Thr Val Ser Gly Phe Ser Leu
         35                 40                 45

Thr Thr Tyr Gly Val Ser Trp Ile Arg Gln Pro Pro Gly Lys Gly Leu
     50                 55                 60

```
Glu Trp Leu Gly Ala Ile Trp Gly Asp Gly Thr Thr Asn Tyr His Ser
 65                  70                  75                  80

Ala Leu Ile Ser Arg Leu Ser Ile Ser Lys Asp Asn Ser Lys Ser Gln
                 85                  90                  95

Val Phe Leu Lys Leu Asn Ser Leu Gln Thr Asp Asp Thr Ala Thr Tyr
                100                 105                 110

Tyr Cys Ala Lys Leu Gly Asn Tyr Asp Ala Leu Asp Tyr Trp Gly Gln
             115                 120                 125

Gly Thr Ser Val Thr Val Ser Ser Gly Gly Gly Ser Gly Gly Gly
         130                 135                 140

Gly Ser Gly Gly Gly Gly Ser Asp Val Leu Met Thr Gln Thr Pro Leu
145                 150                 155                 160

Ser Leu Pro Val Ser Leu Gly Asp Gln Ala Ser Ile Ser Cys Arg Ser
                165                 170                 175

Ser Gln Ser Ile Val His Ser Asn Gly Asn Thr Tyr Leu Glu Trp Tyr
             180                 185                 190

Leu Gln Lys Pro Gly Gln Ser Pro Asn Leu Leu Ile Tyr Phe Val Ser
         195                 200                 205

Asn Arg Phe Ser Gly Val Pro Asp Arg Phe Ser Gly Ser Gly Ser Gly
         210                 215                 220

Thr Asp Phe Thr Leu Lys Ile Ser Arg Val Glu Ala Glu Asp Leu Gly
225                 230                 235                 240

Val Tyr Tyr Cys Phe Gln Gly Ser His Val Pro Trp Thr Phe Gly Gly
             245                 250                 255

Gly Thr Lys Leu Glu Ile Lys
         260
```